(12) United States Patent
Kolczewski et al.

(10) Patent No.: US 8,367,838 B2
(45) Date of Patent: Feb. 5, 2013

(54) AMINES OR AMINO ALCOHOLS AS GLYT1 INHIBITORS

(75) Inventors: Sabine Kolczewski, Loerrach (DE); Hans-Peter Marty, Basel (CH); Robert Narquizian, Saint Louis (FR); Emmanuel Pinard, Linsdorf (FR); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/480,520

(22) Filed: May 25, 2012

(65) Prior Publication Data

US 2012/0232033 A1    Sep. 13, 2012

Related U.S. Application Data

(63) Continuation of application No. 12/703,802, filed on Feb. 11, 2010, now abandoned.

(30) Foreign Application Priority Data

Feb. 18, 2009    (EP) .................................... 09153112

(51) Int. Cl.
    *C07D 213/00*    (2006.01)
    *C07D 213/63*    (2006.01)
    *C07D 405/00*    (2006.01)
    *A61K 31/44*     (2006.01)

(52) U.S. Cl. ..................... 546/290; 546/283.4; 546/339; 514/336; 514/345

(58) Field of Classification Search .......................... None
See application file for complete search history.

(56) References Cited

FOREIGN PATENT DOCUMENTS

| EP | 0008532 | 3/1980 |
|---|---|---|
| GB | 313617 | 7/1930 |

OTHER PUBLICATIONS

Lopez-Corcuera et al., "Mol. Mem. Biol." 18:13-20 ( 2001).
Mohn et al., "Cell" 98:427-436 ( 1999).
Benjamin et al., "Journal of the American Chemical Society" 83:3662-3668 ( 1961).
Mai et al., "Online Journal of Organic Chem. Arkat, USA, Inc." 16:216-222 ( 2008).
Lewis et al., "Neuron" 28:325-333 ( 2000).
Drefahl et al., "Chemische Berichte" (English language translation attached), 91:750-754 ( 1958).
Gainetdinov et al., "Trends in Pharm. Sci." 23(8):367-373 ( 2002).
Vandenberg et al., "Exp. Opin. Ther. Targets" 5(4):507-518 ( 2001).
Shimizu et al., "Elsevier Science Publishers, Amsterdam" 54(35):10265-10274 ( 1998).
Javitt et al., "Biol. Psychiatry" 45:668-679 ( 1999).
Sharma et al., "Br. J. Psychiatry" ((Suppl. 28)), 174:44-51 ( 1999).
Nohira et al., "Heterocycles, Elsevier Science Publishers, B. V. Amsterdam" 52(3):1359-1370 ( 2000).
Chen et al., "J. Neurophysiol." 89(2):691-703 ( 2003).
Armer et al., "Exp. Opin. Ther. Patents" 11(4):563-572 ( 2001).
Carlsson, M. L., "J. Neural Transm." 105:525-535 ( 1998).
Bliss et al., "Nature" 361:31-39 ( 1993).
Pralong et al., "Prog. Neurobiol." 67:173-202 ( 2002).
Nakazoto et al., "Exp. Opin. Ther. Patents" 10(1):75-98 ( 2000).
Tang et al., "Nature" 401:63-69 ( 1999).
Bergereon et al., "Proc. Natl. Acad. Sci. USA" 95:15730-15734 ( 1998).

*Primary Examiner* — Janet Andres
*Assistant Examiner* — Heidi Reese
(74) *Attorney, Agent, or Firm* — George W. Johnston; Patricia S. Rocha-Tramaloni; Kimberly J. Prior

(57) ABSTRACT

The invention relates to the use of compounds of formula I

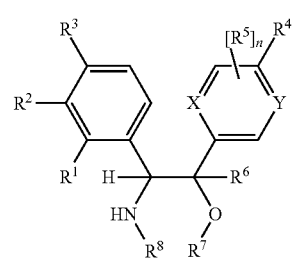

wherein the substituents are described in the description and claims for the treatment of psychoses, dysfunction in memory and learning, schizophrenia, dementia, attention deficit disorders or Alzheimer's disease. The invention also relates to some compounds of formula I and pharmaceutical compositions containing them.

28 Claims, No Drawings

AMINES OR AMINO ALCOHOLS AS GLYT1 INHIBITORS

PRIORITY TO RELATED APPLICATION(S)

This application is a continuation of U.S. application Ser. No. 12/703,802, filed Feb. 11, 2010, now pending; which claims the benefit of European Patent Application No. 09153112.9, filed Feb. 18, 2009. The entire contents of the above-identified applications are hereby incorporated by reference.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly addresses negative and cognitive symptoms which are the best redictors of functional outcome (Sharma T., *Br. J. Psychiatry*, 174(suppl. 28): 44-51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit displays behavioural abnormalities similar to those observed in pharmacologically induced models of schizophrenia, supporting a model in which reduced NMDA receptor activity results in schizophrenia-like behaviour (Mohn A R et al., *Cell*, 98: 427-236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, N Y; Bliss T V and Collingridge G L, *Nature*, 361: 31-39, 1993). Transgenic mice overexpressing the NMDA NR2B subunit exhibit enhanced synaptic plasticity and superior ability in learning and memory (Tang J P et al., *Nature*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, *Trends in Pharm. Sci.*, 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95: 15730-15734, 1998; Chen L. et al., *J. Neurophysiol.*, 89(2): 691-703, 2003).

Glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans.*, 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001).

Thus, increasing glycine activation of NMDA receptors via GlyT-1 inhibition can lead to agents that treat psychosis, schizophrenia, dementia and other diseases in which cognitive processes are impaired, such as attention deficit disorders or Alzheimer's disease.

SUMMARY OF THE INVENTION

The present invention provides a method for treatment of psychoses, dysfunction in memory and learning, schizophrenia, dementia, attention deficit disorder, or Alzheimer's disease which comprises administering a compound of formula I

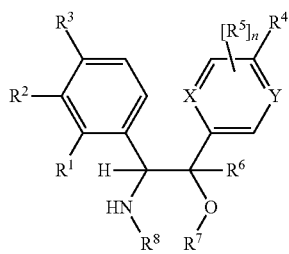

I wherein
R$^1$ is hydrogen, halogen, lower alkyl, or lower alkoxy,
R$^2$ is hydrogen, halogen, lower alkyl, or lower alkoxy,
R$^3$ is hydrogen, halogen, lower alkoxy or lower alkyl, wherein the lower alkyl is optionally substituted by halogen,
R$^4$ is a) hydrogen,
  b) halogen,
  c) lower alkyl, optionally substituted by halogen, lower alkoxy or hydroxyl,
  d) lower alkoxy, optionally substituted by halogen, hydroxyl, cycloalkyl or heterocyclyl,
  e) —NR$^{11}$R$^{12}$,
  f) —S(O)$_2$-lower alkyl,
  g) —Si(lower alkyl)$_3$,
  h) —O-cycloalkyl,
  i) —O-aryl,
  j) —O-heteroaryl,
  k) —O-heterocyclyl,
  l) aryl,
  m) heteroaryl, or
  n) heterocyclyl,
  wherein each of the cycloalkyl, aryl, heteroaryl and heterocyclyl is optionally substituted by halogen, amido, nitro, acetyl, acetamidyl, lower alkyl, halogen-lower alkyl, lower alkoxy-lower alkyl, —NR$^{11}$R$^{12}$, lower alkoxy, halogen-lower alkoxy, or —S(O)$_2$-lower alkyl,
  and wherein each S being part of a heterocyclyl is optionally substituted by oxo,
R$^5$ is halogen, lower alkyl, or lower alkoxy,
R$^6$ is hydrogen or lower alkyl,
R$^7$ is hydrogen or lower alkyl,
R$^8$ is hydrogen or lower alkyl,
R$^9$ is hydrogen, halogen, lower alkyl, or lower alkoxy,
R$^{10}$ is hydrogen, halogen, lower alkyl, lower alkoxy or phenyl, wherein the phenyl is optionally substituted by halogen, lower alkyl, or —S(O)$_2$-lower alkyl,
R$^{11}$ is hydrogen or lower alkyl,
R$^{12}$ is hydrogen or lower alkyl,
X is a) N and Y is C—R$^{10}$,
  b) C—R$^9$ and Y is N, or
  c) C—R$^9$ and Y is C—R$^{10}$, and
n is 0 or 1;
with the proviso that R$^8$ is lower alkyl, when
a) R$^1$ is hydrogen, R$^2$ is hydrogen, R$^3$ is halogen, R$^4$ is halogen, R$^6$ is hydrogen, R$^7$ is hydrogen, R$^9$ is hydrogen, R$^{10}$ is halogen, n is 0, X is C—R$^9$ and Y is C—R$^{10}$;
b) R$^1$ is hydrogen, R$^2$ is hydrogen, R$^3$ is lower alkoxy, R$^4$ is lower alkoxy, R$^6$ is hydrogen, R$^7$ is hydrogen, R$^9$ is hydrogen, R$^{10}$ is halogen, n is 0, X is C—R$^9$ and Y is C—R$^{10}$;
c) R$^1$ is hydrogen, R$^2$ is hydrogen, R$^3$ is halogen, R$^4$ is heterocyclyl, R$^6$ is hydrogen, R$^7$ is hydrogen, R$^9$ is hydrogen, R$^{10}$ is hydrogen, n is 0, X is C—R$^9$ and Y is C—R$^{10}$;
d) R$^1$ is hydrogen, R$^2$ is hydrogen, R$^3$ is halogen, R$^4$ is hydrogen, n is O, R$^6$ is hydrogen, R$^7$ is hydrogen, R$^9$ is halogen, R$^{10}$ is hydrogen, X is C—R$^9$ and Y is C—R$^{10}$;
e) R$^1$ is hydrogen, R$^2$ is hydrogen, R$^3$ is halogen, R$^4$ is hydrogen, R$^6$ is lower alkyl, R$^7$ is hydrogen, R$^9$ is hydrogen, n is 0, X is C—R$^9$ and Y is N; or
R$^1$ is hydrogen, R$^2$ is hydrogen, R$^3$ is halogen, R$^4$ is hydrogen, R$^6$ is lower alkyl, R$^7$ is hydrogen, R$^{10}$ is hydrogen, n is 0, X is N and Y is C—R$^{10}$;
or pharmaceutically active salts or esters thereof.

Furthermore, the invention provides compounds of formula I as depicted above wherein
R$^1$ is hydrogen, halogen or lower alkyl,
R$^2$ is hydrogen, halogen or lower alkyl,
R$^3$ is halogen or lower alkyl, which lower alkyl is optionally substituted by halogen,
R$^4$ is a) lower alkyl, optionally substituted by halogen or lower alkoxy,
  b) lower alkoxy, optionally substituted by halogen, hydroxyl, cycloalkyl or heterocyclyl,
  c) —Si(lower alkyl)$_3$,
  d) —O-cycloalkyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  e) —O-aryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  f) —O-heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  g) —O-heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  wherein each S being part of a heterocyclyl is optionally substituted by oxo,
  h) heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  i) aryl, substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  j) heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  and R$^4$ is hydrogen when R$^{10}$ is phenyl, wherein the phenyl is optionally substituted by halogen, lower alkyl, or —S(O)$_2$-lower alkyl, and R$^4$ is aryl when R$^6$ is lower alkyl,
R$^5$ is halogen or lower alkyl,
R$^6$ is hydrogen or lower alkyl,
R$^7$ is hydrogen or lower alkyl,
R$^8$ is hydrogen or lower alkyl,
R$^9$ is hydrogen, halogen, lower alkyl or lower alkoxy,
R$^{10}$ is hydrogen, halogen, lower alkyl or lower alkoxy,
R$^{11}$ is hydrogen or lower alkyl,
R$^{12}$ is hydrogen or lower alkyl,
X is a) N and Y is C—R$^{10}$,
  b) C—R$^9$ and Y is N, or
  c) C—R$^9$ and Y is C—R$^{10}$,
n is 0 or 1, with the proviso that $R^8$ is lower alkyl, when
a) $R^1$ is hydrogen, $R^2$ is hydrogen, $R^3$ is methyl, $R^4$ is methyl, $R^6$ is hydrogen, $R^7$ is hydrogen, $R^9$ is hydrogen, $R^{10}$ is hydrogen, n is 0, X is C—$R^9$ and Y is C—$R^{10}$;
b) $R^1$ is hydrogen, $R^2$ is hydrogen, $R^3$ is methyl, $R^4$ is methyl, $R^6$ is hydrogen, $R^7$ is ethyl, $R^9$ is methyl, $R^{10}$ is hydrogen, n is 0, X is C—$R^9$ and Y is C—$R^{10}$;
c) $R^1$ is hydrogen, $R^2$ is hydrogen, $R^3$ is t-butyl, $R^4$ is t-butyl, $R^6$ is hydrogen, $R^7$ is hydrogen, $R^9$ is hydrogen, $R^{10}$ is hydrogen, n is 0, X is C—$R^9$ and Y is C—$R^{10}$;
d) $R^1$ is hydrogen, $R^2$ is hydrogen, $R^3$ is chloro, $R^4$ is hydrogen, $R^6$ is hydrogen, $R^7$ is hydrogen, $R^9$ is hydrogen, $R^{10}$ is hydrogen, n is 0, X is C—$R^9$ and Y is C—$R^{10}$;
e) $R^1$ is hydrogen, $R^2$ is hydrogen, $R^3$ is chloro, $R^4$ is morpholino, $R^6$ is hydrogen, $R^7$ is hydrogen, $R^9$ is hydrogen, $R^{10}$ is hydrogen, n is 0, X is C—$R^9$ and Y is C—$R^{10}$;
f) $R^1$ is hydrogen, $R^2$ is hydrogen, $R^3$ is chloro, $R^4$ is hydrogen, $R^6$ is hydrogen, $R^7$ is hydrogen, $R^9$ is chloro, $R^{10}$ is hydrogen, n is 0, X is C—$R^9$ and Y is C—$R^{10}$;
g) $R^1$ is hydrogen, $R^2$ is hydrogen, $R^3$ is chloro, $R^4$ is hydrogen, $R^6$ is methyl, $R^7$ is hydrogen, $R^9$ is hydrogen, n is 0, X is C—$R^9$ and Y is N; or
h) $R^1$ is hydrogen, $R^2$ is hydrogen, $R^3$ is chloro, $R^4$ is hydrogen, $R^6$ is methyl, $R^7$ is hydrogen, $R^{10}$ is hydrogen, n is 0, X is N and Y is C—$R^{10}$;

or pharmaceutically active salts or esters thereof.

The present invention provides compounds of formula I per se, pharmaceutical compositions containing them and their use in the treatment of neurological and neuropsychiatric disorders.

Compounds of formula I are good inhibitors of the glycine transporter 1 (GlyT-1) and have a good selectivity to glycine transporter 2 (GlyT-2) inhibitors. Thus, compounds of the invention are useful for the treatment of diseases related to activation of NMDA receptors via GlyT-1 inhibition, for example, the control or prevention of illnesses such as psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

Furthermore, the invention includes all racemic mixtures, all their corresponding enantiomers, optical isomers and/or tautomers as well as their hydrates, solvates and isotopically-labelled analogues.

DETAILED DESCRIPTION OF THE INVENTION

Unless otherwise stated, the following terms used in the present application, including the specification and claims, have the definitions given below. It must be noted that, as used in the specification and the appended claims, the singular forms "a", "an", and "the" include plural referents unless the context clearly dictates otherwise.

The term "substituted" means that the specified group or moiety can bear 1, 2, 3, 4, 5 or 6 substituents. Where any group can carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents, independently chosen from the group of possible substituents. The term "optionally substituted ring" means a ring, which can individually bear substituents at each of the ring atoms.

The term "lower alkyl" stands for a hydrocarbon radical which can be linear or branched, with single or multiple branching, whereby the alkyl group in general comprises 1 to 6 carbon atoms, for example, methyl (Me), ethyl (Et), propyl, isopropyl, n-butyl, i-butyl (iso-butyl), 2-butyl (sec-butyl), t-butyl (tert-butyl), isopentyl and the like. Preferred alkyl groups are groups with 1-4 carbon atoms. Most preferred are methyl, ethyl, propyl, isopropyl and t-butyl.

The terms "halogen-lower alkyl" and "lower alkyl substituted by halogen" refer lower alkyl groups in which one or more hydrogen atom has been replaced by a halogen atom; for example: $CF_3$, $CHF_2$, $CH_2F$, $CH_2CF_3$, $CH_2CH_2CF_3$, $CHF_2CF_2$, and the like. Preferred groups are $CF_3$—, $CHF_2CF_2$— and $CF_3CH_2CH_2$—.

The term "lower alkoxy-lower alkyl" refers to a lower alkyl group in which one or more hydrogen atom has been replaced with a lower alkoxy group as defined herein; for example: MeO-Me-, EtO-Me, MeO-Et, and the like. Preferred group is MeO-Me-.

The term "lower alkoxy" stands for a "—O-alkyl" radical which can be linear or branched, with single or multiple branching, whereby the alkyl group in general comprises 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Preferred alkoxy groups are groups with 1 to 5 carbon atoms. Most preferred are methoxy, ethoxy, propoxy, isopropoxy, n-butoxy and isopentyloxy.

The term "halogen-lower alkoxy" refers a lower alkoxy group as defined above in which one or more hydrogen atom is replaced by a halogen atom; for example: tetrafluoro-ethoxy, difluoro-ethoxy, difluoro-propoxy, difluoro-isopropoxy, pentafluoro-propoxy-, trifluoro-isopropoxy-, trifluoro-ethoxy-, trifluoro-propoxy-, and the like. Preferred groups are tetrafluoro-ethoxy, difluoro-isopropoxy, pentafluoro-propoxy-, trifluoro-isopropoxy, trifluoro-ethoxy-, and trifluoro-propoxy-.

The term "halogen" denotes chlorine (Cl), iodine (I), fluorine (F) and bromine (Br). Preferred halogens are fluorine and chlorine.

The term "aryl" refers to an aromatic carbocyclic group comprising 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred aryl group is phenyl.

The term "substituted aryl" refers to an aryl group which is substituted by one or multiple substituents, whereby substitution at each ring atom individually is possible, selected from halogen, amido, nitro, acetyl, acetamidyl, lower alkyl wherein the lower alkyl is optionally substituted by halogen or lower alkoxy, lower alkoxy wherein the lower alkoxy is optionally substituted by halogen, lower alkyl, or —NRR', and —S(O)$_2$-lower alkyl. Preferred substituents are F, Cl, Me, $CF_3$, trifluoro-MeO-, MeO, Me-S(O)$_2$, acetamidyl, isopropoxy, F-isopropoxy, Me$_2$N, nitro or amido. Preferred "substituted aryl" are MeO-Ph-, Me-S(O)$_2$-Ph-, acetamidyl-Ph-, isopropoxy-Ph-, F-isopropoxy-Ph-, F-Ph-, Cl-Ph-, Me-Ph-, trifluoro-MeO-Ph-, CF$_3$-Ph-, Me$_2$N-Ph-, nitro-Ph- or amido-Ph-.

The term "oxo" refers to the group =O.
The term "hydroxy" refers to the group —OH.

The term "amido" refers to the group —(C=O)—NRR', where R and R' are residues as particularly defined herein, and can independently be hydrogen or optionally substituted alkyl. In the preferred amido group residues R and R' are hydrogen.

The term "heteroaryl" refers to an aromatic group having a single 4 to 8 membered ring or multiple condensed rings comprising 6 to 14, more preferably 6 to 10, ring atoms and containing at least one heteroatom selected from N, O and S. Within at least one ring, the number of N atoms is 0, 1, 2 or 3, and the number of O and S atoms are each 0, 1 or 2; in which group at least one heterocyclic ring is aromatic. Examples of such groups include pyrrolyl, thienyl, furyl, pyrazolyl, imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. Preferred heteroaryl groups are pyridinyl, pyrimidinyl, thienyl and thiazolyl.

The term "substituted heteroaryl" refers to a heteroaryl which is substituted by one or multiple substituents, whereby substitution at each ring atom individually is possible, selected from halogen, amido, nitro, acetyl, acetamidyl, lower alkyl wherein the lower alkyl is optionally substituted by halogen or lower alkoxy, lower alkoxy wherein the lower alkoxy is optionally substituted by halogen, lower alkyl, or —NRR', and —S(O)$_2$-lower alkyl. Preferred substituents are F, Me, MeO, H$_2$N, acetyl and Me-S(O)$_2$. Preferred "substituted heteroaryl" are F-pyridinyl, MeO-pyridinyl, H$_2$N-pyridinyl, Me-S(O)$_2$-pyridinyl, and dimethyl-thiazolyl.

The terms "cycloheteroalkyl" or "heterocyclyl" refer to a 4 to 8-membered heterocyclic ring containing at least one heteroatom, such as N, O or S, the number of N atoms being 0, 1, 2 or 3, and the number of O and S atoms each being 0, 1 or 2, which system can be saturated, partly unsaturated or dihydroaromatic, and which ring can be part of a multiple condensed ring-system. Examples of such cycloheteroalkyl groups include pyrrolidinyl, tetrahydrofuryl, tetrahydrothienyl, tetrahydropyridinyl, tetrahydropyryl, azetidinyl, thiazolidinyl, oxazolidinyl, piperidinyl, morpholinyl, thiomorpholinyl, piperazinyl, azepanyl, diazepanyl, oxazepanyl and the like. Preferred cycloheteroalkyl groups are morpholinyl, oxazepanyl, tetrahydrofuryl and tetrahydropyryl.

The term "substituted cycloheteroalkyl" refers to a cycloheteroalkyl which is substituted by one or multiple substituents, whereby substitution at each ring atom individually is possible, selected from halogen, amido, nitro, acetyl, acetamidyl, lower alkyl wherein the lower alkyl is optionally substituted by halogen or lower alkoxy, lower alkoxy wherein the lower alkoxy is optionally substituted by halogen, lower alkyl, or —NRR', and —S(O)$_2$-lower alkyl. Preferred substituents are acetyl, or dioxo at an S atom when an S atom is part of a heterocyclic ring. Preferred "substituted cycloheteroalkyl" are acetyl-piperidinyl or dioxo-tetrahydrothiopyranyl.

The term "cycloalkyl" refers to a 3 to 8 membered carbon ring, for example cyclopropyl, cyclobutyl, cyclopentyl, cyclohexyl, cycloheptyl or cyclooctyl. Preferred cycloalkyl groups are cyclopropyl, cyclopentyl and cyclohexyl.

The following R$^4$ substituents can have the structures as depicted in Table 1 below.

TABLE 1 chemical structures of possible R$^4$ moieties

| Substituent | Structure |
|---|---|
| tetrahydrofuran-ethoxy- | 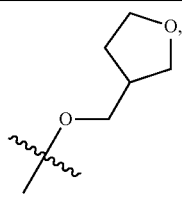 |
| | 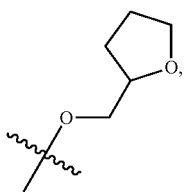 [SMILES: *OCC1CCCO1] |
| | preferred is 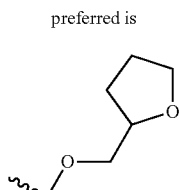 |
| tetrahydropyran-ethoxy- | 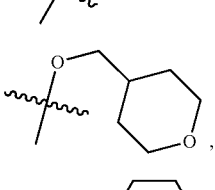 |
| | 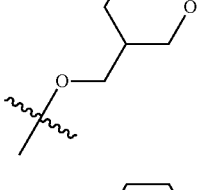 |
| | 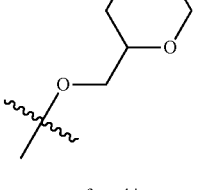 |
| | preferred is 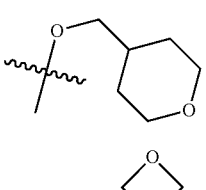 |
| oxetanyl-propoxy- | 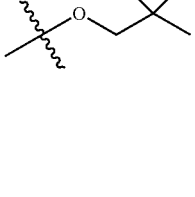 |

TABLE 1-continued chemical structures of possible R⁴ moieties

| Substituent | Structure |
|---|---|
| | 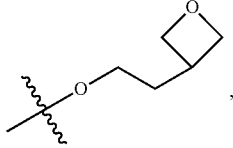 [SMILES: *OCCC1COC1] |
| | preferred is |
| | 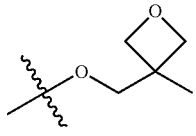 [SMILES: *OCC1(C)COC1] |
| cyclopropyl-ethoxy- | 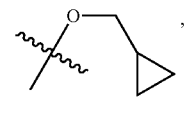 |
| | 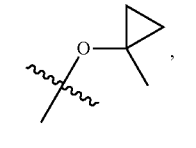 |
| | preferred is |
| | 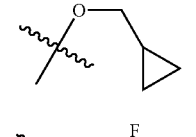 |
| tetrafluoro-ethoxy | 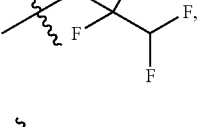 |
| | 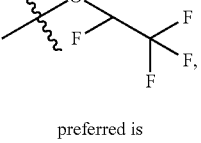 |
| | preferred is |
| | 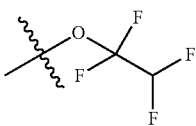 [SMILES: *OC(F)(F)C(F)F] |
| trifluoro-ethoxy | 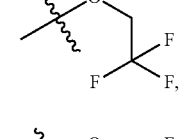 |
| | 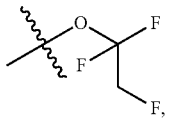 [SMILES: *OC(F)(F)CF] |

TABLE 1-continued chemical structures of possible R⁴ moieties

| Substituent | Structure |
|---|---|
| | 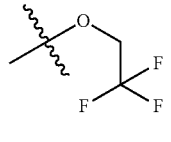 [SMILES: *OCC(F)(F)F] |
| | preferred is |
| | (structures continue) |
| trifluoro-isopropoxy | 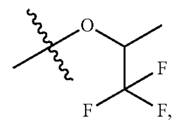 [SMILES: *OC(C)C(F)(F)F] |
| difluoro-isopropoxy | 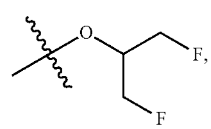 [SMILES: *OC(CF)CF] |
| | preferred is |

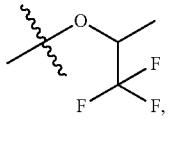

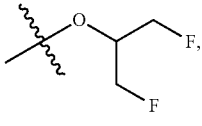

TABLE 1-continued chemical structures of possible R⁴ moieties

| Substituent | Structure |
|---|---|
| Cl,OH-isopentyloxy | (structure with O, H₃C, OH, Cl) |
| | (structure with O, Cl, H₃C, OH) |
| | (structure with O, OH, H₃C, Cl) |
| preferred is | (structure with O, H₃C, OH, Cl) |
| trifluoro-propoxy | (structure with O, F, F, F) |
| | (structure with O, F, F, F) |
| | (structure with O, F, F, F) |
| | (structure with O, F, F, F) |

TABLE 1-continued chemical structures of possible R⁴ moieties

| Substituent | Structure |
|---|---|
| | (structure with O, F, F, F) |
| | (structure with O, F, F, F) |
| | (structure with O, F, F, F) |
| preferred is | (structure with O, F, F, F) |
| pentafluoro-propoxy | (structure with O, F, F, F, F, F) |
| | (structure with O, F, F, F, F, F) |
| | (structure with O, F, F, F, F, F) |

TABLE 1-continued chemical structures of possible R⁴ moieties

| Substituent | Structure |
|---|---|
| | preferred is |
| | (structure: O-CH2-C(F)(CF3)-CF3 type, pentafluoro) |
| Cl,OH-butoxy | (O-CH2-CH(OH)-CH2-CH2-Cl) |
| | (O-CH2-CH2-CH(OH)-CH2-Cl) |
| | (O-CH2-CH2-CH2-CH(OH)-Cl) |
| | (O-CH(OH)-CH2-CH2-CH2-Cl) |
| | (O-CH2-CH2-CH(Cl)-CH2-OH) |
| | (O-CH2-CH2-C(Cl)(OH)-CH3) |
| | (O-CH2-CH(OH)-CH(Cl)-CH3) |
| | (O-CH(OH)-CH2-CH(Cl)-CH3) |
| | (O-CH2-CH(Cl)-CH2-OH, with extra) |
| | (O-CH2-CH(Cl)-CH(OH)-CH3) |

TABLE 1-continued chemical structures of possible R⁴ moieties

| Substituent | Structure |
|---|---|
| | (O-CH2-C(Cl)(OH)-CH2-CH3) |
| | (O-CH(Cl)-CH2-CH3 with OH) |
| | (O-CH(Cl)-CH(OH)-CH2-CH3) |
| | (O-C(OH)(Cl)-CH2-CH2-CH3) |
| | (O-CH(Cl)-CH2-CH(OH)-CH3) |
| | (O-CH(Cl)-CH2-CH2-CH2-OH) |
| | preferred is |
| | (O-CH2-CH(OH)-CH2-CH2-Cl) |
| MeO—Ph— | (p-methoxyphenyl) |
| | (m-methoxyphenyl) |
| | (o-methoxyphenyl) |

TABLE 1-continued
chemical structures of possible R⁴ moieties
| Substituent | Structure |
|---|---|
| | preferred is 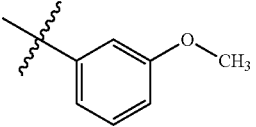 [SMILES: *c1cccc(OC)c1] |
| Me—S(O)₂—Ph— | 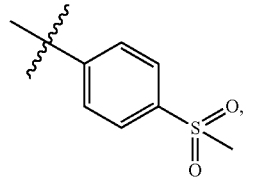 [SMILES: *c1ccc(S(C)(=O)=O)cc1] |
| | 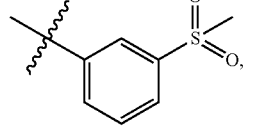 |
| | 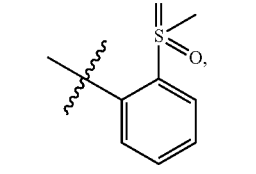 |
| | preferred is 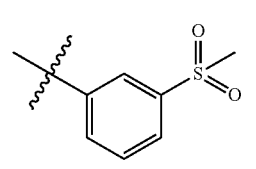 [SMILES: *c1cccc(S(C)(=O)=O)c1] |
| acetamidyl-Ph— | 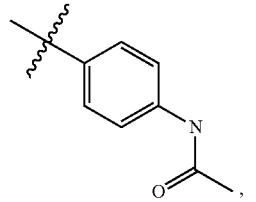 [SMILES: *c1ccc(NC(C)=O)cc1] |
| | 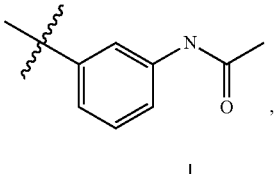 |
| | 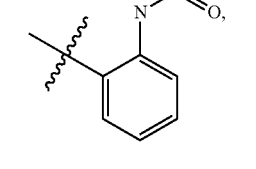 |
TABLE 1-continued
chemical structures of possible R⁴ moieties
| Substituent | Structure |
|---|---|
| | preferred is  |
| isopropoxy-Ph— |  |
| |  |
| |  |
| | preferred is 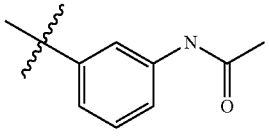 [SMILES: *c1cccc(NC(C)=O)c1] |
| isopropoxy,F—Ph— | 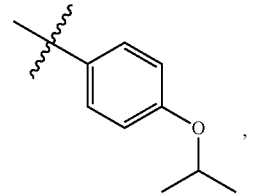 [SMILES: *c1ccc(OC(C)C)cc1] |
| | 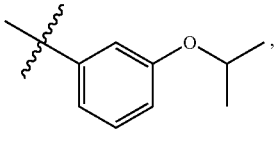 [SMILES: *c1cccc(OC(C)C)c1] |
| | 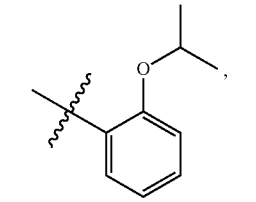 [SMILES: *c1ccccc1OC(C)C] |

TABLE 1-continued
chemical structures of possible R⁴ moieties
| Substituent | Structure |
|---|---|
| | 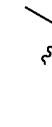 |
| |  |
| |  |
| |  |
| |  |
| |  |
| |  |
TABLE 1-continued
chemical structures of possible R⁴ moieties
| Substituent | Structure |
|---|---|
| | preferred is |
| |  |
| F—Ph— | , ,  |
| | preferred is |
| |  |
| Cl—Ph— | , ,  |
| | preferred are |
| |  |

TABLE 1-continued chemical structures of possible R⁴ moieties

| Substituent | Structure |
|---|---|
| Me—Ph— | and [2-chlorophenyl]; [4-methylphenyl]; [3-methylphenyl]; [2-methylphenyl], preferred are [3-methylphenyl] and [2-methylphenyl] |
| trifluoro-MeO—Ph | [4-OCF₃-phenyl]; [3-OCF₃-phenyl], |

TABLE 1-continued chemical structures of possible R⁴ moieties

| Substituent | Structure |
|---|---|
| | [2-OCF₃-phenyl], preferred is [3-OCF₃-phenyl] |
| CF₃—Ph | [4-CF₃-phenyl]; [3-CF₃-phenyl]; [2-CF₃-phenyl], preferred is [3-CF₃-phenyl] |
| N(Me)₂—Ph— | [4-N(Me)₂-phenyl]; [3-N(Me)₂-phenyl], |

TABLE 1-continued chemical structures of possible R⁴ moieties

| Substituent | Structure |
|---|---|
| | H₃C-N-CH₃ phenyl structure |
| | preferred is |
| | 3-dimethylamino-phenyl structure |
| nitro-Ph— | 4-nitrophenyl structure |
| | 3-nitrophenyl structure |
| | 2-nitrophenyl structure |
| | preferred is |
| | 3-nitrophenyl structure |
| amido-Ph | 4-carboxamidophenyl structure |
| | 3-carboxamidophenyl structure |

TABLE 1-continued chemical structures of possible R⁴ moieties

| Substituent | Structure |
|---|---|
| | 2-carboxamidophenyl structure |
| | preferred is |
| | 3-carboxamidophenyl structure |
| F-pyrimidyl | 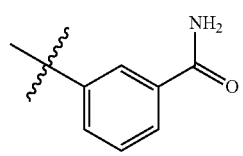 [SMILES: *c1cccc(C(N)=O)c1] |
| | 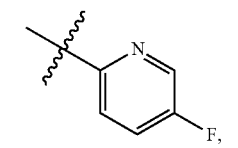 |
| | 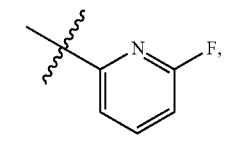 [SMILES: *c1cccc(F)n1] |
| | 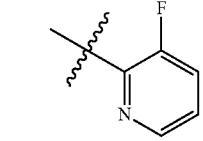 [SMILES: *c1ncccc1F] |
| | 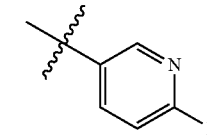 |
| | 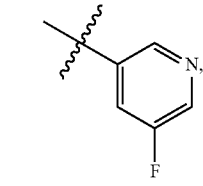 [SMILES: *c1cncc(F)c1] |
| | 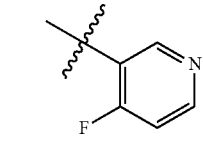 |
| | 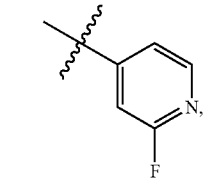 [SMILES: *c1ccnc(F)c1] |

TABLE 1-continued chemical structures of possible R⁴ moieties

| Substituent | Structure |
|---|---|
| | 3-fluoro-4-pyridinyl |
| | preferred is |
| | 5-fluoro-3-pyridinyl |
| OMe-pyridinyl | 5-methoxy-2-pyridinyl |
| | 6-methoxy-2-pyridinyl |
| | 3-methoxy-2-pyridinyl |
| | 6-methoxy-3-pyridinyl |
| | 5-methoxy-3-pyridinyl |
| | 4-methoxy-3-pyridinyl |

TABLE 1-continued chemical structures of possible R⁴ moieties

| Substituent | Structure |
|---|---|
| | 2-methoxy-4-pyridinyl |
| | 3-methoxy-4-pyridinyl |
| | preferred are |
| | 5-methoxy-3-pyridinyl |
| | and |
| | 6-methoxy-3-pyridinyl |
| NH₂-pyridinyl | 5-amino-2-pyridinyl |
| | 6-amino-2-pyridinyl |
| | 3-amino-2-pyridinyl |
| | 6-amino-3-pyridinyl |

TABLE 1-continued chemical structures of possible R⁴ moieties

| Substituent | Structure |
|---|---|
| | [3-aminopyridin-5-yl] |
| | [4-aminopyridin-3-yl] |
| | [2-aminopyridin-4-yl] |
| | [3-aminopyridin-4-yl] |
| preferred is | |
| | [6-aminopyridin-3-yl] |
| Me—SO₂-pyridinyl | [5-(methylsulfonyl)pyridin-3-yl] |
| | [5-(methylsulfonyl)pyridin-2-yl] |
| preferred is | |
| | [5-(methylsulfonyl)pyridin-3-yl] |

TABLE 1-continued chemical structures of possible R⁴ moieties

| Substituent | Structure |
|---|---|
| tetrahydrofuran-O— | [tetrahydrofuran-3-yloxy] |
| | [tetrahydrofuran-2-yloxy] |
| preferred is | |
| | [tetrahydrofuran-3-yloxy] |
| tetrahydropyran-O— | [tetrahydropyran-4-yloxy] |
| | [tetrahydropyran-3-yloxy] |
| | [tetrahydropyran-2-yloxy] |
| preferred are | |
| | [tetrahydropyran-3-yloxy] |

TABLE 1-continued chemical structures of possible R⁴ moieties

| Substituent | Structure |
|---|---|
| | and (O-tetrahydropyran structure) |
| SiMe₃— | Si(CH₃)₃ |
| —O-tetrahydrothiopyran dioxide | (O-tetrahydrothiopyran-4-yl 1,1-dioxide); (3-yl 1,1-dioxide); (2-yl 1,1-dioxide) |
| | preferred is (O-tetrahydrothiopyran-4-yl 1,1-dioxide) |
| acetyl-piperidin-O— | (O-piperidin-4-yl N-acetyl) |

TABLE 1-continued chemical structures of possible R⁴ moieties

| Substituent | Structure |
|---|---|
| | (O-piperidin-3-yl N-acetyl), (O-piperidin-2-yl N-acetyl) |
| | preferred is (O-piperidin-4-yl N-acetyl) |
| cyclopentyl-O— | (O-cyclopentyl) |
| cyclohexyl-O— | (O-cyclohexyl) |
| OMe—Me—Ph— | (4-methoxymethyl-phenyl), (3-methoxymethyl-phenyl) |

TABLE 1-continued
chemical structures of possible R⁴ moieties
| Substituent | Structure |
|---|---|
| | 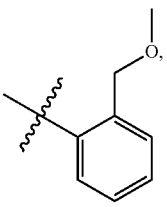 [SMILES: *c1ccccc1COC] |
| | preferred is |
| | 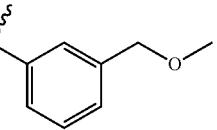 |
| dimethyl-thiazolyl- | 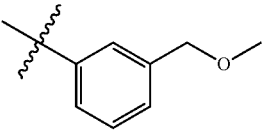 [SMILES: *c1cccc(COC)c1] |
| | 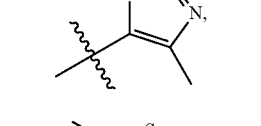 |
| | preferred is |
| | 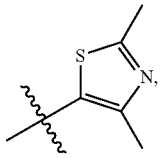 [SMILES: *c1sc(C)nc1C] |
| Ph—O— | 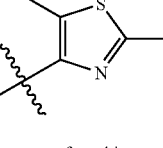 |
| pyrimidinyl- | 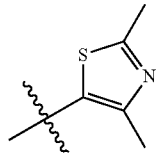 [SMILES: *c1sc(C)nc1C] |
| | 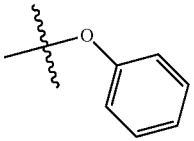 [SMILES: *Oc1ccccc1] |
| | preferred is |
| | 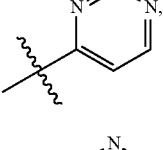 |
TABLE 1-continued
chemical structures of possible R⁴ moieties
| Substituent | Structure |
|---|---|
| thienyl- | 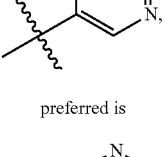 |
| | 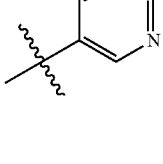 |
| | preferred is |
| |  |
| morpholino- | 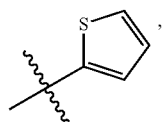 [SMILES: *c1cccs1] |
| | 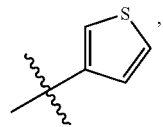 [SMILES: *c1ccsc1] |
| | 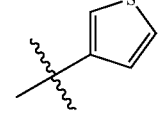 |
| | preferred is |
| | 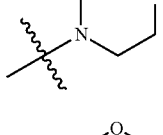 |
| pyridinyl- | 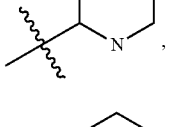 |
| | 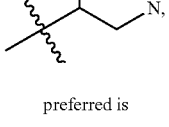 |
| | 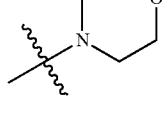 |

TABLE 1-continued chemical structures of possible R⁴ moieties

| Substituent | Structure |
|---|---| preferred are

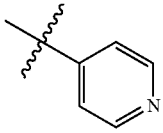 [SMILES: *c1ccncc1]

and

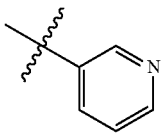 [SMILES: *c1cccnc1]

The term "pharmaceutically acceptable salts" refer to salts of a compound of formula I that are, suitable for use in contact with the tissues of humans and lower animals without undue toxicity, irritation, allergic response, and the like, and are commensurate with a reasonable benefit-risk ratio. Examples of suitable salts with inorganic and organic acids are, but are not limited to, hydrochloric acid, nitric acid, sulfuric acid, phosphoric acid, sulfuric acid, citric acid, formic acid, fumaric acid, maleic acid, lactic acid, malic acid, acetic acid, succinic acid, tartaric acid, methane-sulfonic acid, p-toluene-sulfonic acid, trifluoroacetic acid and the like. Preferred acids are hydrochloric acid and trifluoroacetic acid.

The term "pharmaceutically acceptable esters" refer to a conventionally esterified compound having a carboxyl group, which esters retain the biological effectiveness and properties of the respective compounds of formula I and are cleaved in vivo (in the organism) to the corresponding active carboxylic acid. Examples of ester groups which are cleaved (in this case hydrolyzed) in vivo to the corresponding carboxylic acids are those in which the cleaved hydrogen is replaced with-lower alkyl which is optionally substituted with heterocycle, cycloalkyl, etc. Examples of substituted lower alkyl esters are those in which-lower alkyl is substituted with pyrrolidine, piperidine, morpholine, N-methylpiperazine, etc. Furthermore, the term "pharmaceutically acceptable esters" refer to a conventionally esterified compound having a hydroxy group, which esters retain the biological effectiveness and properties of the respective compounds of formula I and are cleaved in vivo (in the organism) to the corresponding compound of formula I. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which acids are non-toxic to living organisms.

The conversion into pharmaceutically acceptable esters of compounds of formula I bearing a carboxy group can be carried out e.g. by treatment of a suitable carboxy group with a suitable alcohol using e.g. a condensating reagent such as benzotriazol-1-yloxytris(dimethylamino)phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulfuric acid and the like. The conversion into pharmaceutically acceptable esters of compounds of formula I bearing a hydroxy group can be carried out with suitable acids by analogous methods.

The term "solvates" refers to a complex of the respective compound that contains either stoichiometric or non-stoichiometric amounts of a solvent, which have been included with a defined molar ratio in the structure. Such solvents for the purpose of the invention may not interfere with the biological activity of the solute. "Solvates" are called "hydrates" in case the included solvent is water. The compound of formula I and pharmaceutically acceptable salts thereof can exist in the form of a hydrate or a solvate, and such a hydrate and solvate are also encompassed in the present invention. Examples thereof include hydrate, dihydrochloride dihydrate, and the like.

The word "comprise" and variations of the word, such as "comprising" and "comprises" is not intended to exclude other additives, components, integers or steps.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

The term "mammal" refers to any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. Preferred mammals are humans.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers, and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates, which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, the term "optically pure enantiomer" means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

Isotopically-labelled compound of formula I, including compounds of formula I isotopically-labelled to be detectable by PET or SPECT, also fall within the scope of the invention. The same applies to compounds of formula I labelled with [$^{13}$C]—, [$^{14}$C]—, [$^{3}$H]—, [$^{18}$F]—, [$^{125}$I]— or other isotopically enriched atoms, suitable for receptor binding or metabolism studies.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. Examples of suitable amino protecting groups are, but not limited to, listed below. The preferred amino protecting group is BOC.

TABLE 2 structures of possible N-protecting groups

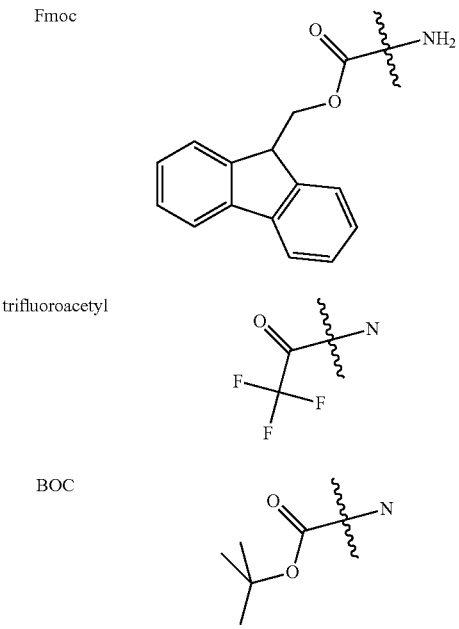

TABLE 2-continued structures of possible N-protecting groups

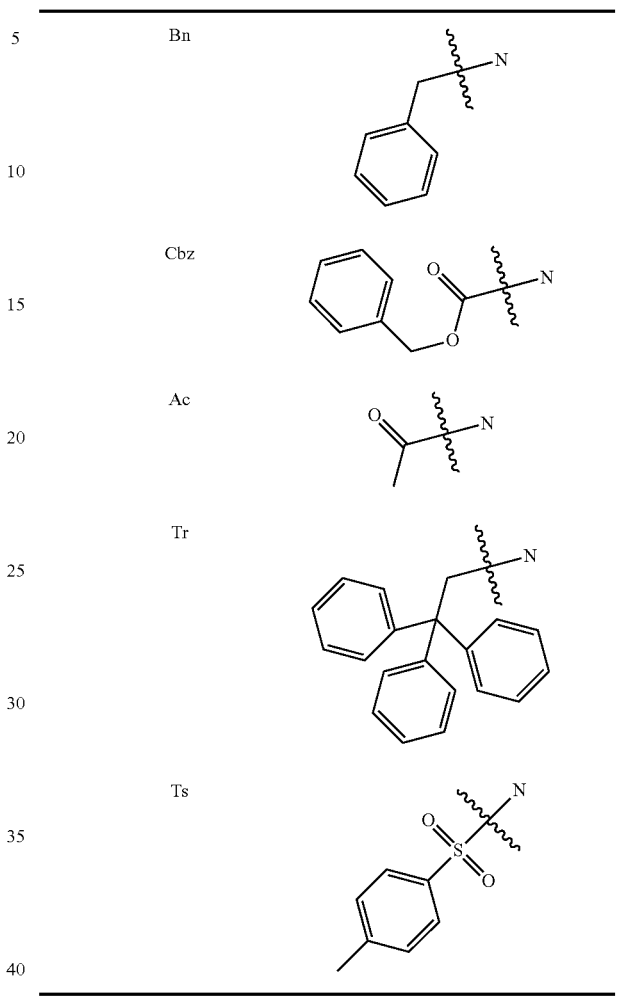

One embodiment of the invention is a method for the treatment of psychoses, dysfunction in memory and learning, schizophrenia, dementia, attention deficit disorder, or Alzheimer's disease which comprises administering a compound of formula I

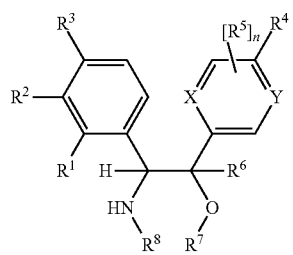

wherein $R^1$ is hydrogen, halogen, lower alkyl, or lower alkoxy, $R^2$ is hydrogen, halogen, lower alkyl, or lower alkoxy, $R^3$ is hydrogen, halogen, lower alkoxy or lower alkyl, wherein the lower alkyl is optionally substituted by halogen, R⁴ is a) hydrogen,
b) halogen,
c) lower alkyl, optionally substituted by halogen, lower alkoxy or hydroxyl,
d) lower alkoxy, optionally substituted by halogen, hydroxyl, cycloalkyl or heterocyclyl,
e) —NR¹¹R¹²
f) —S(O)₂-lower alkyl,
g) —Si(lower alkyl)₃,
h) —O-cycloalkyl,
i) —O-aryl,
j) —O-heteroaryl,
k) —O-heterocyclyl,
l) aryl,
m) heteroaryl, or
n) heterocyclyl,
wherein each of the cycloalkyl, aryl, heteroaryl and heterocyclyl is optionally substituted by halogen, amido, nitro, acetyl, acetamidyl, lower alkyl, halogen-lower alkyl, lower alkoxy-lower alkyl, —NR¹¹R¹², lower alkoxy, halogen-lower alkoxy, or —S(O)₂-lower alkyl,
and wherein each S being part of a heterocyclyl is optionally substituted by oxo,
R⁵ is halogen, lower alkyl, or lower alkoxy,
R⁶ is hydrogen or lower alkyl,
R⁷ is hydrogen or lower alkyl,
R⁸ is hydrogen or lower alkyl,
R⁹ is hydrogen, halogen, lower alkyl, or lower alkoxy,
R¹⁰ is hydrogen, halogen, lower alkyl, lower alkoxy or phenyl, wherein the phenyl is optionally substituted by halogen, lower alkyl, or —S(O)₂-lower alkyl,
R¹¹ is hydrogen or lower alkyl,
R¹² is hydrogen or lower alkyl,
X is a) N and Y is C—R¹⁰,
b) C—R⁹ and Y is N, or
c) C—R⁹ and Y is C—R¹⁰, and
n is 0 or 1;
with the proviso that R⁸ is lower alkyl, when
a) R¹ is hydrogen, R² is hydrogen, R³ is halogen, R⁴ is halogen, R⁶ is hydrogen, R⁷ is hydrogen, R⁹ is hydrogen, R¹⁰ is halogen, n is 0, X is C—R⁹ and Y is C—R¹⁰;
b) R¹ is hydrogen, R² is hydrogen, R³ is lower alkoxy, R⁴ is lower alkoxy, R⁶ is hydrogen, R⁷ is hydrogen, R⁹ is hydrogen, R¹⁰ is halogen, n is 0, X is C—R⁹ and Y is C—R¹⁰;
c) R¹ is hydrogen, R² is hydrogen, R³ is halogen, R⁴ is heterocyclyl, R⁶ is hydrogen, R⁷ is hydrogen, R⁹ is hydrogen, R¹⁰ is hydrogen, n is 0, X is C—R⁹ and Y is C—R¹⁰;
d) R¹ is hydrogen, R² is hydrogen, R³ is halogen, R⁴ is hydrogen, R⁶ is hydrogen, R⁷ is hydrogen, R⁹ is halogen, R¹⁰ is hydrogen, X is C—R⁹ and Y is C—R¹⁰;
e) R¹ is hydrogen, R² is hydrogen, R³ is halogen, R⁴ is hydrogen, R⁶ is lower alkyl, R⁷ is hydrogen, R⁹ is hydrogen, n is 0, X is C—R⁹ and Y is N; or
f) R¹ is hydrogen, R² is hydrogen, R³ is halogen, R⁴ is hydrogen, R⁶ is lower alkyl, R⁷ is hydrogen, R¹⁰ is hydrogen, n is 0, X is N and Y is C—R¹⁰;
or pharmaceutically active salts or esters thereof.

One further embodiment of the invention provides compounds of formula I as described herein

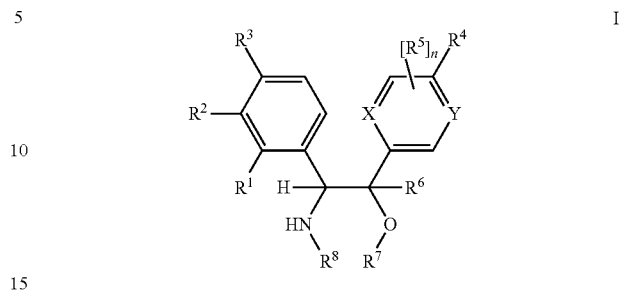

wherein
R¹ is hydrogen, halogen or lower alkyl,
R² is hydrogen, halogen or lower alkyl,
R³ is halogen or lower alkyl, which lower alkyl is optionally substituted by halogen,
R⁴ is a) lower alkyl, optionally substituted by halogen or lower alkoxy,
b) lower alkoxy, optionally substituted by halogen, hydroxyl, cycloalkyl or heterocyclyl,
c) —Si(lower alkyl)₃,
d) —O-cycloalkyl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
e) —O-aryl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
f) —O-heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
g) —O-heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
wherein each S being part of a heterocyclyl is optionally substituted by oxo,
h) heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
i) aryl, substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl, or
j) heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR¹¹R¹², or —S(O)₂-lower alkyl,
and R⁴ is hydrogen when R¹⁰ is phenyl, wherein the phenyl is optionally substituted by halogen, lower alkyl, or —S(O)₂-lower alkyl,
and R⁴ is aryl when R⁶ is lower alkyl,
R⁵ is halogen or lower alkyl,
R⁶ is hydrogen or lower alkyl,
R⁷ is hydrogen or lower alkyl,
R⁸ is hydrogen or lower alkyl, $R^9$ is hydrogen, halogen, lower alkyl or lower alkoxy,
$R^{10}$ is hydrogen, halogen, lower alkyl or lower alkoxy,
$R^{11}$ is hydrogen or lower alkyl,
$R^{12}$ is hydrogen or lower alkyl, and
X is a) N and Y is C—$R^{10}$,
  b) C—$R^9$ and Y is N, or
  c) C—$R^9$ and Y is C—$R^{10}$,
n is 0 or 1,
with the proviso that $R^8$ is lower alkyl, when
a) $R^1$ is hydrogen, $R^2$ is hydrogen, $R^3$ is methyl, $R^4$ is methyl, $R^6$ is hydrogen, $R^7$ is hydrogen, $R^9$ is hydrogen, $R^{10}$ is hydrogen, n is 0, X is C—$R^9$ and Y is C—$R^{10}$;
b) $R^1$ is hydrogen, $R^2$ is hydrogen, $R^3$ is methyl, $R^4$ is methyl, $R^6$ is hydrogen, $R^7$ is ethyl, $R^9$ is methyl, $R^{10}$ is hydrogen, n is 0, X is C—$R^9$ and Y is C—$R^{10}$;
c) $R^1$ is hydrogen, $R^2$ is hydrogen, $R^3$ is t-butyl, $R^4$ is t-butyl, $R^6$ is hydrogen, $R^7$ is hydrogen, $R^9$ is hydrogen, $R^{10}$ is hydrogen, n is 0, X is C—$R^9$ and Y is C—$R^{10}$;
d) $R^1$ is hydrogen, $R^2$ is hydrogen, $R^3$ is chloro, $R^4$ is hydrogen, $R^6$ is hydrogen, $R^7$ is hydrogen, $R^9$ is hydrogen, $R^{10}$ is hydrogen, n is 0, X is C—$R^9$ and Y is C—$R^{10}$;
e) $R^1$ is hydrogen, $R^2$ is hydrogen, $R^3$ is chloro, $R^4$ is morpholino, $R^6$ is hydrogen, $R^7$ is hydrogen, $R^9$ is hydrogen, $R^{10}$ is hydrogen, n is 0, X is C—$R^9$ and Y is C—$R^{10}$;
f) $R^1$ is hydrogen, $R^2$ is hydrogen, $R^3$ is chloro, $R^4$ is hydrogen, $R^6$ is hydrogen, $R^7$ is hydrogen, $R^9$ is chloro, $R^{10}$ is hydrogen, n is 0, X is C—$R^9$ and Y is C—$R^{10}$;
g) $R^1$ is hydrogen, $R^2$ is hydrogen, $R^3$ is chloro, $R^4$ is hydrogen, $R^6$ is methyl, $R^7$ is hydrogen, $R^9$ is hydrogen, n is 0, X is C—$R^9$ and Y is N; or
h) $R^1$ is hydrogen, $R^2$ is hydrogen, $R^3$ is chloro, $R^4$ is hydrogen, $R^6$ is methyl, $R^7$ is hydrogen, $R^{10}$ is hydrogen, n is 0, X is N and Y is C—$R^{10}$;
or pharmaceutically active salts or esters thereof.

One further embodiment of the invention provides compounds of formula I as described herein, wherein X is C—$R^9$, Y is C—$R^{10}$, $R^9$ is hydrogen, halogen, lower alkyl, or lower alkoxy and $R^{10}$ is hydrogen, halogen, lower alkyl, lower alkoxy, or phenyl, wherein the phenyl is optionally substituted by halogen, lower alkyl, or —S(O)$_2$-lower alkyl.

One further embodiment of the invention provides compounds of formula I as described herein, wherein X is CH, Y is C—$R^{10}$ and $R^{10}$ is hydrogen, halogen, lower alkyl, lower alkoxy, or phenyl, wherein the phenyl is optionally substituted by halogen, lower alkyl, or —S(O)$_2$-lower alkyl.

One further embodiment of the invention provides compounds of formula I as described herein, wherein X is N, Y is C—$R^{10}$ and $R^{10}$ is hydrogen, halogen, lower alkyl, lower alkoxy, or phenyl, wherein the phenyl is optionally substituted by halogen, lower alkyl, or —S(O)$_2$-lower alkyl.

One further embodiment of the invention provides compounds of formula I as described herein, wherein X is C—$R^9$ and Y is N, and $R^9$ is hydrogen, halogen, lower alkyl, or lower alkoxy.

One further embodiment of the invention provides compounds of formula I as described herein, wherein X is C—$R^9$ and Y is N, and $R^9$ is hydrogen or Me.

One further embodiment of the invention provides compounds of formula I as described herein, wherein X is C—$R^9$ and Y is C—$R^{10}$, $R^{10}$ is hydrogen, F, Me, MeO, or Me-SO$_2$-Ph- and $R^9$ is hydrogen, F, Me or MeO.

One further embodiment of the invention provides compounds of formula I as described herein, wherein X is N and Y is C—H.

One further embodiment of the invention provides compounds of formula I as described herein, wherein $R^1$ is hydrogen or halogen.

One further embodiment of the invention provides compounds of formula I as described herein, wherein $R^1$ is hydrogen or F.

One further embodiment of the invention provides compounds of formula I as described herein, wherein $R^1$ is hydrogen.

One further embodiment of the invention provides compounds of formula I as described herein, wherein $R^1$ is F.

One further embodiment of the invention provides compounds of formula I as described herein, wherein $R^2$ is hydrogen, halogen or lower alkyl.

One further embodiment of the invention provides compounds of formula I as described herein, wherein $R^2$ is hydrogen or halogen.

One further embodiment of the invention provides compounds of formula I as described herein, wherein $R^2$ is hydrogen, F, Cl or Me.

One further embodiment of the invention provides compounds of formula I as described herein, wherein $R^2$ is hydrogen, chloro or fluoro.

One further embodiment of the invention provides compounds of formula I as described herein, wherein $R^2$ is hydrogen.

One further embodiment of the invention provides compounds of formula I as described herein, wherein $R^2$ is halogen.

One further embodiment of the invention provides compounds of formula I as described herein, wherein $R^2$ is F.

One further embodiment of the invention provides compounds of formula I as described herein, wherein $R^2$ is Cl.

One further embodiment of the invention provides compounds of formula I as described herein, wherein $R^2$ is lower alkyl.

One further embodiment of the invention provides compounds of formula I as described herein, wherein $R^2$ is Me.

One further embodiment of the invention provides compounds of formula I as described herein, wherein $R^3$ is halogen, lower alkyl, or halogen-lower alkyl.

One further embodiment of the invention provides compounds of formula I as described herein, wherein $R^3$ is halogen or lower alkyl.

One further embodiment of the invention provides compounds of formula I as described herein, wherein $R^3$ is Cl, Me or CF$_3$.

One further embodiment of the invention provides compounds of formula I as described herein, wherein $R^3$ is chloro or methyl.

One further embodiment of the invention provides compounds of formula I as described herein, wherein $R^3$ is halogen.

One further embodiment of the invention provides compounds of formula I as described herein, wherein $R^3$ is Cl.

One further embodiment of the invention provides compounds of formula I as described herein, wherein $R^3$ is lower alkyl.

One further embodiment of the invention provides compounds of formula I as described herein, wherein $R^3$ is Me.

One further embodiment of the invention provides compounds of formula I as described herein, wherein $R^3$ is halogen-lower alkyl.

One further embodiment of the invention provides compounds of formula I as described herein, wherein $R^3$ is CF$_3$.

One further embodiment of the invention provides compounds of formula I as described herein, wherein $R^5$ is fluoro or methyl.

One further embodiment of the invention provides compounds of formula I as described herein, wherein $R^5$ is halogen.

One further embodiment of the invention provides compounds of formula I as described herein, wherein $R^5$ is fluoro.

One further embodiment of the invention provides compounds of formula I as described herein, wherein $R^5$ is lower alkyl.

One further embodiment of the invention provides compounds of formula I as described herein, wherein $R^5$ is methyl.

One further embodiment of the invention provides compounds of formula I as described herein, wherein $R^6$ is hydrogen or lower alkyl.

One further embodiment of the invention provides compounds of formula I as described herein, wherein $R^6$ is hydrogen or Me.

One further embodiment of the invention provides compounds of formula I as described herein, wherein $R^6$ is hydrogen.

One further embodiment of the invention provides compounds of formula I as described herein, wherein $R^6$ is lower alkyl.

One further embodiment of the invention provides compounds of formula I as described herein, wherein $R^6$ is Me.

One further embodiment of the invention provides compounds of formula I as described herein, wherein $R^7$ is hydrogen or lower alkyl.

One further embodiment of the invention provides compounds of formula I as described herein, wherein $R^7$ is hydrogen, Me or Et.

One further embodiment of the invention provides compounds of formula I as described herein, wherein $R^7$ is hydrogen.

One further embodiment of the invention provides compounds of formula I as described herein, wherein $R^7$ is lower alkyl.

One further embodiment of the invention provides compounds of formula I as described herein, wherein $R^7$ is Me.

One further embodiment of the invention provides compounds of formula I as described herein, wherein $R^7$ is Et.

One further embodiment of the invention provides compounds of formula I as described herein, wherein $R^8$ is hydrogen or lower alkyl.

One further embodiment of the invention provides compounds of formula I as described herein, wherein $R^8$ is hydrogen or Me.

One further embodiment of the invention provides compounds of formula I as described herein, wherein $R^8$ is hydrogen.

One further embodiment of the invention provides compounds of formula I as described herein, wherein $R^8$ is lower alkyl.

One further embodiment of the invention provides compounds of formula I as described herein, wherein $R^8$ is Me.

One further embodiment of the invention provides compounds of formula I as described herein, wherein $R^9$ is hydrogen, halogen or lower alkyl.

One further embodiment of the invention provides compounds of formula I as described herein, wherein $R^9$ is hydrogen, fluoro or methyl.

One further embodiment of the invention provides compounds of formula I as described herein, wherein $R^9$ is hydrogen.

One further embodiment of the invention provides compounds of formula I as described herein, wherein $R^9$ is halogen.

One further embodiment of the invention provides compounds of formula I as described herein, wherein $R^9$ is fluoro.

One further embodiment of the invention provides compounds of formula I as described herein, wherein $R^9$ is lower alkyl.

One further embodiment of the invention provides compounds of formula I as described herein, wherein $R^9$ is methyl.

One further embodiment of the invention provides compounds of formula I as described herein, wherein $R^{10}$ is hydrogen or halogen.

One further embodiment of the invention provides compounds of formula I as described herein, wherein $R^{10}$ is hydrogen.

One further embodiment of the invention provides compounds of formula I as described herein, wherein $R^{10}$ is halogen.

One further embodiment of the invention provides compounds of formula I as described herein, wherein $R^{10}$ is fluoro.

One further embodiment of the invention provides compounds of formula I as described herein, wherein $R^{10}$ is hydrogen or fluoro.

One further embodiment of the invention provides compounds of formula I as described herein, wherein $R^{11}$ is hydrogen.

One further embodiment of the invention provides compounds of formula I as described herein, wherein $R^{11}$ is lower alkyl.

One further embodiment of the invention provides compounds of formula I as described herein, wherein $R^{11}$ is methyl.

One further embodiment of the invention provides compounds of formula I as described herein, wherein $R^{12}$ is hydrogen.

One further embodiment of the invention provides compounds of formula I as described herein, wherein $R^{12}$ is lower alkyl.

One further embodiment of the invention provides compounds of formula I as described herein, wherein $R^{12}$ is methyl.

One further embodiment of the invention provides compounds of formula I as described herein, wherein n is 0.

One further embodiment of the invention provides compounds of formula I as described herein, wherein n is 1.

One further embodiment of the invention provides compounds of formula I as described herein, wherein $R^4$ is
a) lower alkyl,
b) lower alkoxy, optionally substituted by halogen, hydroxyl, cycloalkyl or heterocyclyl,
c) —Si(lower alkyl)$_3$,
d) —O-cycloalkyl,
e) —O-aryl,
f) —O-heterocyclyl, optionally substituted acetyl,
wherein each S being part of a heterocyclyl is optionally substituted by oxo,
g) heteroaryl, optionally substituted by halogen, lower alkyl, lower alkoxy, —NR$^{11}$R$^{12}$, or —S(O)$_2$-lower alkyl, or
h) aryl, substituted by halogen, amido, nitro, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
and $R^4$ is hydrogen when $R^{11}$ is phenyl, substituted by —S(O)$_2$-lower alkyl,
and $R^4$ is aryl when $R^6$ is lower alkyl.

One further embodiment of the invention provides compounds of formula I as described herein, wherein $R^4$ is
a) lower alkoxy, optionally substituted by halogen, hydroxyl, cycloalkyl or heterocyclyl,
b) —O-aryl, or
c) —O-heterocyclyl, wherein each S being part of a heterocyclyl is optionally substituted by oxo.

One further embodiment of the invention provides compounds of formula I as described herein, wherein $R^4$ is tetrafluoro-ethoxy-, —O-tetrahydrothiopyran dioxide, —SiMe$_3$, acetamidyl-Ph-, acetyl-piperidin-O—, amido-Ph-, trifluoro-MeO-Ph-, CF$_3$-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, F-Ph-, F-pyridinyl-, i-butoxy-, isopropoxy-, isopropoxy, F-Ph-, isopropoxy-Ph-, dimethyl-thiazolyl-, Me-Ph-, Me-SO$_2$-Ph-, Me-SO$_2$-pyridinyl-, morpholino-, N(Me)$_2$-Ph-, NH$_2$-pyridinyl-, nitro-Ph-, OH,Cl-isopentyloxy-, OMe-Me-Ph-, OMe-Ph-, OMe-pyridinyl-, oxetanyl-propoxy-, Ph-O—, pyridinyl-, pyrimidinyl-, sec-butoxy-, t-butyl, tetrahydrofuran-O—, tetrahydrofuran-ethoxy-, tetrahydropyran-ethoxy-, tetrahydropyran-O— or thienyl-, and $R^4$ is H when $R^{11}$ is Me-SO$_2$-Ph-, and $R^4$ is Ph when $R^6$ is Me.

One further embodiment of the invention provides compounds of formula I as described herein, wherein $R^4$ is —O-tetrahydropyranyl, —O-tetrahydrofuranyl, isopropoxy, tetrahydrofuranyl-ethoxy-, 4-chloro-2-hydroxy-butoxy-, 2-oxetanyl-propoxy-, 1,1,2,2-tetrafluoro-ethoxy-, chloro-hydroxy-isopentyloxy-, —O-tetrahydrothiopyranyl dioxide, tetrahydropyranyl-ethoxy-, 2,2,2-trifluoro-ethoxy-, 2-cyclopropyl-ethoxy-, —O-cyclopentyl, —O-cyclohexyl, i-butoxy, sec-butoxy, difluoro-isopropoxy-, —O-phenyl, 2,2,3,3,3-pentafluoro-propoxy- or trifluoro-isopropoxy-.

One further embodiment of the invention provides compounds of formula I as described herein, wherein $R^4$ is H and $R^{10}$ is Me-SO$_2$-Ph-.

One further embodiment of the invention provides compounds of formula I as described herein, wherein $R^4$ is Ph and $R^6$ is Me.

One further embodiment of the invention provides compounds of formula I as described herein, wherein $R^4$ is tetrafluoro-ethoxy-.

One further embodiment of the invention provides compounds of formula I as described herein, wherein $R^4$ is —O-tetrahydrothiopyran dioxide-.

One further embodiment of the invention provides compounds of formula I as described herein, wherein $R^4$ is —SiMe$_3$.

One further embodiment of the invention provides compounds of formula I as described herein, wherein $R^4$ is acetamidyl-Ph-.

One further embodiment of the invention provides compounds of formula I as described herein, wherein $R^4$ is acetyl-piperidin-O—.

One further embodiment of the invention provides compounds of formula I as described herein, wherein $R^4$ is amido-Ph-.

One further embodiment of the invention provides compounds of formula I as described herein, wherein $R^4$ is trifluoro-MeO-Ph-.

One further embodiment of the invention provides compounds of formula I as described herein, wherein $R^4$ is CF$_3$-Ph-.

One further embodiment of the invention provides compounds of formula I as described herein, wherein $R^4$ is Cl,OH-butoxy-; i.e. butoxy substituted by Cl and by OH.

One further embodiment of the invention provides compounds of formula I as described herein, wherein $R^4$ is Cl-Ph-.

One further embodiment of the invention provides compounds of formula I as described herein, wherein $R^4$ is cyclohexyl-O—.

One further embodiment of the invention provides compounds of formula I as described herein, wherein $R^4$ is cyclopentyl-O—.

One further embodiment of the invention provides compounds of formula I as described herein, wherein $R^4$ is cyclopropyl-ethoxy-.

One further embodiment of the invention provides compounds of formula I as described herein, wherein $R^4$ is difluoro-isopropoxy-.

One further embodiment of the invention provides compounds of formula I as described herein, wherein $R^4$ is pentafluoro-propoxy-.

One further embodiment of the invention provides compounds of formula I as described herein, wherein $R^4$ is trifluoro-isopropoxy-.

One further embodiment of the invention provides compounds of formula I as described herein, wherein $R^4$ trifluoro-ethoxy-.

One further embodiment of the invention provides compounds of formula I as described herein, wherein $R^4$ is trifluoro-propoxy-.

One further embodiment of the invention provides compounds of formula I as described herein, wherein $R^4$ is F-Ph-.

One further embodiment of the invention provides compounds of formula I as described herein, wherein $R^4$ is F-pyridinyl-.

One further embodiment of the invention provides compounds of formula I as described herein, wherein $R^4$ is i-butoxy-.

One further embodiment of the invention provides compounds of formula I as described herein, wherein $R^4$ is isopropoxy-.

One further embodiment of the invention provides compounds of formula I as described herein, wherein $R^4$ is isopropoxy, F-Ph-; i.e. phenyl substituted by fluoro and isopropoxy.

One further embodiment of the invention provides compounds of formula I as described herein, wherein $R^4$ is isopropoxy-Ph-.

One further embodiment of the invention provides compounds of formula I as described herein, wherein $R^4$ is dimethyl-thiazolyl-.

One further embodiment of the invention provides compounds of formula I as described herein, wherein $R^4$ is Me-Ph-.

One further embodiment of the invention provides compounds of formula I as described herein, wherein $R^4$ is Me-SO$_2$-Ph-.

One further embodiment of the invention provides compounds of formula I as described herein, wherein $R^4$ is Me-SO$_2$-pyridinyl-.

One further embodiment of the invention provides compounds of formula I as described herein, wherein $R^4$ is morpholino-.

One further embodiment of the invention provides compounds of formula I as described herein, wherein $R^4$ is N(Me)$_2$-Ph-.

One further embodiment of the invention provides compounds of formula I as described herein, wherein $R^4$ is NH$_2$-pyridinyl-.

One further embodiment of the invention provides compounds of formula I as described herein, wherein $R^4$ is nitro-Ph-.

One further embodiment of the invention provides compounds of formula I as described herein, wherein $R^4$ is OH,Cl-isopentyloxy-; i.e., isopentyloxy substituted by Cl and OH.

One further embodiment of the invention provides compounds of formula I as described herein, wherein $R^4$ is OMe-Me-Ph-.

One further embodiment of the invention provides compounds of formula I as described herein, wherein $R^4$ is OMe-Ph-.

One further embodiment of the invention provides compounds of formula I as described herein, wherein $R^4$ is OMe-pyridinyl-.

One further embodiment of the invention provides compounds of formula I as described herein, wherein $R^4$ is oxetanyl-propoxy-.

One further embodiment of the invention provides compounds of formula I as described herein, wherein $R^4$ is Ph-O—.

One further embodiment of the invention provides compounds of formula I as described herein, wherein $R^4$ is pyridinyl-.

One further embodiment of the invention provides compounds of formula I as described herein, wherein $R^4$ is pyrimidinyl-.

One further embodiment of the invention provides compounds of formula I as described herein, wherein $R^4$ is sec-butoxy-.

One further embodiment of the invention provides compounds of formula I as described herein, wherein $R^4$ is t-butyl.

One further embodiment of the invention provides compounds of formula I as described herein, wherein $R^4$ is tetrahydrofuran-O—.

One further embodiment of the invention provides compounds of formula I as described herein, wherein $R^4$ is tetrahydrofuran-ethoxy-.

One further embodiment of the invention provides compounds of formula I as described herein, wherein $R^4$ is tetrahydropyran-ethoxy-.

One further embodiment of the invention provides compounds of formula I as described herein, wherein $R^4$ is tetrahydropyran-O—.

One further embodiment of the invention provides compounds of formula I as described herein, wherein $R^4$ is thienyl-.

One further embodiment of the invention provides compounds of formula I as described herein, wherein $R^4$ is 1,1,2,2-tetrafluoro-ethoxy.

One further embodiment of the invention provides compounds of formula I as described herein, wherein $R^4$ is 2,2,2-trifluoroethoxy.

One further embodiment of the invention provides compounds of formula I as described herein, wherein $R^4$ is 1-Me-2,2,2-trifluoroethoxy.

One further embodiment of the invention provides compounds of formula I as described herein, wherein $R^4$ is 2-fluoro-1-fluoro-Me-ethoxy.

One further embodiment of the invention are compounds of formula I as described herein, wherein $R^4$ is 2-Cl-Me-2-HO-Me-propoxy.

One further embodiment of the invention are compounds of formula I as described herein, wherein $R^4$ is 3,3,3-trifluoro-propoxy.

One further embodiment of the invention provides compounds of formula I as described herein, wherein $R^4$ is 3,3,3-trifluoro-2,2-difluoro-propoxy.

One further embodiment of the invention provides compounds of formula I as described herein, wherein $R^4$ is 4-Cl-2-OH-butoxy.

One further embodiment of the invention provides compounds of formula I as described herein, wherein $R^4$ is a) lower alkoxy, optionally substituted by halogen, hydroxyl, cycloalkyl or heterocyclyl b) —O-cycloalkyl, c) —O-aryl, or d) —O-heterocyclyl, optionally substituted acetyl.

One further embodiment of the invention provides compounds of formula I as described herein, wherein $R^4$ is tetrafluoro-ethoxy-, —O-tetrahydrothiopyran dioxide, acetyl-piperidin-O—, amido-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, i-butoxy-, isopropoxy-, OH,Cl-isopentyloxy-, oxetanyl-propoxy-, Ph-O—, sec-butoxy-, tetrahydrofuran-O—, tetrahydropyran-ethoxy-, tetrahydrofuran-ethoxy- or tetrahydropyran-O—.

One further embodiment of the invention provides compounds of formula I as described herein, wherein $R^1$ is hydrogen or F, $R^2$ is hydrogen, F, Cl or Me, $R^3$ is Cl, Me or $CF_3$, $R^4$ is tetrafluoro-ethoxy-, —O-tetrahydrothiopyran dioxide, —$SiMe_3$, acetamidyl-Ph-, acetyl-piperidin-O—, amido-Ph-, trifluoro-MeO-Ph-, $CF_3$-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, F-Ph-, F-pyridinyl-, i-butoxy-, isopropoxy-, isopropoxy, F-Ph-, isopropoxy-Ph-, dimethyl-thiazolyl-, Me-Ph-, Me-$SO_2$-Ph-, Me-$SO_2$-pyridinyl-, morpholino-, $N(Me)_2$-Ph-, $NH_2$-pyridinyl-, nitro-Ph-, OH,Cl-isopentyloxy-, OMe-Me-Ph-, OMe-Ph-, OMe-pyridinyl-, oxetanyl-propoxy-, Ph-O—, pyridinyl-, pyrimidinyl-, sec-butoxy-, t-butyl, tetrahydrofuran-O—, tetrahydrofuran-ethoxy-, tetrahydropyran-ethoxy-, tetrahydropyran-O— or thienyl-, and $R^4$ is H when $R^{11}$ is Me-$SO_2$-Ph-, and $R^4$ is Ph when $R^6$ is Me, $R^6$ is hydrogen or Me, $R^7$ is hydrogen, Me or Et, $R^8$ is hydrogen or Me, and X is C—$R^9$ and Y is C—$R^{10}$, wherein $R^9$ is hydrogen, F, Me or MeO and $R^{10}$ is hydrogen, F, Me, MeO, or Me-$SO_2$-Ph-, X is N and Y is CH, or X is C—$R^9$ and Y is N, wherein $R^9$ is hydrogen, or Me, or pharmaceutically active salts or esters thereof.

One further embodiment of the invention provides a method for treatment of psychoses, dysfunction in memory and learning, schizophrenia, dementia, attention deficit disorder, or Alzheimer's disease which comprises administering a compound of formula M as described herein, wherein

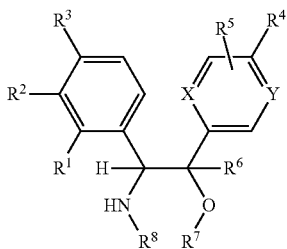

wherein
R¹ is hydrogen, halogen, lower alkyl, or lower alkoxy,
R² is hydrogen, halogen, lower alkyl, or lower alkoxy,
R³ is hydrogen, halogen, lower alkoxy or lower alkyl, wherein the lower alkyl is optionally substituted by halogen,
R⁴ is a) hydrogen,
  b) halogen,
  c) lower alkyl, optionally substituted by halogen or hydroxyl,
  d) lower alkoxy, optionally substituted by halogen, hydroxyl, cycloalkyl or heterocyclyl,
  e) —NR⁹R¹⁰,
  f) —S(O)₂-lower alkyl,
  g) —Si(lower alkyl)₃,
  h) —O-cycloalkyl,
  i) —O-aryl,
  j) —O-heteroaryl,
  k) —O-heterocyclyl,
  l) aryl,
  m) heteroaryl, or
  n) heterocyclyl,
  wherein each of the cycloalkyl, aryl, heteroaryl and heterocyclyl is optionally substituted by halogen, amido, nitro, acetyl, acetamidyl, lower alkyl, halogen-lower alkyl, lower alkoxy-lower alkyl, —NR⁹R¹⁰, lower alkoxy, halogen-lower alkoxy, or —S(O)₂-lower alkyl,
  and wherein each S being part of a heterocyclyl is optionally substituted by oxo,
R⁵ is hydrogen, halogen, lower alkyl, or lower alkoxy,
R⁶ is hydrogen or lower alkyl,
R⁷ is hydrogen or lower alkyl,
R⁸ is hydrogen or lower alkyl,
R⁹ is hydrogen or lower alkyl,
R¹⁰ is hydrogen or lower alkyl,
R¹¹ is hydrogen, halogen, lower alkyl, lower alkoxy or phenyl, wherein the phenyl is optionally substituted by halogen, lower alkyl, or —S(O)₂-lower alkyl, and
X is a) N and Y is C—R¹¹,
  b) C—R⁵ and Y is N, or
  c) C—R⁵ and Y is C—R¹¹,
or pharmaceutically active salts or esters thereof, for the preparation of medicaments for the treatment of psychoses, dysfunction in memory and learning, schizophrenia, dementia, attention deficit disorders or Alzheimer's disease.

One further embodiment of the invention provides compounds of formula M as described herein, wherein
R¹ is hydrogen, halogen or lower alkyl,
R² is hydrogen, halogen or lower alkyl,
R³ is halogen or lower alkyl, which lower alkyl is optionally substituted by halogen,
R⁴ is a) lower alkyl, optionally substituted by halogen,
  b) lower alkoxy, optionally substituted by halogen, hydroxyl, cycloalkyl or heterocyclyl,
  c) —Si(lower alkyl)₃,
  d) —O-cycloalkyl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl,
  e) —O-aryl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl,
  f) —O-heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl,
  g) —O-heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl, wherein each S being part of a heterocyclyl is optionally substituted by oxo,
  h) heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl,
  i) aryl, substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl, or
  j) heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR⁹R¹⁰, or —S(O)₂-lower alkyl,
and R⁴ is hydrogen when R¹¹ is phenyl, wherein the phenyl is optionally substituted by halogen, lower alkyl, or —S(O)₂-lower alkyl,
and R⁴ is aryl when R⁶ is lower alkyl,
R⁵ is hydrogen, halogen, lower alkyl, or lower alkoxy,
R⁶ is hydrogen or lower alkyl,
R⁷ is hydrogen or lower alkyl,
R⁸ is hydrogen or lower alkyl,
R⁹ is hydrogen or lower alkyl,
R¹⁰ is hydrogen or lower alkyl,
R¹¹ is hydrogen, halogen, lower alkyl, lower alkoxy or phenyl, wherein the phenyl is optionally substituted by halogen, lower alkyl, or —S(O)₂-lower alkyl, and
X is a) N and Y is C—R¹¹,
  b) C—R⁵ and Y is N, or
  c) C—R⁵ and Y is C—R¹¹,
or pharmaceutically active salts or esters thereof.

One further embodiment of the invention provides compounds of formula M as described herein, wherein X is C—R⁵ and Y is C—R¹¹, wherein
R⁵ is hydrogen, halogen, lower alkyl, or lower alkoxy, and
R¹¹ is hydrogen, halogen, lower alkyl, lower alkoxy or phenyl, wherein the phenyl is optionally substituted by halogen, lower alkyl, or —S(O)₂-lower alkyl.

One further embodiment of the invention provides compounds of formula M as described herein, wherein X is C—R⁵ and Y is C—R¹¹, wherein
R⁵ is hydrogen, F, Me or MeO, and
R¹¹ is hydrogen, F, Me, MeO, or Me-SO₂-Ph-.

One further embodiment of the invention provides compounds of formula M as described herein, wherein X is N and Y is CH.

One further embodiment of the invention provides compounds of formula M as described herein, wherein X is C—$R^5$ and Y is N, wherein $R^5$ is hydrogen, halogen, lower alkyl, or lower alkoxy.

One further embodiment of the invention provides compounds of formula M as described herein, wherein X is —C—$R^5$ and Y is N, wherein $R^5$ is hydrogen or Me.

One further embodiment of the invention provides compounds of formula M as described herein, wherein $R^1$ is hydrogen or halogen.

One further embodiment of the invention provides compounds of formula M as described herein, wherein $R^1$ is hydrogen or F.

One further embodiment of the invention provides compounds of formula M as described herein, wherein $R^2$ is hydrogen, halogen or lower alkyl.

One further embodiment of the invention provides compounds of formula M as described herein, wherein $R^2$ is hydrogen, F, Cl or Me.

One further embodiment of the invention provides compounds of formula M as described herein, wherein $R^3$ is halogen, lower alkyl, or halogen-lower alkyl.

One further embodiment of the invention are compounds of formula M as described herein, wherein $R^3$ is Cl, Me or $CF_3$.

One further embodiment of the invention provides compounds of formula M as described herein, wherein $R^6$ is hydrogen or lower alkyl.

One further embodiment of the invention provides compounds of formula M as described herein, wherein $R^6$ is hydrogen or Me.

One further embodiment of the invention provides compounds of formula M as described herein, wherein $R^7$ is hydrogen or lower alkyl.

One further embodiment of the invention provides compounds of formula M as described herein, wherein $R^7$ is hydrogen, Me or Et.

One further embodiment of the invention provides compounds of formula M as described herein, wherein $R^8$ is hydrogen or lower alkyl.

One further embodiment of the invention provides compounds of formula M as described herein, wherein $R^8$ is hydrogen or Me.

One further embodiment of the invention provides compounds of formula M as described herein, wherein $R^4$ is
a) lower alkyl,
b) lower alkoxy, optionally substituted by halogen, hydroxyl, cycloalkyl or heterocyclyl,
c) —Si(lower alkyl)$_3$,
d) —O-cycloalkyl,
e) —O-aryl,
e) —O-heterocyclyl, optionally substituted acetyl,
    wherein each S being part of a heterocyclyl is optionally substituted by oxo,
f) heteroaryl, optionally substituted by halogen, lower alkyl, lower alkoxy, —$NR^9R^{10}$, or —$S(O)_2$-lower alkyl, or
g) aryl, substituted by halogen, amido, nitro, acetamidyl, lower alkyl, halogen-lower alkyl, lower alkoxy-lower alkyl, lower alkoxy, halogen-lower alkoxy, —$NR^9R^{10}$, or —$S(O)_2$-lower alkyl, and $R^4$ is hydrogen when $R^{11}$ is phenyl, substituted by —$S(O)_2$-lower alkyl, and $R^4$ is aryl when $R^6$ is lower alkyl.

One further embodiment of the invention provides compounds of formula M as described herein, wherein $R^4$ is tetrafluoro-ethoxy-, —O-tetrahydrothiopyran dioxide, —SiMe$_3$, acetamidyl-Ph-, acetyl-piperidin-O—, amido-Ph-, trifluoro-MeO-Ph-, $CF_3$-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, F-Ph-, F-pyridinyl-, i-butoxy-, isopropoxy-, isopropoxy, F-Ph-, isopropoxy-Ph-, dimethyl-thiazolyl-, Me-Ph-, Me-SO$_2$-Ph-, Me-SO$_2$-pyridinyl-, morpholino-, N(Me)$_2$-Ph-, NH$_2$-pyridinyl-, nitro-Ph-, OH,Cl-isopentyloxy-, OMe-Me-Ph-, OMe-Ph-, OMe-pyridinyl-, oxetanyl-propoxy-, Ph-O—, pyridinyl-, pyrimidinyl-, sec-butoxy-, t-butyl, tetrahydrofuran-O—, tetrahydrofuran-ethoxy-, tetrahydropyran-ethoxy-, tetrahydropyran-O— or thienyl-, and $R^4$ is H when $R^{11}$ is Me-SO$_2$-Ph-, and $R^4$ is Ph when $R^6$ is Me.

One further embodiment of the invention provides compounds of formula M as described herein, wherein $R^4$ is
a) lower alkoxy, optionally substituted by halogen, hydroxyl, cycloalkyl or heterocyclyl
b) —O-cycloalkyl,
c) —O-aryl, or
d) —O-heterocyclyl, optionally substituted acetyl.

One further embodiment of the invention provides compounds of formula M as described herein, wherein $R^4$ is tetrafluoro-ethoxy-, —O-tetrahydrothiopyran dioxide, acetyl-piperidin-O—, amido-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, i-butoxy-, isopropoxy-, OH,Cl-isopentyloxy-, oxetanyl-propoxy-, Ph-O—, sec-butoxy-, tetrahydrofuran-O—, tetrahydropyran-ethoxy-, tetrahydrofuran-ethoxy- or tetrahydropyran-O—.

One further embodiment of the invention provides compounds of formula M as described herein, wherein $R^1$ is hydrogen or F, $R^2$ is hydrogen, F, Cl or Me, $R^3$ is Cl, Me or $CF_3$, $R^4$ is tetrafluoro-ethoxy-, —O-tetrahydrothiopyran dioxide, —SiMe$_3$, acetamidyl-Ph-, acetyl-piperidin-O—, amido-Ph-, trifluoro-MeO-Ph-, $CF_3$-Ph-, Cl,OH-butoxy-, Cl-Ph-, cyclohexyl-O—, cyclopentyl-O—, cyclopropyl-ethoxy-, difluoro-isopropoxy-, pentafluoro-propoxy-, trifluoro-isopropoxy-, trifluoro-ethoxy-, trifluoro-propoxy-, F-Ph-, F-pyridinyl-, i-butoxy-, isopropoxy-, isopropoxy, F-Ph-, isopropoxy-Ph-, dimethyl-thiazolyl-, Me-Ph-, Me-SO$_2$-Ph-, Me-SO$_2$-pyridinyl-, morpholino-, N(Me)$_2$-Ph-, NH$_2$-pyridinyl-, nitro-Ph-, OH,Cl-isopentyloxy-, OMe-Me-Ph-, OMe-Ph-, OMe-pyridinyl-, oxetanyl-propoxy-, Ph-O—, pyridinyl-, pyrimidinyl-, sec-butoxy-, t-butyl, tetrahydrofuran-O—, tetrahydrofuran-ethoxy-, tetrahydropyran-ethoxy-, tetrahydropyran-O— or thienyl-, and $R^4$ is H when $R^{11}$ is Me-SO$_2$-Ph-, and $R^4$ is Ph when $R^6$ is Me, $R^6$ is hydrogen or Me, $R^7$ is hydrogen, Me or Et, $R^8$ is hydrogen or Me, and X is C—$R^5$ and Y is C—$R^{11}$, wherein $R^5$ is hydrogen, F, Me or MeO and $R^{11}$ is hydrogen, F, Me, MeO, or Me-SO$_2$-Ph-, X is N and Y is CH, or X is C—$R^5$ and Y is N, wherein $R^5$ is hydrogen, or Me, or pharmaceutically active salts or esters thereof.

One further embodiment of the invention provides compounds of formula I as described herein having formula Ia,

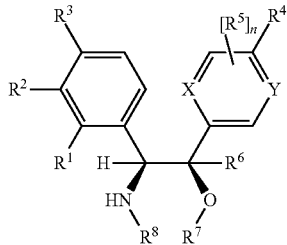

wherein the $R^1$, $R^2$, $R^3$, $R^4$, $R^5$, $R^6$, $R^7$, $R^8$, n, X and Y are defined in any of the embodiments, or pharmaceutically active salts or esters thereof.

One further embodiment of the invention provides compounds of formula I as described herein having formula Ib,

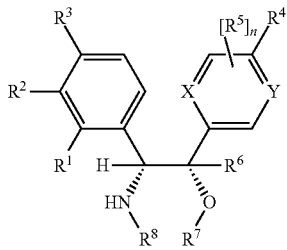

wherein the $R^1$, $R^2$, $R^3$, $R^4$, $R^5$, $R^6$, $R^7$, $R^8$, n, X and Y are defined in any of the embodiments, or pharmaceutically active salts or esters thereof.

One further embodiment of the invention provides compounds selected from the group consisting of
rac-erythro-[2-Amino-2-(3,4-dichloro-phenyl)-1-(3-fluoro-3'-methanesulfonyl-biphenyl-4-yl)-ethanol trifluoroacetate,
rac-erythro-[2-Amino-2-(3,4-dichloro-phenyl)-1-[4-(5-fluoro-pyridin-3-yl)-2-methyl-phenyl]]-ethanol dihydrochloride,
rac-erythro-[2-Amino-2-(3,4-dichloro-phenyl)-1-[4-(5-fluoro-pyridin-3-yl)-3-methoxy-phenyl]-ethanol dihydrochloride,
rac-erythro-[2-Amino-2-(3,4-dichloro-phenyl)-1-[4-(5-fluoro-pyridin-3-yl)-2-methoxy-phenyl]-ethanol dihydrochloride,
rac-erythro-[2-Amino-2-(3,4-dichloro-phenyl)-1-(3'-methanesulfonyl-biphenyl-3-yl)-ethanol trifluoroacetate,
(1R,2S or 1S,2R)-2-Amino-2-(3,4-dichloro-phenyl)-1-(3-fluoro-3'-methanesulfonyl-biphenyl-4-yl)-ethanol hydrochloride,
rac-erythro-[2-Amino-2-(3,4-dichloro-phenyl)-1-(3'-methanesulfonyl-biphenyl-4-yl)-ethanol trifluoroacetate,
(1R,2S or 1S,2R)-2-Amino-2-(3,4-dichloro-phenyl)-1-[4-(5-fluoro-pyridin-3-yl)-phenyl]-ethanol trifluoroacetate,
rac-erythro-[2-Amino-2-(4-chloro-phenyl)-1-[4-(tetrahydro-pyran-3-yloxy)-phenyl]-ethanol,
rac-erythro-[2-Amino-2-(4-chloro-phenyl)-1-(4-isopropoxy-phenyl)-ethanol hydrochloride,
rac-erythro-[2-Amino-2-(3,4-dichloro-phenyl)-1-[5-(3-methanesulfonyl-phenyl)-pyridin-2-yl]-ethanol bistrifluoroacetate,
rac-erythro-[2-Amino-2-(3,4-dichloro-phenyl)-1-(5'-fluoro-[3,3]bipyridinyl-6-yl)-ethanol trihydrochloride,
rac-erythro-[2-Amino-2-(3,4-dichloro-phenyl)-1-[3-fluoro-5-(3-methoxy-phenyl)-pyridin-2-yl]-ethanol dihydrochloride,
rac-erythro-[2-Amino-2-(3,4-dichloro-phenyl)-1-[4-(5-fluoro-pyridin-3-yl)-3-methyl-phenyl]-ethanol bis-trifluoroacetate,
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
rac-erythro-[rac-2-Amino-2-(3,4-dichloro-phenyl)-1-[2-fluoro-4-(tetrahydro-furan-3-yloxy)-phenyl]-ethanol hydrochloride,
rac-erythro-[2-Amino-2-(3,4-dichloro-phenyl)-1-[2-methyl-6-(tetrahydro-pyran-4-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[rac-2-Amino-2-(3,4-dichloro-phenyl)-1-[6-(tetrahydro-furan-3-yloxy)-pyridin-3-yl]-ethanol dihydrochloride,
rac-erythro-[2-Amino-2-(3,4-dichloro-phenyl)-1-[3,5-difluoro-4-(tetrahydro-pyran-4-yloxy)-phenyl]-ethanol hydrochloride,
rac-erythro-[2-Amino-2-(3,4-dichloro-phenyl)-1-[4-methyl-6-(tetrahydro-pyran-4-yloxy)-pyridin-3-yl]-ethanol dihydrochloride,
rac-erythro-[2-Amino-2-(3,4-dichloro-phenyl)-1-[6-(tetrahydro-pyran-4-yloxy)-pyridin-3-yl]-ethanol dihydrochloride,
rac-erythro-[rac-2-Amino-2-(3,4-dichloro-phenyl)-1-[5-(tetrahydro-furan-3-yloxy)-pyridin-2-yl]-ethanol dihydrochloride,
rac-erythro-[(rac)-2-Amino-2-(3,4-dichloro-phenyl)-1-[4-methyl-6-(tetrahydro-furan-3-yloxy)-pyridin-3-yl]-ethanol dihydrochloride,
rac-erythro-[2-Amino-2-(3,4-dichloro-phenyl)-1-[5-(tetrahydro-pyran-4-yloxy)-pyridin-2-yl]-ethanol dihydrochloride,
rac-erythro-[2-Amino-2-(3,4-dichloro-phenyl)-1-[5-methyl-6-(tetrahydro-pyran-4-yloxy)-pyridin-3-yl]-ethanol dihydrochloride,
rac-erythro-[2-Amino-2-(3,4-dichloro-phenyl)-1-(6-isopropoxy-2-methyl-pyridin-3-yl)-ethanol dihydrochloride,
rac-erythro-[2-Amino-2-(3,4-dichloro-phenyl)-1-[2-fluoro-4-(tetrahydro-furan-2-ylmethoxy)-phenyl]-ethanol, hydrochloride salt,
rac-erythro-[1-[4-[(rac)-2-Amino-2-(3,4-dichloro-phenyl)-1-hydroxy-ethyl]-3-fluoro-phenoxy]-4-chloro-butan-2-ol hydrochloride,
rac-erythro-[2-Amino-2-(3,4-dichloro-phenyl)-1-(6-isopropoxy-4-methyl-pyridin-3-yl)-ethanol dihydrochloride,
rac-erythro-[(rac)-2-Amino-2-(3,4-dichloro-phenyl)-1-[5-methyl-6-(tetrahydro-furan-3-yloxy)-pyridin-3-yl]-ethanol dihydrochloride,
rac-erythro-[2-Amino-2-(3,4-dichloro-phenyl)-1-(5-isopropoxy-pyridin-2-yl)-ethanol dihydrochloride,
rac-erythro-[2-Amino-2-(3,4-dichloro-phenyl)-1-[2-fluoro-4-(tetrahydro-pyran-4-yloxy)-phenyl]-ethanol hydrochloride,
rac-erythro-[2-Amino-2-(3,4-dichloro-phenyl)-1-[2-fluoro-4-(3-methyl-oxetan-3-ylmethoxy)-phenyl]-ethanol,
rac-erythro-[2-Amino-2-(3,4-dichloro-phenyl)-1-(4-trimethylsilanyl-phenyl)-ethanol trifluoroacetate rac-erythro-[1-Amino-2-biphenyl-4-yl-1-(4-chloro-phenyl)-propan-2-ol trifluoroacetate,
rac-erythro-[2-Amino-1-(4-tert-butyl-phenyl)-2-(3,4-dichloro-phenyl)-ethanol trifluoroacetate,
rac-erythro-[2-Amino-2-(3,4-dichloro-phenyl)-1-[4-(1,1,2,2-tetrafluoro-ethoxy)-phenyl]-ethanol,
rac-erythro-[2-(3,4-Dichloro-phenyl)-1-[4-(5-fluoro-pyridin-3-yl)-phenyl]-2-methylamino-ethanol hydrochloride,
rac-erythro-[2-Amino-2-(3,4-dichloro-phenyl)-1-[4-(tetrahydro-pyran-4-yloxy)-phenyl]-ethanol,
(1R,2S or 1S,2R)-[2-Amino-2-(3,4-dichloro-phenyl)-1-[4-(tetrahydro-pyran-4-yloxy)-phenyl]-ethanol,
rac-erythro-[rac-2-Amino-2-(3,4-dichloro-phenyl)-1-[4-(tetrahydro-furan-3-yloxy)-phenyl]-ethanol,
rac-erythro-[2-Amino-2-(3,4-dichloro-phenyl)-1-hydroxyethyl]-phenoxy]-2-chloromethyl-2-methyl-propan-1-ol hydrochloride,
rac-erythro-2-Amino-2-(3,4-dichloro-phenyl)-1-[4-(1,1-dioxo-hexahydro-1-$\lambda^6$-thiopyran-4-yloxy)-phenyl]-ethanol,
rac-erythro-[2-Amino-2-(3,4-dichloro-phenyl)-1-[4-(tetrahydro-pyran-4-ylmethoxy)-phenyl]-ethanol,
rac-erythro-[1-(4-[4-[2-Amino-2-(3,4-dichloro-phenyl)-1-hydroxy-ethyl]-phenoxy]-piperidin-1-yl)-ethanone,
rac-erythro-[2-Amino-2-(3,4-dichloro-phenyl)-1-[4-(2,2,2-trifluoro-ethoxy)-phenyl]-ethanol,
rac-erythro-[2-Amino-2-(4-chloro-phenyl)-1-(4-cyclopentyloxy-phenyl)-ethanol hydrochloride,
rac-erythro-[2-Amino-1-(4-cyclopropylmethoxy-phenyl)-2-(3,4-dichloro-phenyl)-ethanol,
rac-erythro-2-Amino-2-(3,4-dichloro-phenyl)-1-(4-isobutoxy-phenyl)-ethanol,
rac-erythro-2-Amino-1-(4-sec-butoxy-phenyl)-2-(3,4-dichloro-phenyl)-ethanol,
rac-erythro-2-Amino-2-(3,4-dichloro-phenyl)-1-[4-(3,3,3-trifluoro-propoxy)-phenyl]-ethanol,
rac-erythro-2-Amino-2-(4-chloro-phenyl)-1-(4-cyclohexyloxy-phenyl)-ethanol,
rac-erythro-[2-Amino-2-(3-chloro-4-methyl-phenyl)-1-[4-(tetrahydro-pyran-4-yloxy)-phenyl]-ethanol,
rac-erythro-[2-Amino-2-(3-chloro-4-methyl-phenyl)-1-[4-(tetrahydro-pyran-4-yloxy)-phenyl]-ethanol,
rac-erythro-2-Amino-2-(3-chloro-4-methyl-phenyl)-1-(4-isopropoxy-phenyl)-ethanol,
rac-erythro-2-Amino-2-(3-fluoro-4-methyl-phenyl)-1-[4-(tetrahydro-pyran-4-yloxy)-phenyl]-ethanol,
rac-erythro-2-Amino-2-(4-chloro-phenyl)-1-[4-(2-fluoro-1-fluoromethyl-ethoxy)-phenyl]-ethanol,
rac-erythro-2-Amino-2-(4-chloro-phenyl)-1-[4-(tetrahydro-pyran-4-yloxy)-phenyl]-ethanol,
rac-erythro-2-Amino-2-(4-chloro-phenyl)-1-(3'-methoxymethyl-biphenyl-4-yl)-ethanol hydrochloride,
rac-erythro-2-Amino-2-(4-chloro-phenyl)-1-(4-pyridin-4-yl-phenyl)-ethanol,
rac-erythro-2-Amino-2-(4-chloro-phenyl)-1-(3'-methanesulfonyl-biphenyl-4-yl)-ethanol,
rac-erythro-2-Amino-2-(4-chloro-phenyl)-1-(4-pyridin-3-yl-phenyl)-ethanol hydrochloride,
rac-erythro-2-Amino-2-(4-chloro-phenyl)-1-[4-(5-methoxy-pyridin-3-yl)-phenyl]-ethanol,
rac-erythro-2-Amino-2-(4-chloro-phenyl)-1-(4-pyrimidin-5-yl-phenyl)-ethanol,
rac-erythro-2-Amino-2-(4-chloro-phenyl)-1-[4-(5-fluoro-pyridin-3-yl)-phenyl]-ethanol,
rac-erythro-N-[4'-[2-Amino-2-(4-chloro-phenyl)-1-hydroxy-ethyl]-biphenyl-3-yl]-acetamide,
rac-erythro-2-Amino-2-(4-chloro-phenyl)-1-(2'-fluoro-biphenyl-4-yl)-ethanol,
rac-erythro-2-Amino-1-[4-(6-amino-pyridin-3-yl)-phenyl]-2-(4-chloro-phenyl)-ethanol,
rac-erythro-2-Amino-2-(4-chloro-phenyl)-1-(4-thiophen-3-yl-phenyl)-ethanol,
rac-erythro-2-Amino-2-(4-chloro-phenyl)-1-(3'-methyl-biphenyl-4-yl)-ethanol,
rac-erythro-2-Amino-2-(4-chloro-phenyl)-1-(3'-methoxy-biphenyl-4-yl)-ethanol,
rac-erythro-2-Amino-1-(2'-chloro-biphenyl-4-yl)-2-(4-chloro-phenyl)-ethanol,
rac-erythro-2-Amino-1-(3'-chloro-biphenyl-4-yl)-2-(4-chloro-phenyl)-ethanol,
rac-erythro-2-Amino-2-(4-chloro-phenyl)-1-[4-(2,4-dimethyl-thiazol-5-yl)-phenyl]-ethanol,
rac-erythro-2-Amino-2-(4-chloro-phenyl)-1-(2'-methyl-biphenyl-4-yl)-ethanol,
rac-erythro-2-Amino-2-(4-chloro-phenyl)-1-[4-(6-methoxy-pyridin-3-yl)-phenyl]-ethanol,
rac-erythro-2-Amino-2-(4-chloro-phenyl)-1-(3'-trifluoromethoxy-biphenyl-4-yl)-ethanol,
rac-erythro-2-Amino-2-(4-chloro-phenyl)-1-(3'-trifluoromethyl-biphenyl-4-yl)-ethanol,
rac-erythro-2-Amino-2-(4-chloro-phenyl)-1-(6-morpholin-4-yl-pyridin-3-yl)-ethanol,
rac-erythro-2-Amino-2-(3,4-dichloro-phenyl)-1-(4-pyridin-3-yl-phenyl)-ethanol,
rac-erythro-2-Amino-2-(3,4-dichloro-phenyl)-1-[4-(5-methanesulfonyl-pyridin-3-yl)-phenyl]-ethanol,
rac-erythro-2-Amino-2-(3,4-dichloro-phenyl)-1-[4-(5-fluoro-pyridin-3-yl)-phenyl]-ethanol,
rac-erythro-2-Amino-2-(3,4-dichloro-phenyl)-1-(4-pyridin-3-yl-phenyl)-ethanol,
rac-erythro-2-Amino-2-(4-chloro-3-fluoro-phenyl)-1-[4-(5-fluoro-pyridin-3-yl)-phenyl]-ethanol,
rac-erythro-2-Amino-2-(4-chloro-3-methyl-phenyl)-1-(4-pyridin-3-yl-phenyl)-ethanol,
rac-erythro-2-Amino-1-(4-pyridin-3-yl-phenyl)-2-(4-trifluoromethyl-phenyl)-ethanol,
rac-erythro-2-Amino-2-(3,4-dichloro-phenyl)-1-(3'-dimethylamino-biphenyl-4-yl)-ethanol,
rac-erythro-2-Amino-2-(3-fluoro-4-methyl-phenyl)-1-(4-pyridin-3-yl-phenyl)-ethanol,
rac-erythro-2-Amino-2-(3-chloro-4-methyl-phenyl)-1-(4-pyridin-3-yl-phenyl)-ethanol,
rac-erythro-2-Amino-2-(3-chloro-4-methyl-phenyl)-1-[4-(5-fluoro-pyridin-3-yl)-phenyl]-ethanol,
rac-erythro-2-Amino-2-(3-fluoro-4-methyl-phenyl)-1-[4-(5-fluoro-pyridin-3-yl)-phenyl]-ethanol,
rac-erythro-2-Amino-2-(3-fluoro-4-trifluoromethyl-phenyl)-1-(4-pyridin-3-yl-phenyl)-ethanol,
rac-erythro-2-Amino-1-[4-(5-fluoro-pyridin-3-yl)-phenyl]-2-(3-fluoro-4-trifluoromethyl-phenyl)-ethanol,
rac-erythro-2-Amino-2-(4-chloro-2-fluoro-phenyl)-1-(4-pyridin-3-yl-phenyl)-ethanol,
rac-erythro-1-(3,4-Dichloro-phenyl)-2-methoxy-2-(4-pyridin-3-yl-phenyl)-ethylamine dihydrochloride,
rac-erythro-[1-(3,4-Dichloro-phenyl)-2-ethoxy-2-[4-(5-fluoro-pyridin-3-yl)-phenyl]-ethylamine trifluoroacetate,
rac-erythro-2-Amino-2-(3,4-dichloro-phenyl)-1-(4-phenoxy-phenyl)-ethanol,
rac-erythro-2-Amino-2-(4-chloro-phenyl)-1-[2-fluoro-4-(2,2,3,3,3-pentafluoro-propoxy)-phenyl]-ethanol,
rac-erythro-2-Amino-2-(4-chloro-phenyl)-1-[4-(2,2,2-trifluoro-1-methyl-ethoxy)-phenyl]-ethanol,
rac-erythro-2-Amino-2-(3,4-dichloro-phenyl)-1-(3'-nitro-biphenyl-4-yl)-ethanol, rac-erythro-4'42-Amino-2-(3,4-dichloro-phenyl)-1-hydroxy-ethyl]-biphenyl-3-carboxylic acid amide,
rac-erythro-2-Amino-2-(3,4-dichloro-phenyl)-1-(2'-fluoro-5'-isopropoxy-biphenyl-4-yl)-ethanol, and
rac-erythro-2-Amino-2-(3,4-dichloro-phenyl)-1-(3'-isopropoxy-biphenyl-4-yl)-ethanol,
or pharmaceutically active salts or esters thereof.

One further embodiment of the invention are compounds selected from the group of
rac-erythro-[2-Amino-2-(4-chloro-phenyl)-1-[4-(tetrahydro-pyran-3-yloxy)-phenyl]-ethanol,
rac-erythro-[2-Amino-2-(4-chloro-phenyl)-1-(4-isopropoxy-phenyl)-ethanol hydrochloride,
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
rac-erythro-[rac-2-Amino-2-(3,4-dichloro-phenyl)-1-[2-fluoro-4-(tetrahydro-furan-3-yloxy)-phenyl]-ethanol hydrochloride,
rac-erythro-[2-Amino-2-(3,4-dichloro-phenyl)-1-[2-methyl-6-(tetrahydro-pyran-4-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[rac-2-Amino-2-(3,4-dichloro-phenyl)-1-[6-(tetrahydro-furan-3-yloxy)-pyridin-3-yl]-ethanol dihydrochloride,
rac-erythro-[2-Amino-2-(3,4-dichloro-phenyl)-1-[3,5-difluoro-4-(tetrahydro-pyran-4-yloxy)-phenyl]-ethanol hydrochloride,
rac-erythro-[2-Amino-2-(3,4-dichloro-phenyl)-1-[4-methyl-6-(tetrahydro-pyran-4-yloxy)-pyridin-3-yl]-ethanol dihydrochloride,
rac-erythro-[2-Amino-2-(3,4-dichloro-phenyl)-1-[6-(tetrahydro-pyran-4-yloxy)-pyridin-3-yl]-ethanol dihydrochloride,
rac-erythro-[rac-2-Amino-2-(3,4-dichloro-phenyl)-1-[5-(tetrahydro-furan-3-yloxy)-pyridin-2-yl]-ethanol dihydrochloride,
rac-erythro-[(rac)-2-Amino-2-(3,4-dichloro-phenyl)-1-[4-methyl-6-(tetrahydro-furan-3-yloxy)-pyridin-3-yl]-ethanol dihydrochloride,
rac-erythro-[2-Amino-2-(3,4-dichloro-phenyl)-1-[5-(tetrahydro-pyran-4-yloxy)-pyridin-2-yl]-ethanol dihydrochloride,
rac-erythro-[2-Amino-2-(3,4-dichloro-phenyl)-1-[5-methyl-6-(tetrahydro-pyran-4-yloxy)-pyridin-3-yl]-ethanol dihydrochloride,
rac-erythro-[2-Amino-2-(3,4-dichloro-phenyl)-1-(6-isopropoxy-2-methyl-pyridin-3-yl)-ethanol dihydrochloride,
rac-erythro-[2-Amino-2-(3,4-dichloro-phenyl)-1-[2-fluoro-4-(tetrahydro-furan-2-ylmethoxy)-phenyl]-ethanol, hydrochloride salt,
rac-erythro-[1-[4-[(rac)-2-Amino-2-(3,4-dichloro-phenyl)-1-hydroxy-ethyl]-3-fluoro-phenoxy]-4-chloro-butan-2-ol hydrochloride,
rac-erythro-[2-Amino-2-(3,4-dichloro-phenyl)-1-(6-isopropoxy-4-methyl-pyridin-3-yl)-ethanol dihydrochloride,
rac-erythro-[(rac)-2-Amino-2-(3,4-dichloro-phenyl)-1-[5-methyl-6-(tetrahydro-furan-3-yloxy)-pyridin-3-yl]-ethanol dihydrochloride,
rac-erythro-[2-Amino-2-(3,4-dichloro-phenyl)-1-(5-isopropoxy-pyridin-2-yl)-ethanol dihydrochloride,
rac-erythro-[2-Amino-2-(3,4-dichloro-phenyl)-1-[2-fluoro-4-(tetrahydro-pyran-4-yloxy)-phenyl]-ethanol hydrochloride,
rac-erythro-[2-Amino-2-(3,4-dichloro-phenyl)-1-[2-fluoro-4-(3-methyl-oxetan-3-ylmethoxy)-phenyl]-ethanol,
rac-erythro-[2-Amino-2-(3,4-dichloro-phenyl)-1-[4-(1,1,2,2-tetrafluoro-ethoxy)-phenyl]-ethanol,
rac-erythro-[2-Amino-2-(3,4-dichloro-phenyl)-1-[4-(tetrahydro-pyran-4-yloxy)-phenyl]-ethanol,
(1R,2S or 1S,2R)-[2-Amino-2-(3,4-dichloro-phenyl)-1-[4-(tetrahydro-pyran-4-yloxy)-phenyl]-ethanol,
rac-erythro-[rac-2-Amino-2-(3,4-dichloro-phenyl)-1-[4-(tetrahydro-furan-3-yloxy)-phenyl]-ethanol,
rac-erythro-[2-Amino-2-(3,4-dichloro-phenyl)-1-hydroxy-ethyl]-phenoxy]-2-chloromethyl-2-methyl-propan-1-ol hydrochloride,
rac-erythro-[2-Amino-2-(3,4-dichloro-phenyl)-1-[4-(1,1-dioxo-hexahydro-1-$\lambda^6$-thiopyran-4-yloxy)-phenyl]-ethanol,
rac-erythro-[2-Amino-2-(3,4-dichloro-phenyl)-1-[4-(tetrahydro-pyran-4-ylmethoxy)-phenyl]-ethanol,
rac-erythro-[1-(4-[4-[2-Amino-2-(3,4-dichloro-phenyl)-1-hydroxy-ethyl]-phenoxy]-piperidin-1-yl)-ethanone,
rac-erythro-[2-Amino-2-(3,4-dichloro-phenyl)-1-[4-(2,2,2-trifluoro-ethoxy)-phenyl]-ethanol,
rac-erythro-[2-Amino-2-(4-chloro-phenyl)-1-(4-cyclopentyloxy-phenyl)-ethanol hydrochloride,
rac-erythro-[2-Amino-1-(4-cyclopropylmethoxy-phenyl)-2-(3,4-dichloro-phenyl)-ethanol,
rac-erythro-2-Amino-2-(3,4-dichloro-phenyl)-1-(4-isobutoxy-phenyl)-ethanol,
rac-erythro-2-Amino-1-(4-sec-butoxy-phenyl)-2-(3,4-dichloro-phenyl)-ethanol,
rac-erythro-2-Amino-2-(3,4-dichloro-phenyl)-1-[4-(3,3,3-trifluoro-propoxy)-phenyl]-ethanol,
rac-erythro-2-Amino-2-(4-chloro-phenyl)-1-(4-cyclohexyloxy-phenyl)-ethanol,
rac-erythro-[2-Amino-2-(3-chloro-4-methyl-phenyl)-1-[4-(tetrahydro-pyran-4-yloxy)-phenyl]-ethanol, and
rac-erythro-[2-Amino-2-(3-chloro-4-methyl-phenyl)-1-[4-(tetrahydro-pyran-4-yloxy)-phenyl]-ethanol,
or pharmaceutically active salts or esters thereof.

One further embodiment of the invention provides compounds selected from the group consisting of
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
(1R,2S or 1S,2R)-[2-Amino-2-(3,4-dichloro-phenyl)-1-[4-(tetrahydro-pyran-4-yloxy)-phenyl]-ethanol,
rac-erythro-[2-Amino-2-(3,4-dichloro-phenyl)-1-[2-fluoro-4-(3-methyl-oxetan-3-ylmethoxy)-phenyl]-ethanol,
rac-erythro-[2-Amino-2-(3,4-dichloro-phenyl)-1-[2-fluoro-4-(tetrahydro-pyran-4-yloxy)-phenyl]-ethanol hydrochloride,
rac-erythro-[rac-2-Amino-2-(3,4-dichloro-phenyl)-1-[2-fluoro-4-(tetrahydro-furan-3-yloxy)-phenyl]-ethanol hydrochloride,
rac-erythro-[2-Amino-2-(3,4-dichloro-phenyl)-1-[2-methyl-6-(tetrahydro-pyran-4-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[2-Amino-2-(3,4-dichloro-phenyl)-1-[4-(tetrahydro-pyran-4-yloxy)-phenyl]-ethanol,
rac-erythro-[rac-2-Amino-2-(3,4-dichloro-phenyl)-1-[4-(tetrahydro-furan-3-yloxy)-phenyl]-ethanol,
rac-erythro-[2-Amino-2-(3,4-dichloro-phenyl)-1-hydroxy-ethyl]-phenoxy]-2-chloromethyl-2-methyl-propan-1-ol hydrochloride, rac-erythro-2-Amino-2-(4-chloro-phenyl)-1-[4-(tetrahydro-pyran-4-yloxy)-phenyl]-ethanol, rac-erythro-[rac-2-Amino-2-(3,4-dichloro-phenyl)-1-[6-(tetrahydro-furan-3-yloxy)-pyridin-3-yl]-ethanol dihydrochloride, rac-erythro-[2-Amino-2-(3,4-dichloro-phenyl)-1-[4-(1,1-dioxo-hexahydro-1-$\lambda^6$-thiopyran-4-yloxy)-phenyl]-ethanol, rac-erythro-[2-Amino-2-(3,4-dichloro-phenyl)-1-[3,5-difluoro-4-(tetrahydro-pyran-4-yloxy)-phenyl]-ethanol hydrochloride, and rac-erythro-[2-Amino-2-(3,4-dichloro-phenyl)-1-[4-methyl-6-(tetrahydro-pyran-4-yloxy)-pyridin-3-yl]-ethanol dihydrochloride, or pharmaceutically active salts or esters thereof.

One further embodiment of the invention is a process for preparing a compound of formula I as defined in any of the embodiments which process comprises:

deprotecting a compound of formula XXXV to a compound of formula I

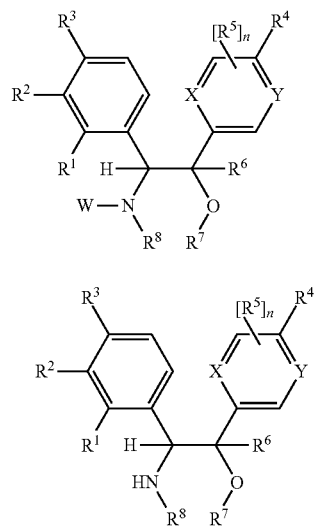

wherein $R^1$, $R^2$, $R^3$, $R^4$, $R^5$, $R^6$, $R^7$, $R^8$, n, X and Y are as defined in any of the embodiments, and W is BOC, Fmoc, Cbz, trifluoroacetyl, Bn, Ac, Tr or Ts.

One further embodiment of the invention is a compound as defined in any of the embodiments, whenever prepared by a process as defined above.

One further embodiment of the invention is a compound as defined in any of the embodiments for use as a medicament.

One further embodiment of the invention is a compound as defined in any of the embodiments for use for the treatment or prevention of a disorder or condition mediated by the glycine transporter 1, or that can be treated via inhibition of the glycine transporter 1.

One further embodiment of the invention is a compound as defined in any of the embodiments for use for the treatment of psychoses, dysfunction in memory and learning, schizophrenia, dementia, attention deficit disorders or Alzheimer's disease.

One further embodiment of the invention is a medicament, comprising a compound as defined in any of the embodiments.

One further embodiment of the invention is a pharmaceutical composition comprising a compound as defined in any of the embodiments as an active ingredient and a carrier and/or a pharmaceutically acceptable auxiliary substance.

One further embodiment of the invention is a pharmaceutical composition, comprising a compound as defined in any of the embodiments for the treatment or prevention of a disorder or condition mediated by the glycine transporter 1, or that can be treated via inhibition of the glycine transporter 1.

One further embodiment of the invention is a pharmaceutical composition, comprising a compound as defined in any of the embodiments for the treatment of psychoses, dysfunction in memory and learning, schizophrenia, dementia, attention deficit disorders or Alzheimer's disease.

One further embodiment of the invention is the use of a compound as defined in any of the embodiments for the manufacture of a medicament for the treatment or prevention of a disorder or condition mediated by the glycine transporter 1, or that can be treated via inhibition of the glycine transporter 1.

One further embodiment of the invention is the use of a compound as defined in any of the embodiments for the manufacture of a medicament for the treatment of psychoses, dysfunction in memory and learning, schizophrenia, dementia, attention deficit disorders or Alzheimer's disease.

One further embodiment of the invention is the use of a compound as defined in any of the embodiments for the treatment or prevention of a disorder or condition mediated by the glycine transporter 1, or that can be treated via inhibition of the glycine transporter 1.

One further embodiment of the invention is the use of a compound as defined in any of the embodiments for the treatment of psychoses, dysfunction in memory and learning, schizophrenia, dementia, attention deficit disorders or Alzheimer's disease.

One further embodiment of the invention is a method for the therapeutic and/or prophylactic treatment of a disorder or condition mediated by the glycine transporter 1, or that can be treated via inhibition of the glycine transporter 1, particularly for the treatment of psychoses, dysfunction in memory and learning, schizophrenia, dementia, attention deficit disorders or Alzheimer's disease, which method comprises administering a compound as defined in any of the embodiments to a mammal, particularly to a human being.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The compounds of formula I can be prepared in accordance with the following schemes. The starting material is commercially available or can be prepared in accordance with known methods. Any previously defined residues and variables will continue to have the previously defined meaning unless otherwise indicated.

Scheme 1: Preparation of Weinreb-type amides IV (Intermediates 1-11)

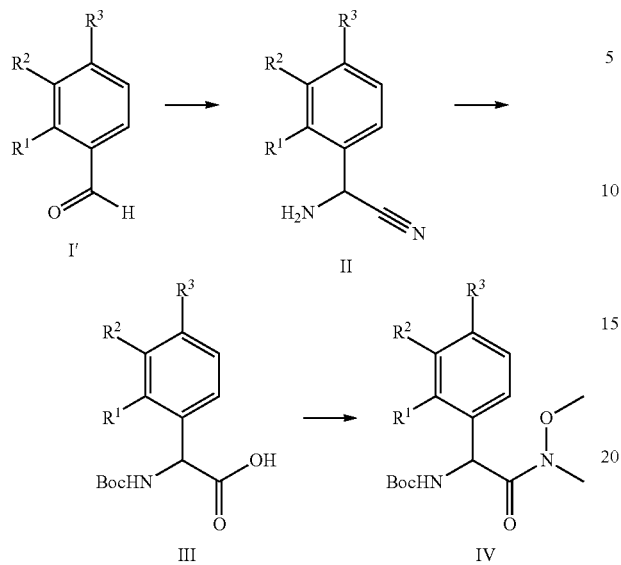

The Weinreb-type amides have been prepared from the corresponding aldehyde (I') following methods known in the art. The aldehyde is treated with ammonia in a low alcohol, preferred is methanol, in presence of tetraisopropyl orthotitanate followed by treatment of the intermediate with a cyanide derivative, preferred is trimethylsilyl cyanide. The amino nitrile (II) is hydrolyzed by heating to reflux a solution of the starting material in conc mineral acid, preferred is conc. hydrochloric acid, to the amino acid (III). The amino acid is N-protected, usually with a tert-butyloxycarbonyl group, and finally condensed with N,O-dimethylhydroxylamine to furnish the Weinreb amide (IV).

Scheme 2: Preparation of diaryl derivatives VII (Intermediate 12)

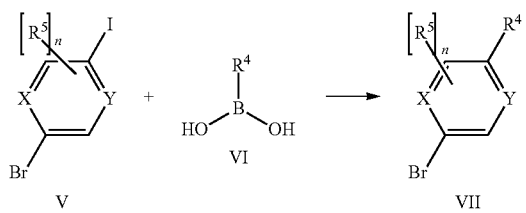

The Diaryl derivatives (VII) have been prepared by Suzuki type reactions following procedures known in the art.

Scheme 3: Preparation of alkoxy(het)arenes IX (Intermediate 13-32)

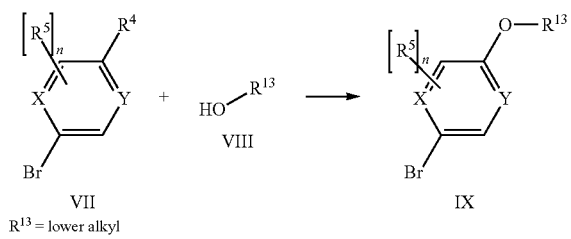

$R^{13}$ = lower alkyl

The alkoxy(het)arenes (IX) are prepared by a Mitsunobu type reaction following procedures known in the art.

Scheme 4: Preparation of amino alcohols XIII Intermediate 33

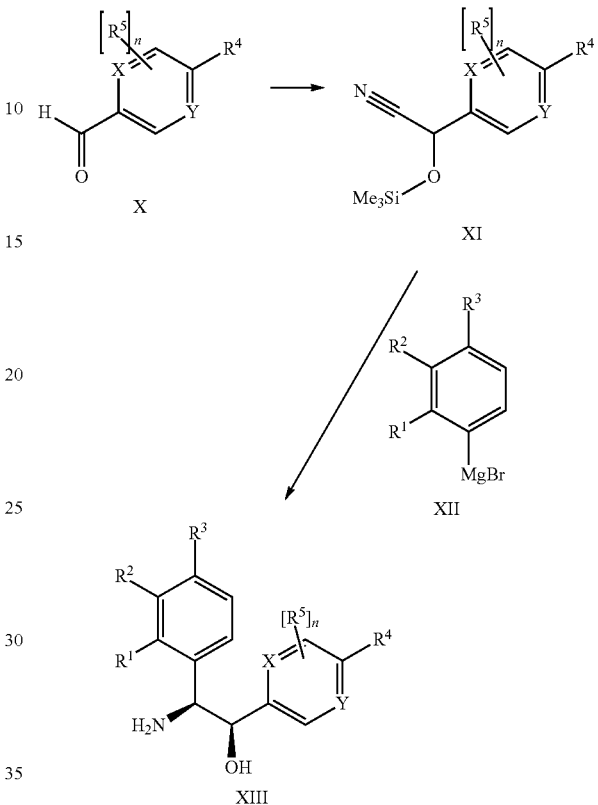

The amino alcohols (XIII) where prepared by cyanosilation of the aldehyde (X) followed by coupling with a Grignard reagent (XII) following procedures known in the art.

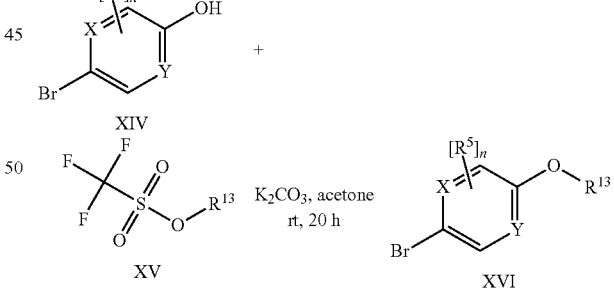

$R^{13}$ is lower alkyl, optionally substituted by halogen, hydroxyl, cycloalkyl, heterocyclyl, lower alkyl or lower alkyl substituted by halogen or hydroxyl.

Scheme 5: Preparation of Fluorinated Alkoxyarenes XVI (Intermediates 34-35)

Alkoxy-arenes (XVI) derived from fluorinated alcohols are prepared by condensation of the corresponding phenol (XIV) with an activated alcohol (XV), usually its triflate, with in presence of a base, usually potassium carbonate, in a solvent like acetone. The procedure is well documented in the art.

Scheme 6: Preparation of amino-alcohols XX-route 1

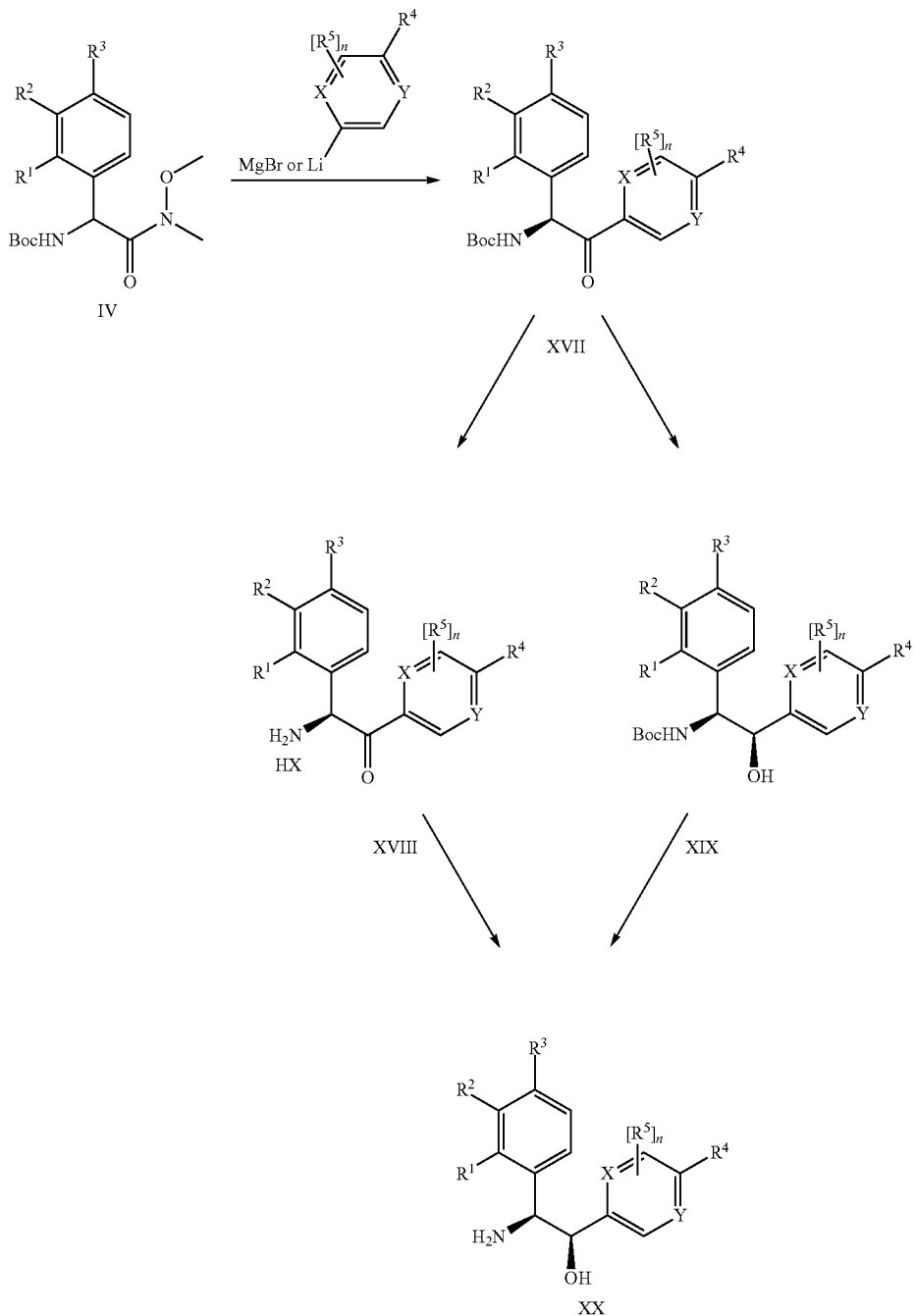

The synthesis of the amino-alcohols (XX) starts with addition of an aryl lithium or aryl magnesium halide to the corresponding Weinreb type amide (IV) leading to an N-protected amino ketone (XVII). This is either reduced with e.g. sodium borohydride in methanol at ambient temperature to the racemic erythro N-protected amino alcohol (XIX) which is deprotected under acidic conditions, usually with trifluoroacetic acid in dichloromethane or hydrogen chloride in 1,4-dioxane at 0° C. to ambient temperature to the final compound (XX), or the ketone (XVII) is deprotected to the amino ketone (XVIII) with hydrogen chloride in ethanol and/or in methanol (isolated as stable hydrochloride) or with trifluoroacetic acid in dichloromethane (isolated as stable triflate) which is then reduced with e.g. sodium borohydride in methanol to the final product (XX). The reaction sequence applies procedures known in the art.

Scheme 7: Preparation of amino-alcohols XX- route 2
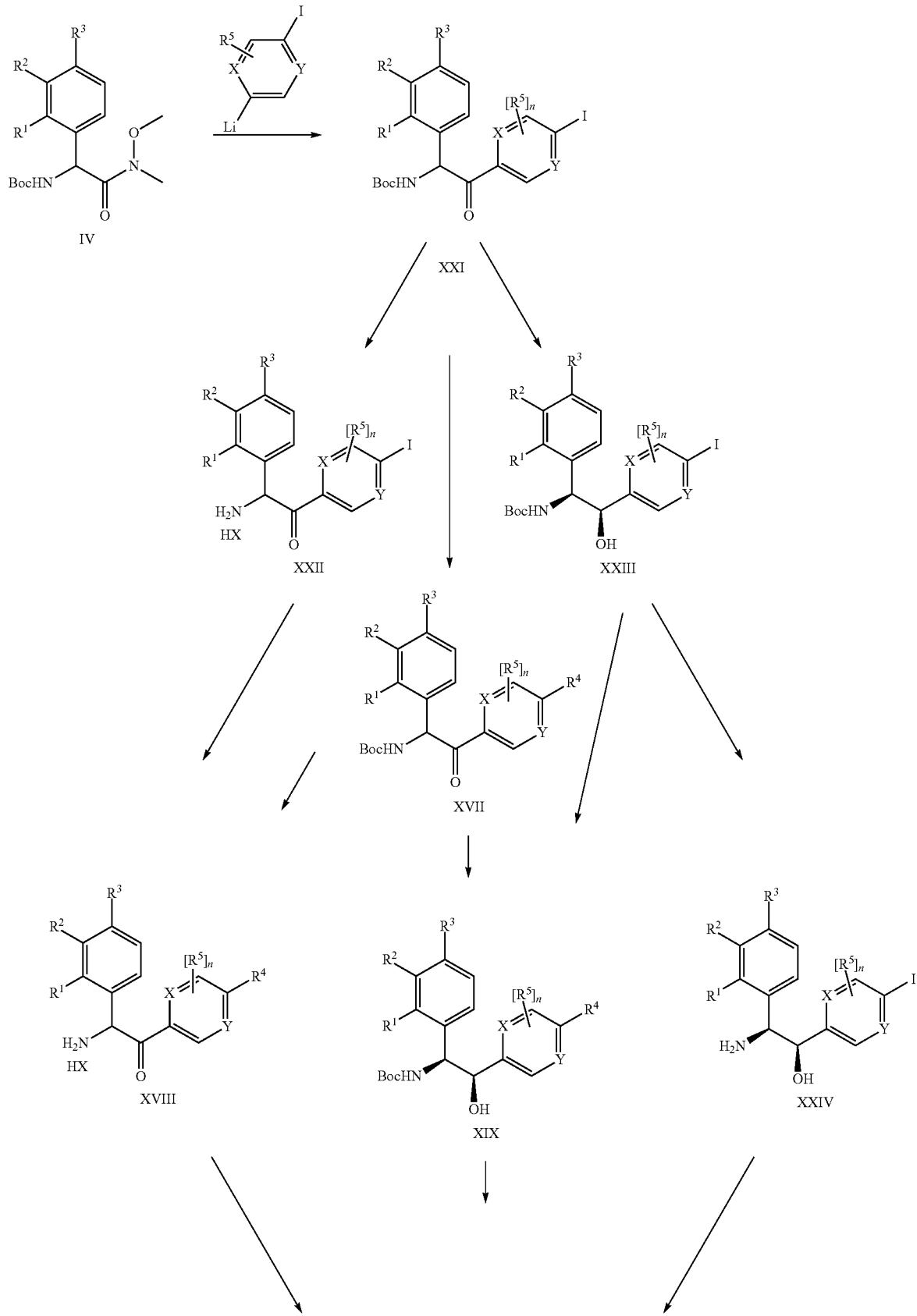

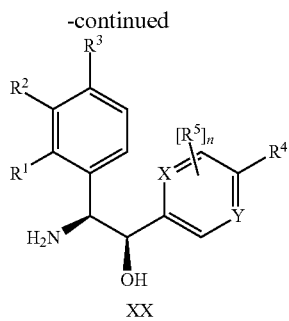

Another approach to the final compounds (XX) starts with a 4-halogenated aryl ketone (XXI), usually a 4-iodoaryl ketone prepared by reaction of a 1-lithio-4-iodoaryl, prepared from 1,4-diiodobenzene and butyl lithium in THF at −78° C., with the corresponding Weinreb type amide (IV). From this intermediate (XXI) the final amino-alcohol (XX) is accessed via three routes.

Firstly reduction of the N-protected amino-ketone (XXI) leads to an N-protected amino-alcohol (XXIII) which is either reacted with a boronic acid or an ester derivative thereof in a Suzuki type reaction to the biaryl compound (XIX) which is then deprotected to the final compound (XX) or the N-protected amino-alcohol (XXIII) is deprotected and the resulting 4-iodo-aryl amino-alcohol (XXIV) is subjected to a Suzuki type arylation providing the final product (XX).

Secondly the deprotection of the N-protected amino-ketone (XXI) leads to the amino-ketone (XXII), isolated as its hydrochloride or trifluoroacetate, which is subjected to a Suzuki type reaction leading to a biaryl-amino-ketone (XVIII) which is reduced to the final product (XX).

Thirdly the Suzuki type reaction is applied on the N-protected 4-iodo-aryl amino-ketone (XXI) leading to the N-protected biaryl-amino-ketone (XVII) which either is reduced to the N-protected amino-alcohol (XIX) which also is obtained via the first route or is deprotected to the biaryl-amino-ketone (XVIII) which also is obtained via the second route. Deprotection or reduction of these intermediates (XIX or XVIII) finally leads to the target compound (XX).

Scheme 8: Preparation of Alkoxy(het)aryl derivatives

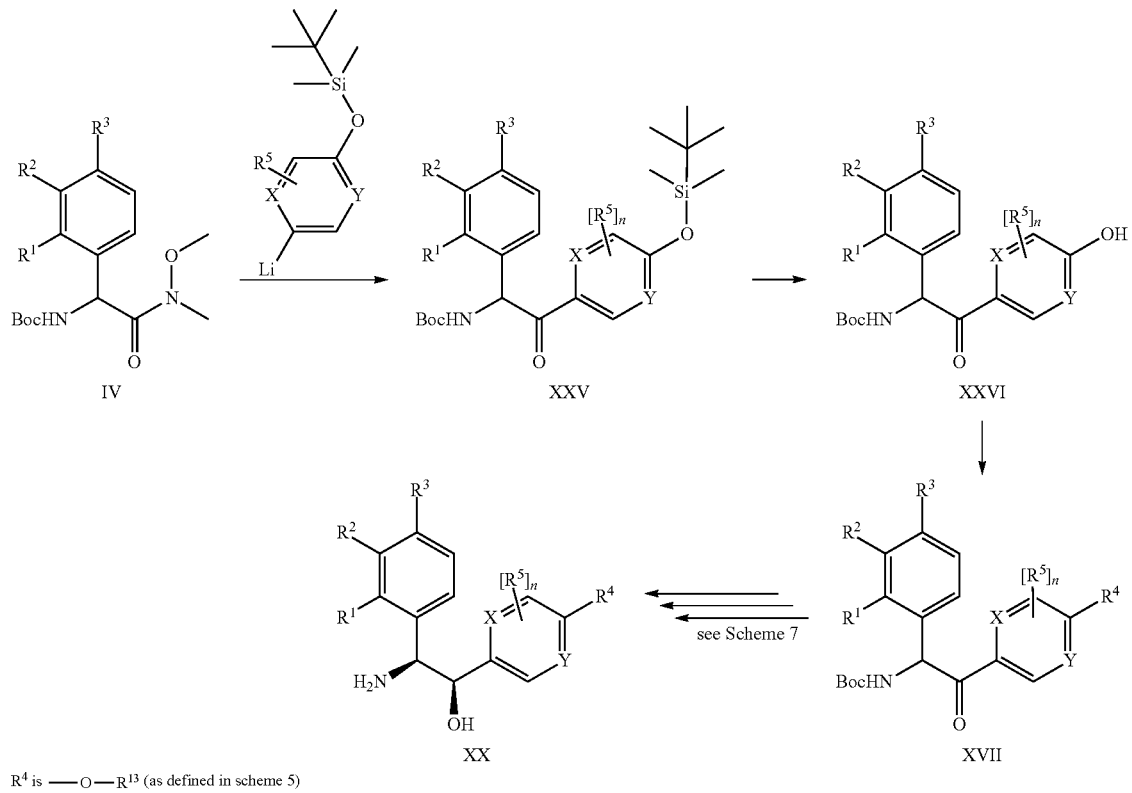

$R^4$ is ——O—$R^{13}$ (as defined in scheme 5)

Reaction of the Weinreb type amide (IV) with an O-silyl protected 1-halo(het)aryl phenol with butyl lithium in THF following described procedure yields the O-silylated N-protected amino-aryl-ketone (XXV) which is selectively deprotected with tetrabutylammonium fluoride in tetrahydrofuran to the phenol (XXVI) which is treated with an alcohol under Mitsunobu type conditions to provide the corresponding aryl ether (XVII). The amino-alcohols (XX) are obtained following the reaction sequences already discussed.

iodide. The N-alkylated protected product (XXX) is treated with hydrogen chloride in methanol at ambient to reflux temperature, preferred is 50° C., for 2 to 24 hours, preferred are 20 hours, which provides the N-alkylated amino-alcohols (XXXI).

Scheme 9: Preparation of tertiary alcohols and N-alkylated amino-alcohols

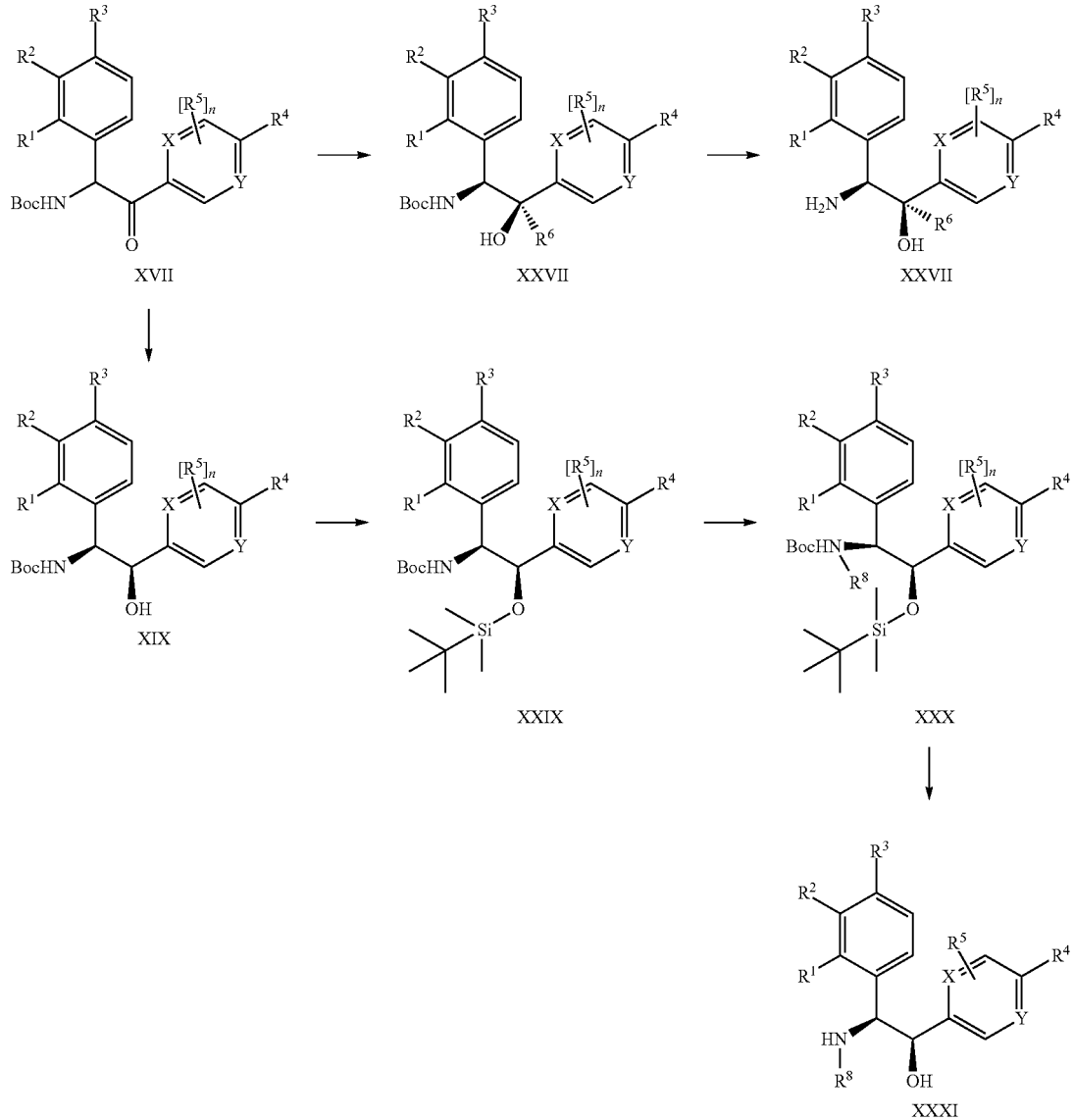

The tertiary alcohols (XXVIII) are obtained by reaction of the N-protected amino-ketone (XVII) with a low alkyl-magnesium chloride, low alkyl-magnesium bromide or low alkyl-magnesium iodide in tetrahydrofuran following procedures known in the art. Deprotection leads to the final product (XXVIII).

Reduction of the N-protected amino-ketone (XVII) with sodium borohydride in methanol at ambient temperature leads to the N-protected amino-alcohol (XIX). In the latter (XXIX) the alcohol group is protected by silylation, preferred is the tert-butyl-dimethylsilyl group. The double protected amino-alcohol is deprotonated with a strong base, preferred is sodium hydride, in an inert solvent like tetrahydrofuran at ambient temperature followed by addition of an alkylation agent like low alkyl halide, preferred is methyl iodide or ethyl Scheme 10: Preparation of the amino-alkoxy compounds

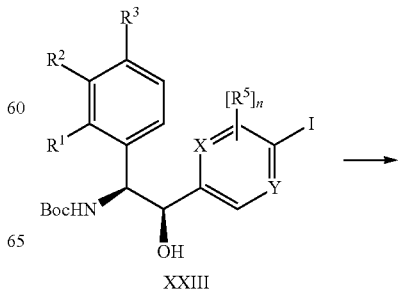

67

-continued

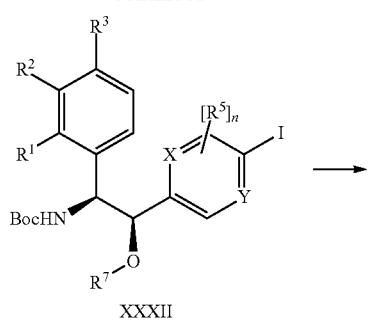

XXXII

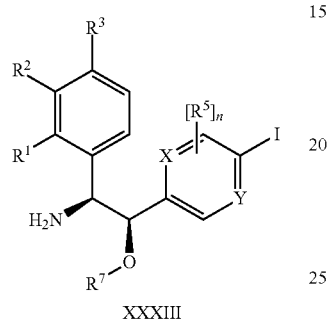

XXXIII

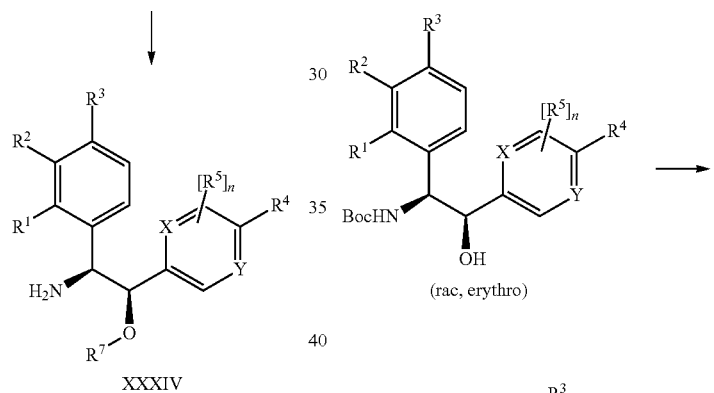

XXXIV

Treatment of the N-protected amino alcohol (XXIII) with a strong base, e.g. sodium hydride, and an alkylating agent like low alkyl halide, preferred are methyl iodide and ethyl iodide, in an inert solvent like tetrahydrofuran results in a N-protected alkoxy-amine (XXXII) which then can be further elaborated to the final amino-alkoxy compound (XXXIV).

Scheme 11: Examples of separation of stereomeric mixtures by chromatography on chiral stationary phase: possible at different steps in the synthesis

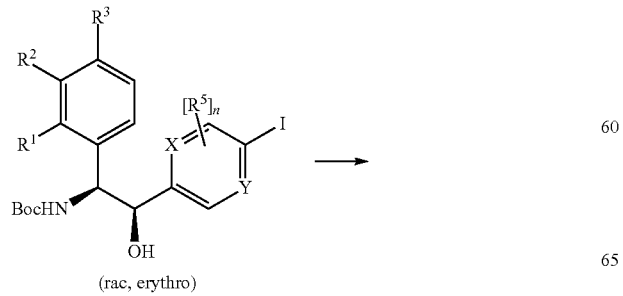
(rac, erythro)

68

-continued

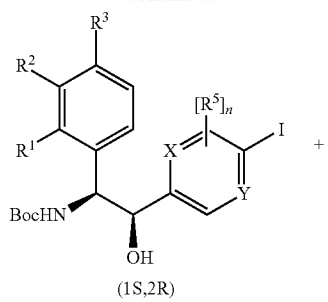
(1S,2R)

+

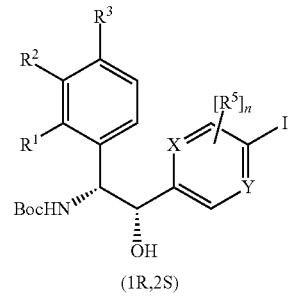
(1R,2S)

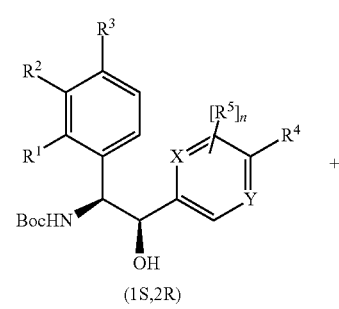
(rac, erythro)

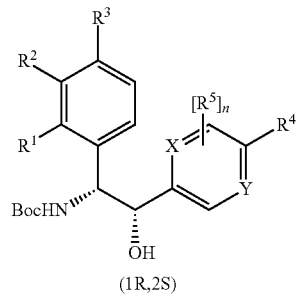
(1S,2R)

+

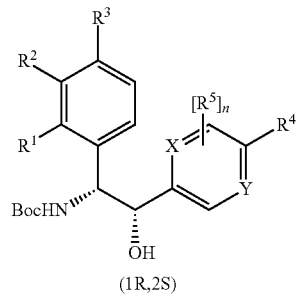
(1R,2S)

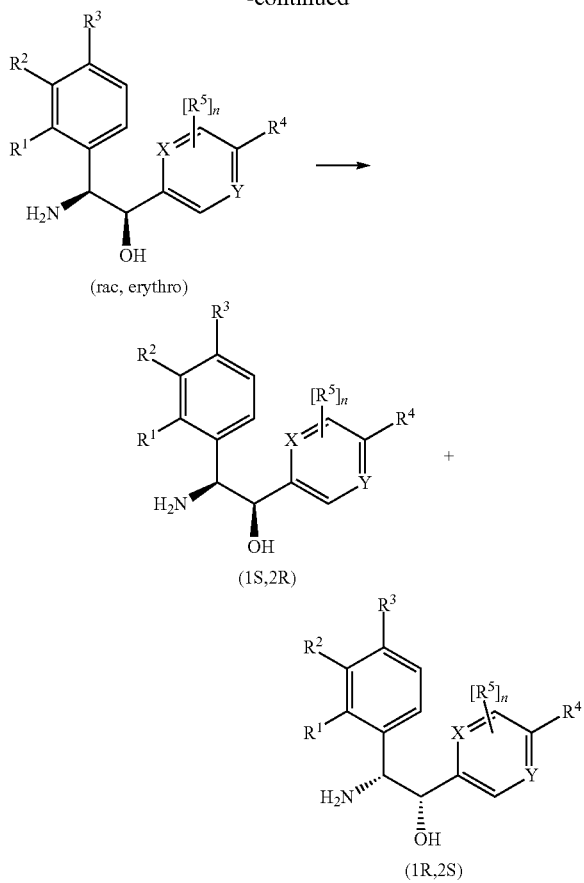

(rac, erythro)

(1S,2R)

(1R,2S)

Separation of the racemic mixtures was performed by chromatography on a chiral stationary phase, e.g. on a Chiralcel OD or a Chiralpak AD column, with an eluent compatible with the stationary phase like a hydrocarbon as pentanes, hexanes or heptanes mixed with a low alcohol as ethanol, n-propanol or isopropanol, preferred are heptane/isopropanol or heptane/ethanol mixtures.

It will be appreciated that the compounds of general formula I in this invention can be derivatized at functional groups to provide derivatives which are capable of conversion back to the parent compound in vivo.

EXPERIMENTAL PART

Preparation of Intermediates

Intermediate 1 rac-[(4-Chloro-3-fluoro-phenyl)-(methoxy-methyl-carbamoyl)-methyl]-carbamic acid tert-butyl ester a) rac-Amino-(4-chloro-3-fluoro-phenyl)-acetonitrile To a solution of 25.0 g (158 mmol) 4-chloro-3-fluorobenzaldehyde in 130 ml methanol and 175 ml methanol saturated with ammonia were added 54.9 ml (52.7 g, 185 mmol) tetraisopropyl orthotitanate and the mixture stirred at ambient temperature for 1.5 hours. Then 20.35 ml (16.14 g, 163 mmol) trimethylsilyl cyanide were added drop-wise and the resulting mixture stirred at ambient temperature for further 2 hours. The reaction mixture was poured onto 1500 ml iced water and extracted with ethyl acetate. The combined organic phases were washed with brine, dried over $Na_2SO_4$ and evaporated. The crude product was purified by flash-chromatography on silica gel with a gradient of heptane and 0 to 50% ethyl acetate. rac-Amino-(4-chloro-3-fluoro-phenyl)-acetonitrile was obtained as orange oil: MS (ISN): 183.2 (M−H)⁻.

b) rac-Amino-(4-chloro-3-fluoro-phenyl)-acetic acid hydrochloride

A mixture of 11.1 g (60 mmol) rac-amino-(4-chloro-3-fluoro-phenyl)-acetonitrile in 400 ml 37% aqueous hydrochloric acid was heated to 100° C. for 20 hours. Then the reaction mixture was evaporated, the residue taken up in water and again evaporated: rac-amino-(4-chloro-3-fluoro-phenyl)-acetic acid hydrochloride was obtained as light yellow solid: MS (ISP): 202.2 (M+H)⁺.

c) rac-tert-Butoxycarbonylamino-(4-chloro-3-fluoro-phenyl)-acetic acid

To a suspension of 14.4 g (60 mmol) rac-amino-(4-chloro-3-fluoro-phenyl)-acetic acid hydrochloride in 192 ml dioxane and 96 ml water were added 120 ml (120 mmol) 1N NaOH. The mixture was cooled to 0° C., 16.6 g (90 mmol) di-tert.-butyl dicarbonate and 5.04 g (60 mmol) sodium bicarbonate added and then stirred at ambient temperature for 20 h. The reaction mixture was concentrated to 50% of initial volume, ethyl acetate added and with 1N potassium hydrogen sulfate the pH adjusted to 2.5 to 3. The organic phase was separated and the aqueous extracted twice with ethyl acetate. The combined organic phases were washed with brine, dried over $Na_2SO_4$ and evaporated: 18.2 g rac-tert-butoxycarbonylamino-(4-chloro-3-fluoro-phenyl)-acetic acid as oily residue which crystallized on standing: MS (ISN): 302.2 (M−H)⁻.

d) rac-[(4-Chloro-3-fluoro-phenyl)-(methoxy-methyl-carbamoyl)-methyl]-carbamic acid tert-butyl ester To a solution of 6.00 g (19.76 mmol) rac-tert-butoxycarbonylamino-(4-chloro-3-fluoro-phenyl)-acetic acid in 146 ml dimethylformamide were added 20.71 ml (118.6 mmol) N-ethyl-diisopropylamine, 2.07 g (20.75 mmol) N,O-dimethylhydroxylamine hydrochloride and 8.26 g (24.70 mmol) 0-(1H-benzotriazol-1-yl)-N,N,N',N'-tetramethyluronium tetrafluoroborate (TBTU) and the solution stirred at ambient temperature for 30 min. The reaction mixture was diluted with water and the resulting suspension stirred for 15 min. The precipitate was filtered and washed with water and dried: 5.18 g rac-[(4-chloro-3-fluoro-phenyl)-(methoxy-methyl-carbamoyl)-methyl]-carbamic acid tert-butyl ester as colorless solid: MS (ISP): 347.2 (M+H)⁺ and 247.1 ((M-Boc)+H)⁺ (100%).

Intermediate 2 rac-[(4-Chloro-3-methyl-phenyl)-(methoxy-methyl-carbamoyl)-methyl]-carbamic acid tert-butyl ester a) rac-Amino-(4-chloro-3-methyl-phenyl)-acetonitrile The title compound was prepared from 4-chloro-3-methyl-benzaldehyde in analogy to intermediate 1a): MS (ISN): 179.1 (M−H)⁻.

b) rac-Amino-(4-chloro-3-methyl-phenyl)-acetic acid hydrochloride

The title compound rac-Amino-(4-chloro-3-methyl-phenyl)-acetic acid hydrochloride was prepared from rac-amino-(4-chloro-3-methyl-phenyl)-acetonitrile in analogy to intermediate 1b): MS (ISN): 198.3 (M−H)⁻.

c) rac-tert-Butoxycarbonylamino-(4-chloro-3-methyl-phenyl)-acetic acid

The title compound was prepared from rac-amino-(4-chloro-3-methyl-phenyl)-acetic acid hydrochloride in analogy to intermediate 1c): MS (ISN): 298.1 (M−H)⁻.

d) rac-[(4-Chloro-3-methyl-phenyl)-(methoxy-methyl-carbamoyl)-methyl]-carbamic acid tert-butyl ester The title compound was prepared from rac-tert-butoxycarbonylamino-(4-chloro-3-methyl-phenyl)-acetic acid in analogy to intermediate 1d): MS (ISP): 343.2 (M+H)⁺.

Intermediate 3 rac-[(4-Chloro-2-fluoro-phenyl)-(methoxy-methyl-carbamoyl)-methyl]-carbamic acid tert-butyl ester a) rac-Amino-(4-chloro-2-fluoro-phenyl)-acetonitrile The title compound was prepared from 4-chloro-2-fluoro-benzaldehyde in analogy to intermediate 1a): MS (ISN): 182.9 (M−H)⁻.

b) rac-Amino-(4-chloro-2-fluoro-phenyl)-acetic acid hydrochloride

The title compound was prepared from rac-amino-(4-chloro-2-fluoro-phenyl)-acetonitrile in analogy to intermediate 1b): MS (ISN): 202.4 (M−H)⁻.

c) rac-tert-Butoxycarbonylamino-(4-chloro-2-fluoro-phenyl)-acetic acid

The title compound was prepared from rac-amino-(4-chloro-2-fluoro-phenyl)-acetic acid hydrochloride in analogy to intermediate 1c): MS (ISN): 302.3 (M−H)⁻.

d) rac-[(4-Chloro-2-fluoro-phenyl)-(methoxy-methyl-carbamoyl)-methyl]-carbamic acid tert-butyl ester The title compound was prepared from rac-tert-butoxycarbonylamino-(4-chloro-2-fluoro-phenyl)-acetic acid in analogy to intermediate 1d): MS (ISP): 347.3 (M+H)⁺.

Intermediate 4 rac-[(3-Chloro-4-methyl-phenyl)-(methoxy-methyl-carbamoyl)-methyl]-carbamic acid tert-butyl ester a)
rac-Amino-(3-chloro-4-methyl-phenyl)-acetonitrile The title compound was prepared from 4-chloro-3-methyl-benzaldehyde in analogy to intermediate 1a): orange solid.

b) rac-Amino-(3-chloro-4-methyl-phenyl)-acetic acid hydrochloride

The title compound was prepared from rac-amino-(3-chloro-4-methyl-phenyl)-acetonitrile in analogy to intermediate 1b): colorless solid.

c) rac-tert-Butoxycarbonylamino-(3-chloro-4-methyl-phenyl)-acetic acid

The title compound was prepared from rac-amino-(3-chloro-4-methyl-phenyl)-acetic acid hydrochloride in analogy to intermediate 1c): MS (ISN): 298.3 (M−H)⁻.

d) rac-[(3-Chloro-4-methyl-phenyl)-(methoxy-methyl-carbamoyl)-methyl]-carbamic acid tert-butyl ester The title compound was prepared from rac-tert-butoxycarbonylamino-(3-chloro-4-methyl-phenyl)-acetic acid in analogy to intermediate 1d): off-white solid.

Intermediate 5 rac-[(3-Fluoro-4-trifluoromethyl-phenyl)-(methoxy-methyl-carbamoyl)-methyl]-carbamic acid tert-butyl ester a) rac-Amino-(3-fluoro-4-trifluoromethyl-phenyl)-acetonitrile The title compound was prepared from 3-fluoro-4-(trifluoromethyl)benzaldehyde in analogy to Intermediate 1a): MS (ISN): 217.3 (M−H)⁻.

b) rac-Amino-(3-fluoro-4-trifluoromethyl-phenyl)-acetic acid hydrochloride

The title compound was prepared from rac-amino-(3-fluoro-4-trifluoromethyl-phenyl)-acetonitrile in analogy to intermediate 1b): MS (ISN): 236.2 (M−H)⁻.

c) rac-tert-Butoxycarbonylamino-(3-chloro-4-methyl-phenyl)-acetic acid

The title compound was prepared from rac-amino-(3-fluoro-4-trifluoromethyl-phenyl)-acetic acid hydrochloride in analogy to the intermediate compound 1c): MS (ISN): 292.3 ((M—CO₂)−H)⁻.

d) rac-[(3-Fluoro-4-trifluoromethyl-phenyl)-(methoxy-methyl-carbamoyl)-methyl]-carbamic acid tert-butyl ester The title compound was prepared from rac-tert-butoxycarbonylamino-(3-fluoro-4-trifluoromethyl-phenyl)-acetic acid in analogy to intermediate 1d): MS (ISP): 381.1 (M+H)⁺.

Intermediate 7 rac-[(3-Fluoro-4-methyl-phenyl)-(methoxy-methyl-carbamoyl)-methyl]-carbamic acid tert-butyl ester a) rac-tert-Butoxycarbonylamino-(3-fluoro-4-methyl-phenyl)-acetic acid The title compound was prepared from rac-amino-(3-fluoro-4-methyl-phenyl)-acetic acid hydrochloride in analogy to intermediate 1c): MS (ISN): 282.0 (M−H)⁻.

b) rac-[(3-Fluoro-4-methyl-phenyl)-(methoxy-methyl-carbamoyl)-methyl]-carbamic acid tert-butyl ester The title compound was prepared from rac-tert-butoxycarbonylamino-(3-fluoro-4-methyl-phenyl)-acetic acid in analogy to intermediate 1d): MS (ISP): 327.1 (M+H)$^+$.

Intermediate 8 rac-[(4-Chloro-phenyl)-(methoxy-methyl-carbamoyl)-methyl]-carbamic acid tert-butyl ester The title compound was prepared from rac-tert-butoxycarbonylamino-(4-chloro-phenyl)-acetic acid in analogy to intermediate 1d): MS (ISP): 329.1 (M+H)$^+$.

Intermediate 9 rac-[(3,4-Dichloro-phenyl)-(methoxy-methyl-carbamoyl)-methyl]-carbamic acid tert-butyl ester The title compound was prepared from rac-tert-butoxycarbonylamino-(3,4-dichloro-phenyl)-acetic acid in analogy to intermediate 1d): MS (ISP): 363.1 (M+H)$^+$.

Intermediate 10 rac-[(Methoxy-methyl-carbamoyl)-(4-trifluoromethyl-phenyl)-methyl]-carbamic acid tert-butyl ester The title compound was prepared from rac-tert-butoxycarbonylamino-(4-trifluoromethyl-phenyl)-acetic acid in analogy to intermediate 1d): MS (ISP): 363.4 (M+H)$^+$.

Intermediate 12

3-(4-Bromo-2-methyl-phenyl)-5-fluoro-pyridine

The title compound was prepared from 5-bromo-2-iodotoluene and 5-fluoropyridine-3-boronic acid in analogy to Example 1b): MS (ISP): 265.8 and 267.9 (M+H)$^+$.

Intermediate 13 rac-3-Bromo-2-methyl-6-(tetrahydro-furan-3-yloxy)-pyridine

The title compound was prepared from 3-bromo-6-hydroxy-2-methylpyridine and rac-3-hydroxy-tetrahydrofuran in analogy to Example 9c): colorless solid.

Intermediate 14 rac-3-(4-Bromo-3-fluoro-phenoxy)-tetrahydro-furan

The title compound was prepared from 4-bromo-3-fluorophenol and rac-3-hydroxy-tetrahydrofuran in analogy to Example 9c): MS (EI): 260 and 262 M$^+$.

Intermediate 15

3-Bromo-2-methyl-6-(tetrahydro-pyran-4-yloxy)-pyridine

The title compound was prepared from 3-bromo-6-hydroxy-2-methylpyridine and tetrahydro-4H-pyran-4-ol in analogy to Example 9c): colorless solid.

Intermediate 16

4-(4-Bromo-2-fluoro-phenoxy)-tetrahydro-pyran

The title compound was prepared from 4-bromo-2-fluorophenol and tetrahydro-4H-pyran-4-ol in analogy to Example 9c): MS (EI): 274 and 276 M$^+$.

Intermediate 17 rac-5-Bromo-2-(tetrahydro-furan-3-yloxy)-pyridine

The title compound was prepared from 5-bromo-2-hydroxypyridine and rac-3-hydroxy-tetrahydrofuran in analogy to Example 9c): colorless solid.

Intermediate 18

4-(4-Bromo-2,6-difluoro-phenoxy)-tetrahydro-pyran

The title compound was prepared from 4-bromo-2,6-difluorophenol and tetrahydro-4H-pyran-4-ol in analogy to Example 9c): MS (EI): 292 and 294 M$^+$.

Intermediate 19

5-Bromo-4-methyl-2-(tetrahydro-pyran-4-yloxy)-pyridine

The title compound was prepared from 5-bromo-2-hydroxy-4-methylpyridine and tetrahydro-4H-pyran-4-ol in analogy to Example 9c): colorless solid.

Intermediate 20

5-Bromo-2-(tetrahydro-pyran-4-yloxy)-pyridine

The title compound was prepared from 5-bromo-2-hydroxypyridine and tetrahydro-4H-pyran-4-ol in analogy to Example 9c): colorless solid.

Intermediate 21 rac-2-Bromo-5-(tetrahydro-furan-3-yloxy)-pyridine

The title compound was prepared from 2-bromo-5-hydroxypyridine and rac-3-hydroxy-tetrahydrofuran in analogy to Example 9c): MS (EI): 243 and 245 M$^+$.

Intermediate 22 rac-5-Bromo-4-methyl-2-(tetrahydro-furan-3-yloxy)-pyridine

The title compound was prepared from 5-bromo-2-hydroxy-4-methylpyridine and rac-3-hydroxy-tetrahydrofuran in analogy to Example 9c): colorless liquid.

Intermediate 23

2-Bromo-5-(tetrahydro-pyran-4-yloxy)-pyridine

The title compound was prepared from 5-bromo-5-hydroxypyridine and tetrahydro-4H-pyran-4-ol in analogy to Example 9c): MS (ISP): 258.0 and 259.9 (M+H)$^+$.

Intermediate 24

5-Bromo-3-methyl-2-(tetrahydro-pyran-4-yloxy)-pyridine

The title compound was prepared from 5-bromo-2-hydroxy-3-methylpyridine and tetrahydro-4H-pyran-4-ol in analogy to Example 9c): colorless solid.

Intermediate 25

3-Bromo-6-isopropoxy-2-methyl-pyridine

The title compound was prepared from 3-bromo-6-hydroxy-2-methylpyridine and isopropanol in analogy to Example 9c): colorless liquid.

Intermediate 26 rac-2-(4-Bromo-3-fluoro-phenoxymethyl)-tetrahydro-furan

The title compound was prepared from 4-bromo-3-fluorophenol and rac-2-hydroxymethyl-tetrahydrofuran in analogy to Example 9c): MS (EI): 274 and 276 M$^+$.

Intermediate 27 rac-2-(4-Bromo-3-fluoro-phenoxymethyl)-oxetane

The title compound was prepared from 4-bromo-3-fluorophenol and rac-2-hydroxymethyl-oxetane in analogy to Example 9c): MS (EI): 260 and 262 M$^+$.

Intermediate 28

5-Bromo-2-isopropoxy-4-methyl-pyridine

The title compound was prepared from 5-bromo-2-hydroxy-4-methylpyridine and isopropanol in analogy to Example 9c): colorless liquid.

Intermediate 29 rac-5-Bromo-3-methyl-2-(tetrahydro-furan-3-yloxy)-pyridine

The title compound was prepared from 5-bromo-2-hydroxy-4-methylpyridine and rac-3-hydroxymethyl-tetrahydrofuran in analogy to Example 9c): colorless solid.

Intermediate 30

2-Bromo-5-isopropoxy-pyridine

The title compound was prepared from 2-bromo-5-hydroxypyridine and isopropanol in analogy to Example 9c): MS (EI): 215 and 217 M$^+$.

Intermediate 31

4-(4-Bromo-3-fluoro-phenoxy)-tetrahydro-pyran

The title compound was prepared from 4-bromo-3-fluorophenol and tetrahydro-4H-pyran-4-ol in analogy to Example 9c): MS (EI): 274 and 276 M$^+$.

Intermediate 32

3-(4-Bromo-3-fluoro-phenoxymethyl)-3-methyl-oxetane

The title compound was prepared from 4-bromo-3-fluorophenol and (3-methyl-oxetan-3-yl)-methanol in analogy to Example 9c): MS (EI): 274 and 276 M$^+$.

Intermediate 33 rac-erythro-2-Amino-2-(4-chloro-phenyl)-1-(4-iodo-phenyl)-ethanol

A mixture of 4-iodo-benzaldehyde (4.64 g), trimethylsilyl cyanide (2.9 ml, 1.1 eq) and zinc iodide (5 mg, 0.1%) was stirred at room temperature for 30 minutes (exothermic reaction). The reaction mixture was then diluted in THF (40 ml) and a 1 M solution of 4-chlorophenyl-magnesium bromide in diethyl ether (40 ml, 2 eq) was then slowly added to the reaction mixture which was then stirred for another 3 hours at room temperature. The reaction mixture was then cooled down to −78° C., methanol (40 ml) was added followed by sodium borohydride (1.57 g, 2 eq) over 5 minutes. The reaction mixture was then allowed to warm up to room temperature over 4 hours and stirred at room temperature overnight. After such time, a solution of 60 ml of HCl (3M) was added and the reaction mixture was stirred for 2 hours at room temperature. The reaction mixture was then diluted with diethyl ether and the aqueous phase was washed twice with diethyl ether. All the organic extracts were then once more extracted with water and the combined aqueous phases were then neutralized using NaOH (3N) and then basified using a 10% NaHCO3 solution. Finally, the aqueous solution was extracted several times with ethyl acetate and the combined organic extracts were dried over Na$_2$SO$_4$, filtered and concentrated in vacuo. After a couple of rounds of recrystallisation from ethyl acetate and trituration with di-isopropyl ether, the title compound could be isolated as a white solid (7.47 g, 12.6%).

Intermediate 34

1-Bromo-2-fluoro-4-(2,2,3,3,3-pentafluoro-propoxy)-benzene

The title compound was prepared from 4-bromo-3-fluorophenol and 2,2,3,3,3,-pentafluoropropyl triflate with potassium carbonate in acetone at ambient temperature for 18 hours. Kugelrohr distillation provided a colorless oil, b.p. 105-110° C./12 mbar.

Intermediate 35 rac-1-Bromo-4-(2,2,2-trifluoro-1-methyl-ethoxy)-benzene

The title compound was prepared from 4-bromophenol and rac-trifluoro-methanesulfonic acid 2,2,2-trifluoro-1-methyl-

Example 1 rac-erythro-[2-Amino-2-(3,4-dichloro-phenyl)-1-(3-fluoro-3'-methanesulfonyl-biphenyl-4-yl)-ethanol trifluoroacetate

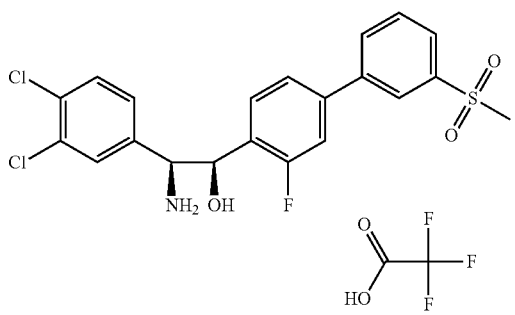 [SMILES: CS(=O)(=O)c1cccc(-c2ccc([C@@H](O)[C@@H](N)c3ccc(Cl)c(Cl)c3)c(F)c2)c1 ; O=C(O)C(F)(F)F]

a) rac-[2-(4-Bromo-2-fluoro-phenyl)-1-(3,4-dichloro-phenyl)-2-oxo-ethyl]-carbamic acid tert-butyl ester To a stirred solution of 1.75 g (5.78 mmol) 1-bromo-3-fluoro-4-iodo-benzene in 12 ml dry tetrahydrofuran were added at –78° C. 3.61 ml (5.78 mmol) of a 1.6M butyl lithium solution in hexanes. After 1 h 0.600 g (1.65 mmol) rac-[(3,4-dichloro-phenyl)-(methoxy-methyl-carbamoyl)-methyl]-carbamic acid tert-butyl ester (Intermediate 9) were added and stirred at –78° C. fur further 4 h. Then the reaction mixture was quenched by addition of saturated aqueous ammonium chloride solution, warmed to ambient temperature and extracted with ethyl acetate. The combined extracts were washed with brine, dried over Na$_2$SO$_4$, filtered and evaporated. The crude product was purified by flash-chromatography over silica gel with a heptane/AcOEt gradient starting with pure heptane: rac-[2-(4-bromo-2-fluoro-phenyl)-1-(3,4-dichloro-phenyl)-2-oxo-ethyl]-carbamic acid tert-butyl ester was obtained as a colorless viscous oil: MS (ISP): 476.0 and 477.9 (M+H)$^+$.

b) rac-[1-(3,4-Dichloro-phenyl)-2-(3-fluoro-3'-methanesulfonyl-biphenyl-4-yl)-2-oxo-ethyl]-carbamic acid tert-butyl ester To a solution of 0.450 g (0.943 mmol) rac-[2-(4-bromo-2-fluoro-phenyl)-1-(3,4-dichloro-phenyl)-2-oxo-ethyl]-carbamic acid tert-butyl ester in 10.5 ml toluene/ethanol 19:1 were added 69 mg (0.094 mmol) PdCl$_2$ (dppf), 0.238 g (2.83 mmol) sodium bicarbonate, 5 ml water and 212 mg (1.04 mmol) 3-methylsulfonylphenylboronic acid and the mixture heated to reflux for 18 h. The reaction mixture was cooled to ambient temperature, filtered through a Dicalite pad and the filtrated extracted with tertiary butyl methyl ether. The combined extracts were washed with brine, dried over Na$_2$SO$_4$, filtered and evaporated. The crude product was purified by flash-chromatography over silica gel with a heptane/AcOEt gradient with 10-50% AcOEt: rac-[1-(3,4-dichloro-phenyl)-2-(3-fluoro-3'-methanesulfonyl-biphenyl-4-yl)-2-oxo-ethyl]-carbamic acid tert-butyl ester was obtained as colorless solid: MS (ISN): 550.2 and 552.2 (M–H)$^-$.

c) rac-erythro-[1-(3,4-Dichloro-phenyl)-2-(3-fluoro-3'-methanesulfonyl-biphenyl-4-yl)-2-hydroxy-ethyl]-carbamic acid tert-butyl ester To a solution of 178 mg (0.322 mmol) rac-[1-(3,4-dichloro-phenyl)-2-(3-fluoro-3'-methanesulfonyl-biphenyl-4-yl)-2-oxo-ethyl]-carbamic acid tert-butyl ester in 2 ml tetrahydrofuran and 2 ml methanol were added 13.4 mg sodium borohydride and the solution stirred at ambient temperature for 1 h. The reaction was quenched by addition of 10 ml water. The precipitate was filtered, washed with water, pentane and dried: rac-erythro-[1-(3,4-dichloro-phenyl)-2-(3-fluoro-3'-methanesulfonyl-biphenyl-4-yl)-2-hydroxy-ethyl]-carbamic acid tert-butyl ester was obtained as colorless powder: MS (ISP): 554.4 (M+H)$^+$ and 571.5 (M+NH$_4$)$^+$ (100%).

d) rac-erythro-[2-Amino-2-(3,4-dichloro-phenyl)-1-(3-fluoro-3'-methanesulfonyl-biphenyl-4-yl)-ethanol trifluoroacetate To a solution of 97 mg (0.175 mmol) rac-erythro-[1-(3,4-dichloro-phenyl)-2-(3-fluoro-3'-methanesulfonyl-biphenyl-4-yl)-2-hydroxy-ethyl]-carbamic acid tert-butyl ester in 3 ml dichloromethane were added 1.40 g (12.25 mmol) trifluoroacetic acid and the mixture stirred at ambient temperature for 1 h. The reaction mixture was evaporated under reduced pressure and triturated in diethyl ether. The precipitate was filtered and dried. rac-erythro-[2-Amino-2-(3,4-dichloro-phenyl)-1-(3-fluoro-3'-methanesulfonyl-biphenyl-4-yl)-ethanol trifluoroacetate was obtained as colorless powder: MS (ISP): 454.0 and 456.0 (M+H)$^+$.

Example 2 rac-erythro-[2-Amino-2-(3,4-dichloro-phenyl)-1-[4-(5-fluoro-pyridin-3-yl)-2-methyl-phenyl]]-ethanol dihydrochloride

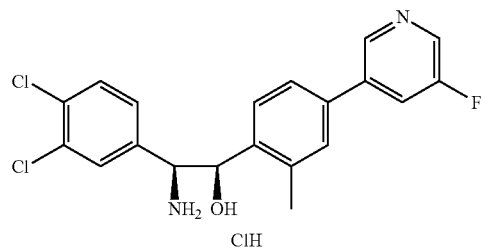 [SMILES: Cc1cc(-c2cncc(F)c2)ccc1[C@@H](O)[C@@H](N)c1ccc(Cl)c(Cl)c1 ; Cl]

a) rac-[2-(4-Bromo-2-methyl-phenyl)-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 5-bromo-2-iodotoluene in analogy to Example 1a): MS (ISP): 473.9 (M+H)$^+$ and 373.9 ((M-Boc)+H)$^+$.

b) rac-[1-(3,4-Dichloro-phenyl)-2-[4-(5-fluoro-pyridin-3-yl)-2-methyl-phenyl]-2-oxo-ethyl]-carbamic acid tert-butyl ester The title compound was prepared from rac-[2-(4-bromo-2-methyl-phenyl)-1-(3,4-dichloro-phenyl)-2-oxo-ethyl]-carbamic acid tert-butyl ester and 5-fluoropyridine-3-boronic acid in analogy to Example 1b): MS (ISP): 489.1 and 491.2 (M+H)$^+$.

c) rac-erythro-[(1-(3,4-Dichloro-phenyl)-2-[4-(5-fluoro-pyridin-3-yl)-2-methyl-phenyl]-2-hydroxy-ethyl)-carbamic acid tert-butyl ester The title compound was prepared from rac-[1-(3,4-dichloro-phenyl)-2-[4-(5-fluoro-pyridin-3-yl)-2-methyl-phenyl]-2-oxo-ethyl]-carbamic acid tert-butyl ester in analogy to Example 1c): MS (ISP): 491.2 and 493.1 (M+H)$^+$.

d) rac-erythro-[2-Amino-2-(3,4-dichloro-phenyl)-1-[4-(5-fluoro-pyridin-3-yl)-2-methyl-phenyl]]-ethanol dihydrochloride The title compound was prepared from rac-erythro-[(1-(3,4-dichloro-phenyl)-2-[4-(5-fluoro-pyridin-3-yl)-2-methyl-phenyl]-2-hydroxy-ethyl)-carbamic acid tert-butyl ester in analogy to Example 1d) but with 4N HCl/dioxane solution in dioxane at ambient temperature for 16 h: MS (ISP): 391.0 and 392.9 (M+H)$^+$.

Example 3 rac-erythro-[2-Amino-2-(3,4-dichloro-phenyl)-1-[4-(5-fluoro-pyridin-3-yl)-3-methoxy-phenyl]-ethanol dihydrochloride

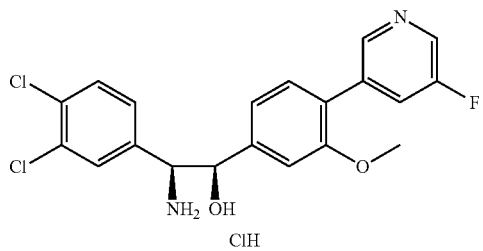 [SMILES: COc1cc([C@@H](O)[C@@H](N)c2ccc(Cl)c(Cl)c2)ccc1-c1cncc(F)c1 ; Cl]

a) rac-[2-(4-Bromo-3-methoxy-phenyl)-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 2-bromo-5-iodoanisole in analogy to Example 1a): MS (ISN): 488.1 (M−H)$^-$.

b) rac-[1-(3,4-Dichloro-phenyl)-2-[4-(5-fluoro-pyridin-3-yl)-3-methoxy-phenyl]-2-oxo-ethyl]-carbamic acid tert-butyl ester The title compound was prepared from rac-[2-(4-bromo-3-methoxy-phenyl)-1-(3,4-dichloro-phenyl)-2-oxo-ethyl]-carbamic acid tert-butyl ester and 5-fluoropyridine-3-boronic acid in analogy to Example 1b): MS (ISN): 503.0 (M−H)$^-$ and 429.01 ((M-tBuOH)−H)$^-$.

c) rac-erythro-[1-(3,4-Dichloro-phenyl)-2-[4-(5-fluoro-pyridin-3-yl)-3-methoxy-phenyl]-2-hydroxy-ethyl]-carbamic acid tert-butyl ester The title compound was prepared from rac-[1-(3,4-dichloro-phenyl)-2-[4-(5-fluoro-pyridin-3-yl)-3-methoxy-phenyl]-2-oxo-ethyl]-carbamic acid tert-butyl ester in analogy to Example 1c): MS (ISP): 507.2 and 509.2 (M+H)$^+$.

d) rac-erythro-[2-Amino-2-(3,4-dichloro-phenyl)-1-[4-(5-fluoro-pyridin-3-yl)-3-methoxy-phenyl]-ethanol]-ethanol dihydrochloride The title compound was prepared from rac-erythro-[(1-(3,4-dichloro-phenyl)-2-[4-(5-fluoro-pyridin-3-yl)-2-methyl-phenyl]-2-hydroxy-ethyl)-carbamic acid tert-butyl ester in analogy to Example 2d): MS (ISP): 407.1 and 409.1 (M+H)$^+$.

Example 4 rac-erythro-[2-Amino-2-(3,4-dichloro-phenyl)-1-[4-(5-fluoro-pyridin-3-yl)-2-methoxy-phenyl]-ethanol dihydrochloride

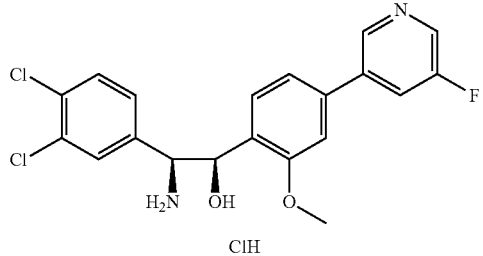 [SMILES: COc1cc(-c2cncc(F)c2)ccc1[C@@H](O)[C@@H](N)c1ccc(Cl)c(Cl)c1 ; Cl]

a) rac-[2-(4-Bromo-2-methoxy-phenyl)-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 4-bromo-1-iodo-2-methoxy-benzene in analogy to Example 1a): MS (ISP): 490.0 (M+H)$^+$ and 390.0 ((M-Boc)+H)$^+$ (100%).

b) rac-[1-(3,4-Dichloro-phenyl)-2-[4-(5-fluoro-pyridin-3-yl)-2-methoxy-phenyl]-2-oxo-ethyl]-carbamic acid tert-butyl ester The title compound was prepared rac-[2-(4-bromo-2-methoxy-phenyl)-1-(3,4-dichloro-phenyl)-2-oxo-ethyl]-carbamic acid tert-butyl ester and 5-fluoropyridine-3-boronic acid in analogy to Example 1b): MS (ISP): 507.4 (M+H)$^+$ (100%) and 522.7 (M+NH$_4$)$^+$.

c) rac-erythro-[2-(3,4-Dichloro-phenyl)-2-[4-(5-fluoro-pyridin-3-yl)-2-methoxy-phenyl]-2-hydroxy-ethyl]-carbamic acid tert-butyl ester The title compound was prepared from rac-[1-(3,4-dichloro-phenyl)-2-[4-(5-fluoro-pyridin-3-yl)-2-methoxy-phenyl]-2-oxo-ethyl]-carbamic acid tert-butyl ester in analogy to Example 1c): MS (ISP): 507.2 and 509.2 (M+H)$^+$.

d) rac-erythro-[2-Amino-2-(3,4-dichloro-phenyl)-1-[4-(5-fluoro-pyridin-3-yl)-2-methoxy-phenyl]-ethanol]-ethanol dihydrochloride The title compound was prepared from rac-erythro-[1-(3,4-Dichloro-phenyl)-2-[4-(5-fluoro-pyridin-3-yl)-2-methoxy-phenyl]-2-hydroxy-ethyl]-carbamic acid tert-butyl ester in analogy to Example 2d): MS (ISP): 407.1 and 409.0 (M+H)$^+$.

Example 5 rac-erythro-[2-Amino-2-(3,4-dichloro-phenyl)-1-(3'-methanesulfonyl-biphenyl-3-yl)-ethanol trifluoroacetate

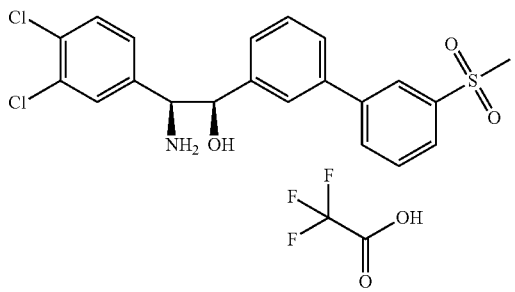

a) rac-[2-(3-Bromo-phenyl)-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1-bromo-3-iodobenzene in analogy to Example 1a): MS (ISP): 460.1 (M+H)$^+$ and 359.9 ((M-Boc)+H)$^+$ (100%).

b) rac-[1-(3,4-Dichloro-phenyl)-2-(3'-methanesulfonyl-biphenyl-3-yl)-2-oxo-ethyl]-carbamic acid tert-butyl ester The title compound was prepared from rac-[2-(3-Bromo-phenyl)-1-(3,4-dichloro-phenyl)-2-oxo-ethyl]-carbamic acid tert-butyl ester and 3-methylsulfonylphenylboronic acid in analogy to Example 1b): MS (ISP): 551.5 ((M+NH$_4$)$^+$, MS (ISN): 532.2 (M−H)$^−$ c) rac-erythro-[1-(3,4-Dichloro-phenyl)-2-hydroxy-2-(3'-methanesulfonyl-biphenyl-3-yl)-ethyl]-carbamic acid tert-butyl ester The title compound was prepared from rac-[1-(3,4-dichloro-phenyl)-2-(3'-methanesulfonyl-biphenyl-3-yl)-2-oxo-ethyl]-carbamic acid tert-butyl ester in analogy to Example 1c): MS (ISP): 553.1 and 555.2 (M+NH$_4$)$^+$.

d) rac-erythro-[2-Amino-2-(3,4-dichloro-phenyl)-1-(3'-methanesulfonyl-biphenyl-3-yl)-ethanol trifluoroacetate The title compound was prepared from rac-erythro-[1-(3,4-Dichloro-phenyl)-2-hydroxy-2-(3'-methanesulfonyl-biphenyl-3-yl)-ethyl]-carbamic acid tert-butyl ester in analogy to Example 1d): MS (ISP): 436.1 and 438.0 (M+H)$^+$.

Example 6

(1R,2S or 1S,2R)-2-Amino-2-(3,4-dichloro-phenyl)-1-(3-fluoro-3'-methanesulfonyl-biphenyl-4-yl)-ethanol hydrochloride

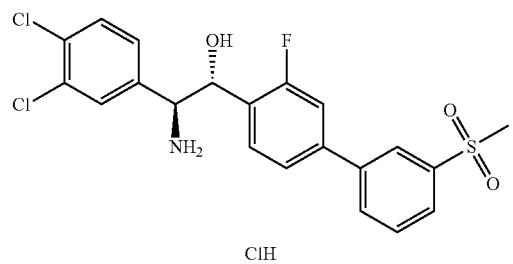 [SMILES: CS(=O)(=O)c1cccc(-c2ccc([C@@H](O)[C@@H](N)c3ccc(Cl)c(Cl)c3)c(F)c2)c1 ; Cl]

a) (−)-[(1S,2R)-1-(3,4-Dichloro-phenyl)-2-(3-fluoro-3'-methanesulfonyl-biphenyl-4-yl)-2-hydroxy-ethyl-carbamic acid tert-butyl ester and (+)-[(1R,2S)-1-(3,4-Dichloro-phenyl)-2-(3-fluoro-3'-methanesulfonyl-biphenyl-4-yl)-2-hydroxy-ethyl]-carbamic acid tert-butyl ester The title compounds were obtained by chromatographic separation of rac-erythro-[1-(3,4-dichloro-phenyl)-2-(3-fluoro-3'-methanesulfonyl-biphenyl-4-yl)-2-hydroxy-ethyl]-carbamic acid tert-butyl ester on a Chiralcel OD column with eluent heptane/isopropanol 85:15 as colorless powders: 1$^{st}$ peak (−)-rotation: MS (ISP): 554.2 (M+H)$^+$ and 571.2 (M+NH$_4$)$^+$ (100%); 2$^{nd}$ peak (+)-rotation: MS (ISP): 554.2 (M+H)$^+$ and 571.2 (M+NH$_4$)$^+$ (100%).

b) (1R,2S or 1S,2R)-2-Amino-2-(3,4-dichloro-phenyl)-1-(3-fluoro-3'-methanesulfonyl-biphenyl-4-yl)-ethanol hydrochloride The title compound was prepared from (−)-[(1S,2R or 1R,2S)-1-(3,4-Dichloro-phenyl)-2-(3-fluoro-3'-methanesulfonyl-biphenyl-4-yl)-2-hydroxy-ethyl]-carbamic acid tert-butyl ester in analogy to Example 2d): MS (ISP): 454.0 and 456.0 (M+H)$^+$.

Example 7 rac-erythro-[2-Amino-2-(3,4-dichloro-phenyl)-1-(3'-methanesulfonyl-biphenyl-4-yl)-ethanol trifluoroacetate

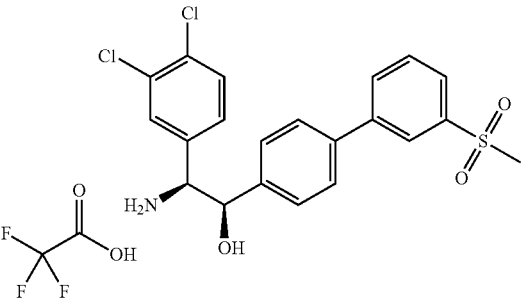 [SMILES: O=C(O)C(F)(F)F ; CS(=O)(=O)c1cccc(-c2ccc([C@@H](O)[C@@H](N)c3ccc(Cl)c(Cl)c3)cc2)c1]

a) rac-[1-(3,4-Dichloro-phenyl)-2-(4-iodo-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1,4-di-iodobenzene in analogy to Example 1a): MS (ISP): 506.1 (M+H)$^+$ and MS (ISN): 503.9 (M−H)$^−$.

b) rac-erythro-[1-(3,4-Dichloro-phenyl)-2-hydroxy-2-(4-iodo-phenyl)-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester in analogy to Example 1c): MS (ISP): 508.1 (M+H)$^+$ and MS (ISN): 505.9 (M−H)$^−$.

c) rac-erythro-[1-(3,4-Dichloro-phenyl)-2-hydroxy-2-(3'-methanesulfonyl-biphenyl-4-yl)-ethyl]-carbamic acid tert-butyl ester The title compound was prepared from rac-erythro-[1-(3,4-Dichloro-phenyl)-2-hydroxy-2-(4-iodo-phenyl)-ethyl]-carbamic acid tert-butyl ester and 3-methylsulfonylphenyl-boronic acid in analogy to Example 1b): MS (ISP): 536.0 (M+H)$^+$.

d) rac-erythro-[2-Amino-2-(3,4-dichloro-phenyl)-1-(3'-methanesulfonyl-biphenyl-4-yl)-ethanol trifluoroacetate The title compound was prepared from rac-erythro-[1-(3,4-dichloro-phenyl)-2-hydroxy-2-(3'-methanesulfonyl-biphenyl-4-yl)-ethyl]-carbamic acid tert-butyl ester in analogy to Example 1d): MS (ISP): 436.1 and 438.2 (M+H)$^+$.

Example 8

(1R,2S or 1S,2R)-2-Amino-2-(3,4-dichloro-phenyl)-1-[4-(5-fluoro-pyridin-3-yl)-phenyl]-ethanol trifluoroacetate

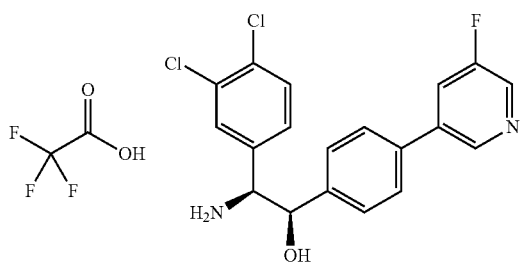 [SMILES: O=C(O)C(F)(F)F ; N[C@@H](c1ccc(Cl)c(Cl)c1)[C@H](O)c1ccc(-c2cncc(F)c2)cc1]

a) [(1S,2R or 1R,2S)-1-(3,4-Dichloro-phenyl)-2-hydroxy-2-(4-iodo-phenyl)-ethyl]-carbamic acid tert-butyl ester The title compound was obtained by chromatographic separation of rac-erythro-[1-(3,4-dichloro-phenyl)-2-hydroxy-2-(4-iodo-phenyl)-ethyl]-carbamic acid tert-butyl ester on a Chiralpak AD column with eluent heptane/isopropanol 85:15 as 1$^{st}$ peak, colorless powder: MS (ISP): 508.0 (M+H)$^+$ and 433.9 ((M−tBuOH)+H)$^+$.

b) [(1S,2R or 1R,2S)-1-(3,4-Dichloro-phenyl)-2-[4-(5-fluoro-pyridin-3-yl)-phenyl]-2-hydroxy-ethyl]-carbamic acid tert-butyl ester The title compound was prepared from [(1S,2R or 1R,2S)-1-(3,4-Dichloro-phenyl)-2-hydroxy-2-(4-iodo-phenyl)-ethyl]-carbamic acid tert-butyl ester and 5-fluoropyridine-3-boronic acid in analogy to Example 1b): MS (ISP): 477.1 and 479.1 (M+H)$^+$.

c) (1R,2S or 1S,2R)-2-Amino-2-(3,4-dichloro-phenyl)-1-[4-(5-fluoro-pyridin-3-yl)-phenyl]-ethanol trifluoroacetate The title compound was prepared from [(1S,2R or 1R,2S)-1-(3,4-dichloro-phenyl)-2-[4-(5-fluoro-pyridin-3-yl)-phenyl]-2-hydroxy-ethyl]-carbamic acid tert-butyl ester in analogy to Example 1d): MS (ISP): 377.2 and 379.1 (M+H)$^+$, 360.0 and 362.1 ((M−NH$_3$)+H)$^+$.

Example 9 rac-erythro-[2-Amino-2-(4-chloro-phenyl)-1-[4-(tetrahydro-pyran-3-yloxy)-phenyl]-ethanol

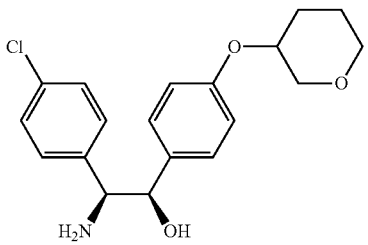

a) rac-[2-[4-(tert-Butyl-dimethyl-silanyloxy)-phenyl]-1-(4-chloro-phenyl)-2-oxo-ethyl]-carbamic acid tert-butyl ester The title compound was prepared from rac-[(4-chloro-phenyl)-(methoxy-methyl-carbamoyl)-methyl]-carbamic acid tert-butyl ester (Intermediate 8) and (4-bromo-phenoxy)-tert-butyl-dimethyl-silane in analogy to Example 1a): MS (ISP): 476.0 (M+H)$^+$.

b) rac-[1-(4-Chloro-phenyl)-2-(4-hydroxy-phenyl)-2-oxo-ethyl]-carbamic acid tert-butyl ester To a solution of 1.37 g (2.88 mmol) rac-[2-[4-(tert-butyl-dimethyl-silanyloxy)-phenyl]-1-(4-chloro-phenyl)-2-oxo-ethyl]-carbamic acid tert-butyl ester in 30 ml methanol were added at ambient temperature 3.45 ml (3.45 mmol) 1M tetrabutylammonium fluoride in tetrahydrofuran. After 10 min the reaction mixture was diluted with diethyl ether, the solution washed twice with sodium bicarbonate solution and once with brine, dried over Na$_2$SO$_4$, filtered and evaporated. The residue was purified by flash-chromatography over silica gel with a heptane/ethyl acetate gradient of 0 to 80% ethyl acetate. The purified title compound was triturated in diisopropyl ether, filtered, dried and obtained as colorless solid: MS (ISN): 360.2 (M−H)$^−$.

c) rac-[1-(4-Chloro-phenyl)-2-oxo-2-[4-(tetrahydro-pyran-3-yloxy)-phenyl]-ethyl]-carbamic acid tert-butyl ester To a solution of 250 mg (0.691 mmol) rac-[1-(4-chloro-phenyl)-2-(4-hydroxy-phenyl)-2-oxo-ethyl]-carbamic acid tert-butyl ester, 257 mg (0.864 mmol) triphenylphosphine and 84.7 mg (0.829 mmol) tetrahydro-pyran-3-ol in 8.5 ml tetrahydrofuran were added 191 mg (0.829 mmol) di-tert-butyl azodicarboxylate and the reaction mixture stirred at ambient temperature for 2 hours. Then the reaction mixture was evaporated and purified by flash chromatography on silica gel with a heptane/ethyl acetate gradient of 0-30% ethyl acetate. The title compound was obtained as colorless solid: MS (ISN): 444.2 (M−H)⁻.

d) rac-[2-Amino-2-(4-chloro-phenyl)-1-[4-(tetrahydro-pyran-3-yloxy)-phenyl]-ethanone hydrochloride The title compound was prepared from rac-[1-(4-chloro-phenyl)-2-oxo-2-[4-(tetrahydro-pyran-3-yloxy)-phenyl]-ethyl]-carbamic acid tert-butyl ester in analogy to Example 38b): MS (ISP): 346.1 and 348.2 (M+H)⁺.

e) rac-erythro-[rac-2-Amino-2-(4-chloro-phenyl)-1-[4-(tetrahydro-pyran-3-yloxy)-phenyl]-ethanol The title compound was prepared from rac-[2-amino-2-(4-chloro-phenyl)-1-[4-(tetrahydro-pyran-3-yloxy)-phenyl]-ethanone hydrochloride in analogy to Example 1c): MS (ISP): 348.2 (M+H)⁺, 330.1 ((M−H₂O)+H)⁺.

Example 10 rac-erythro-[2-Amino-2-(4-chloro-phenyl)-1-(4-isopropoxy-phenyl)-ethanol hydrochloride

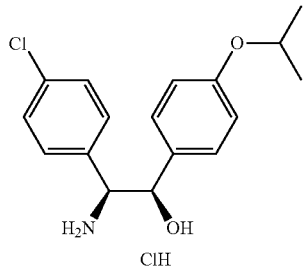 [SMILES: CC(C)Oc1ccc([C@@H](O)[C@@H](N)c2ccc(Cl)cc2)cc1 ; Cl]

a) rac-[1-(4-Chloro-phenyl)-2-(4-isopropoxy-phenyl)-2-oxo-ethyl]-carbamic acid tert-butyl ester The title compound was prepared from rac-[1-(4-chloro-phenyl)-2-(4-hydroxy-phenyl)-2-oxo-ethyl]-carbamic acid tert-butyl ester and isopropanol in analogy to Example 9c): MS (ISP): 404.4 (M+H)⁺.

b) rac-erythro-[1-(4-Chloro-phenyl)-2-hydroxy-2-(4-isopropoxy-phenyl)-ethyl]-carbamic acid tert-butyl ester The title compound was prepared from rac-[1-(4-chloro-phenyl)-2-(4-isopropoxy-phenyl)-2-oxo-ethyl]-carbamic acid tert-butyl ester in analogy to Example 1c): MS (ISN): 404.3 (M−H)⁻ and 464.1 ((M+AcOH)−H)⁻.

c) rac-erythro-[2-Amino-2-(4-chloro-phenyl)-1-(4-isopropoxy-phenyl)-ethanol hydrochloride The title compound was prepared from rac-[1-(4-chlorophenyl)-2-hydroxy-2-(4-isopropoxy-phenyl)-ethyl]-carbamic acid tert-butyl ester in analogy to Example 2d): MS (ISP): 306.1 (M+H)⁺, 288.1 ((M−NH₃)+H)⁺.

Example 11 rac-erythro-[2-Amino-2-(3,4-dichloro-phenyl)-1-[5-(3-methanesulfonyl-phenyl)-pyridin-2-yl]-ethanol bistrifluoroacetate

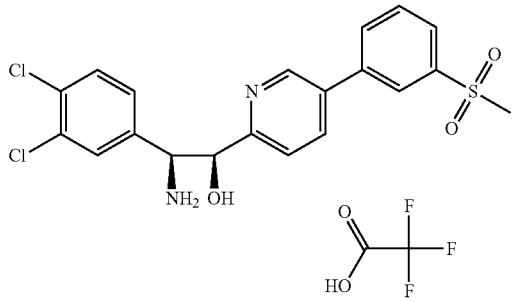 [SMILES: CS(=O)(=O)c1cccc(-c2ccc([C@@H](O)[C@@H](N)c3ccc(Cl)c(Cl)c3)nc2)c1 ; O=C(O)C(F)(F)F]

a) rac-[2-(5-Bromo-pyridin-2-yl)-1-(3,4-dichlorophenyl)-2-oxo-ethyl]-carbamic acid tert-butyl ester To a solution of 0.705 g (2.41 mmol) 5-bromo-2-iodopyridine in 4.8 ml dry tetrahydrofuran were added at 0° C. drop-wise 1.20 ml (2.41 mmol) of a 2M solution of isopropylmagnesium chloride in tetrahydrofuran. The mixture was stirred at 0° C. for 1.5 h and then 0.250 g (0.688 mmol) rac-[(3,4-Dichloro-phenyl)-(methoxy-methyl-carbamoyl)-methyl]-carbamic acid tert-butyl ester (Intermediate 9) were added. The ice bath was removed and stirring continued at ambient temperature for 2 h. The reaction was quenched by addition of 7 ml saturated aqueous ammonium chloride solution. The mixture was diluted with water and extracted with ethyl acetate. The combined extracts were washed with brine, dried over Na₂SO₄, filtered and evaporated. The crude product was purified by flash-chromatography over silica gel with a heptane/ethyl acetate gradient beginning with 5% ethyl acetate. The title compound was obtained al light yellow solid: MS (ISP): 459.1 and 461.1 (M+H)⁺, 403.0 and 405.1 ((M−isobutene)+H)⁺ (100%).

b) rac-[1-(3,4-Dichloro-phenyl)-2-[5-(3-methanesulfonyl-phenyl)-pyridin-2-yl]-2-oxo-ethyl]-carbamic acid tert-butyl ester The title compound was prepared from rac-[2-(5-bromo-pyridin-2-yl)-1-(3,4-dichloro-phenyl)-2-oxo-ethyl]-carbamic acid tert-butyl ester and 3-methylsulfonylphenylboronic acid in analogy to Example 1b): MS (ISP): 535.1 and 536.1 (M+H)⁺, 479.1 and 481.0 ((M−isobutene)+H)⁺ (100%).

c) rac-erythro-[1-(3,4-Dichloro-phenyl)-2-hydroxy-
2-[5-(3-methanesulfonyl-phenyl)-pyridin-2-yl]-
ethyl]-carbamic acid tert-butyl ester The title compound was prepared from rac-[1-(3,4-dichloro-phenyl)-2-[5-(3-methanesulfonyl-phenyl)-pyridin-2-yl]-2-oxo-ethyl]-carbamic acid tert-butyl ester in analogy to Example 1c): MS (ISP): 537.3 and 539.2 (M+H)⁺.

d) rac-erythro-[2-Amino-2-(3,4-dichloro-phenyl)-1-
[5-(3-methanesulfonyl-phenyl)-pyridin-2-yl]-ethanol
bistrifluoroacetate The title compound was prepared from rac-erythro-[1-(3,4-dichloro-phenyl)-2-hydroxy-2-[5-(3-methanesulfonyl-phenyl)-pyridin-2-yl]-ethyl]-carbamic acid tert-butyl ester in analogy to Example 1d): MS (ISP): 437.1 and 439.1 (M+H)⁺.

Example 12 rac-erythro-[2-Amino-2-(3,4-dichloro-phenyl)-1-(5'-fluoro-[3,3']bipyridinyl-6-yl)-ethanol trihydrochloride

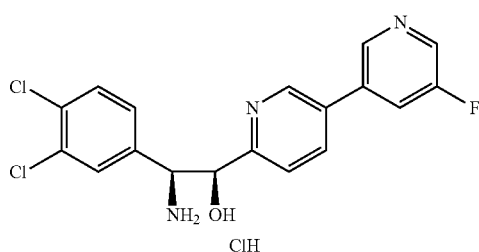 [SMILES: N[C@@H](c1ccc(Cl)c(Cl)c1)[C@H](O)c1ccc(-c2cncc(F)c2)cn1 ; Cl]

a) rac-[1-(3,4-Dichloro-phenyl)-2-(5'-fluoro-[3,3']
bipyridinyl-6-yl)-2-oxo-ethyl]-carbamic acid tert-
butyl ester The title compound was prepared from rac-[2-(5-bromo-pyridin-2-yl)-1-(3,4-dichloro-phenyl)-2-oxo-ethyl]-carbamic acid tert-butyl ester and 5-fluoropyridine-3-boronic acid in analogy to Example 1b): MS (ISP): 476.1 and 478.1 (M+H)⁺.

b) rac-erythro-[1-(3,4-Dichloro-phenyl)-2-(5'-fluoro-
[3,3']bipyridinyl-6-yl)-2-hydroxy-ethyl]-carbamic
acid tert-butyl ester The title compound was prepared from rac-[1-(3,4-dichloro-phenyl)-2-(5'-fluoro-[3,3]bipyridinyl-6-yl)-2-oxo-ethyl]-carbamic acid tert-butyl ester in analogy to Example 1c): MS (ISP): 478.1 and 480.1 (M+H)⁺, 422.0 and 424.1 ((M-isobutene)+H)⁺ (100%).

c) rac-erythro-[2-Amino-2-(3,4-dichloro-phenyl)-1-
(5'-fluoro-[3,3']bipyridinyl-6-yl)-ethanol trihydro-
chloride The title compound was prepared from rac-erythro-[1-(3,4-dichloro-phenyl)-2-(5'-fluoro-[3,3]bipyridinyl-6-yl)-2-hydroxy-ethyl]-carbamic acid tert-butyl ester in analogy to Example 2d): MS (ISP): 378.0 and 380.0 (M+H)⁺.

Example 13 rac-erythro-[2-Amino-2-(3,4-dichloro-phenyl)-1-[3-
fluoro-5-(3-methoxy-phenyl)-pyridin-2-yl]-ethanol
dihydrochloride

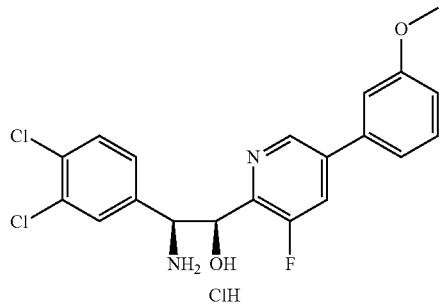 [SMILES: COc1cccc(-c2cnc([C@@H](O)[C@@H](N)c3ccc(Cl)c(Cl)c3)c(F)c2)c1 ; Cl]

a) rac-[1-(3,4-Dichloro-phenyl)-2-[4-(5-fluoro-pyri-
din-3-yl)-2-methoxy-phenyl]-2-oxo-ethyl]-carbamic
acid tert-butyl ester The title compound was prepared from rac-[2-(4-bromo-2-methoxy-phenyl)-1-(3,4-dichloro-phenyl)-2-oxo-ethyl]-carbamic acid tert-butyl ester and 5-fluoropyridine-3-boronic acid in analogy to Example 1b): MS (ISP): 505.4 and 507.4 (M+H)⁺.

b) rac-erythro-[1-(3,4-Dichloro-phenyl)-2-[3-fluoro-
5-(3-methoxy-phenyl)-pyridin-2-yl]-2-hydroxy-
ethyl]-carbamic acid tert-butyl ester The title compound was prepared from rac-[1-(3,4-dichloro-phenyl)-2-[4-(5-fluoro-pyridin-3-yl)-2-methoxy-phenyl]-2-oxo-ethyl]-carbamic acid tert-butyl ester in analogy to Example 1c): MS (ISP): 507.1 and 509.3 (M+H)⁺, 451.0 and 453.0 ((M-isobutene)+H)⁺ (100%).

c) rac-erythro-[2-Amino-2-(3,4-dichloro-phenyl)-1-
[3-fluoro-5-(3-methoxy-phenyl)-pyridin-2-yl]-etha-
nol dihydrochloride The title compound was prepared from rac-erythro-[1-(3,4-dichloro-phenyl)-2-[3-fluoro-5-(3-methoxy-phenyl)-pyridin-2-yl]-2-hydroxy-ethyl]-carbamic acid tert-butyl ester in analogy to Example 2d): MS (ISP): 407.1 and 409.0 (M+H)⁺.

Example 14 rac-erythro-[2-Amino-2-(3,4-dichloro-phenyl)-1-[4-
(5-fluoro-pyridin-3-yl)-3-methyl-phenyl]-ethanol
bis-trifluoroacetate

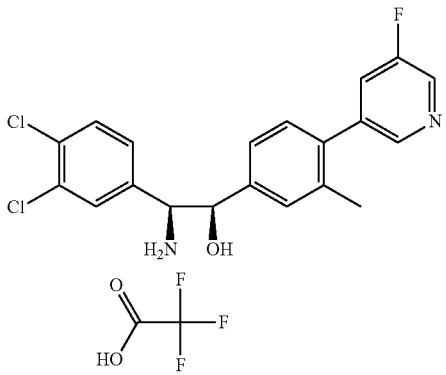

a) rac-[1-(3,4-Dichloro-phenyl)-2-[4-(5-fluoro-pyridin-3-yl)-3-methyl-phenyl]-2-oxo-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and 3-(4-bromo-2-methyl-phenyl)-5-fluoro-pyridine (Intermediate 12) in analogy to Example 1a): MS (ISP): 489.2 and 491.1 (M+H)$^+$.

b) rac-erythro-[1-(3,4-Dichloro-phenyl)-2-[4-(5-fluoro-pyridin-3-yl)-3-methyl-phenyl]-2-hydroxy-ethyl]-carbamic acid tert-butyl ester The title compound was prepared from rac-[1-(3,4-dichloro-phenyl)-2-[4-(5-fluoro-pyridin-3-yl)-3-methyl-phenyl]-2-oxo-ethyl]-carbamic acid tert-butyl ester in analogy to Example 1c): MS (ISP): 491.2 and 493.2 (M+H)$^+$.

c) rac-erythro-[2-Amino-2-(3,4-dichloro-phenyl)-1-[4-(5-fluoro-pyridin-3-yl)-3-methyl-phenyl]-ethanol bis-trifluoroacetate The title compound was prepared from rac-erythro-[1-(3,4-dichloro-phenyl)-2-[4-(5-fluoro-pyridin-3-yl)-3-methyl-phenyl]-2-hydroxy-ethyl]-carbamic acid tert-butyl ester in analogy to Example 1d): MS (ISP): 391.0 and 392.9 (M+H)$^+$.

Example 15 rac-erythro-[rac-2-Amino-2-(3,4-dichloro-phenyl)-1-[2-methyl-6-(tetrahydro-furan-3-yloxy)-pyridin-3-yl]-ethanol dihydrochloride

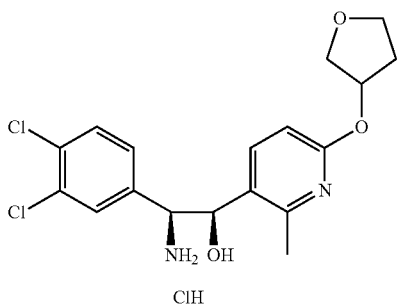 [SMILES: Cc1nc(OC2CCOC2)ccc1[C@@H](O)[C@@H](N)c1ccc(Cl)c(Cl)c1 ; Cl]

a) rac-[1-(3,4-Dichloro-phenyl)-2-[2-methyl-6-(tetrahydro-furan-3-yloxy)-pyridin-3-yl]-2-oxo-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and rac-3-bromo-2-methyl-6-(tetrahydro-furan-3-yloxy)-pyridine (Intermediate 13) in analogy to Example 1a): MS (ISP): 481.2 (M+H)$^+$ and 483.2 ((M-Boc)+H)$^+$ (100%).

b) rac-erythro-[rac-1-(3,4-Dichloro-phenyl)-2-hydroxy-2-[2-methyl-6-(tetrahydro-furan-3-yloxy)-pyridin-3-yl]-ethyl]-carbamic acid tert-butyl ester The title compound was prepared from rac-[1-(3,4-dichloro-phenyl)-2-[2-methyl-6-(tetrahydro-furan-3-yloxy)-pyridin-3-yl]-2-oxo-ethyl]-carbamic acid tert-butyl ester in analogy to Example 1c): MS (ISP): 483.3 and 485.2 (M+H)$^+$.

c) rac-erythro-[rac-2-Amino-2-(3,4-dichloro-phenyl)-1-[2-methyl-6-(tetrahydro-furan-3-yloxy)-pyridin-3-yl]-ethanol dihydrochloride The title compound was prepared from rac-erythro-[1-(3,4-dichloro-phenyl)-2-hydroxy-2-[2-methyl-6-(tetrahydro-furan-3-yloxy)-pyridin-3-yl]-ethyl]-carbamic acid tert-butyl ester in analogy to Example 2d): MS (ISP): 383.1 and 385.1 (M+H)$^+$.

Example 16 rac-erythro-[rac-2-Amino-2-(3,4-dichloro-phenyl)-1-[2-fluoro-4-(tetrahydro-furan-3-yloxy)-phenyl]-ethanol hydrochloride

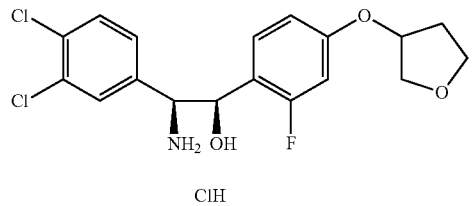 [SMILES: N[C@@H](c1ccc(Cl)c(Cl)c1)[C@H](O)c1ccc(OC2CCOC2)cc1F ; Cl]

a) rac-[1-(3,4-Dichloro-phenyl)-2-[2-methyl-6-(tetrahydro-furan-3-yloxy)-pyridin-3-yl]-2-oxo-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and rac-3-(4-bromo-3-fluoro-phenoxy)-tetrahydro-furan (Intermediate 14) in analogy to Example 1a): MS (ISP): 484.3 and 486.2 (M+H)$^+$, 428.1 and 430.1 ((M-isobutene)+H)$^+$ (100%), 384.1 and 385.9 ((M-Boc)+H)$^+$.

b) rac-erythro-[rac-1-(3,4-Dichloro-phenyl)-2-[2-fluoro-4-(tetrahydro-furan-3-yloxy)-phenyl]-2-hydroxy-ethyl]-carbamic acid tert-butyl ester The title compound was prepared from rac-[1-(3,4-dichloro-phenyl)-2-[2-methyl-6-(tetrahydro-furan-3-yloxy)-pyridin-3-yl]-2-oxo-ethyl]-carbamic acid tert-butyl ester in analogy to Example 1c): MS (ISP): 486.3 and 488.2 (M+H)$^+$.

c) rac-erythro-[rac-2-Amino-2-(3,4-dichloro-phenyl)-1-[2-fluoro-4-(tetrahydro-furan-3-yloxy)-phenyl]-ethanol hydrochloride The title compound was prepared from rac-erythro-[1-(3,4-Dichloro-phenyl)-2-[2-fluoro-4-(tetrahydro-furan-3-yloxy)-phenyl]-2-hydroxy-ethyl]-carbamic acid tert-butyl ester in analogy to Example 2d): MS (ISP): 386.0 and 388.0 (M+H)$^+$.

Example 17 rac-erythro-[2-Amino-2-(3,4-dichloro-phenyl)-1-[2-methyl-6-(tetrahydro-pyran-4-yloxy)-pyridin-3-yl]-ethanol dihydrochloride

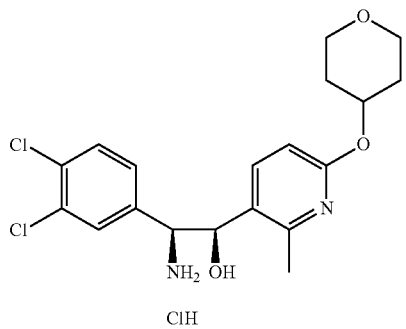 [SMILES: Cc1nc(OC2CCOCC2)ccc1[C@@H](O)[C@@H](N)c1ccc(Cl)c(Cl)c1 ; Cl]

a) rac-[1-(3,4-Dichloro-phenyl)-2-[2-methyl-6-(tetrahydro-pyran-4-yloxy)-pyridin-3-yl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 3-bromo-2-methyl-6-(tetrahydro-pyran-4-yloxy)-pyridine (Intermediate 15) in analogy to Example 1a): MS (ISN): 493.1 and 495.3 (M–H)⁻.

b) rac-erythro-[1-(3,4-Dichloro-phenyl)-2-hydroxy-2-[2-methyl-6-(tetrahydro-pyran-4-yloxy)-pyridin-3-yl]-ethyl]-carbamic acid tert-butyl ester The title compound was prepared from rac-[1-(3,4-dichloro-phenyl)-2-[2-methyl-6-(tetrahydro-pyran-4-yloxy)-pyridin-3-yl]-2-oxo-ethyl]-carbamic acid tert-butyl ester in analogy to Example 1c): MS (ISP): 497.2 and 499.1 (M+H)⁺.

c) rac-erythro-[2-Amino-2-(3,4-dichloro-phenyl)-1-[2-methyl-6-(tetrahydro-pyran-4-yloxy)-pyridin-3-yl]-ethanol dihydrochloride The title compound was prepared from rac-erythro-[1-(3,4-dichloro-phenyl)-2-hydroxy-2-[2-methyl-6-(tetrahydro-pyran-4-yloxy)-pyridin-3-yl]-ethyl]-carbamic acid tert-butyl ester in analogy to Example 2d): MS (ISP): 397.1 and 399.1 (M+H)⁺.

Example 18 rac-erythro-[2-Amino-2-(3,4-dichloro-phenyl)-1-[3-fluoro-4-(tetrahydro-pyran-4-yloxy)-phenyl]-ethanol hydrochloride

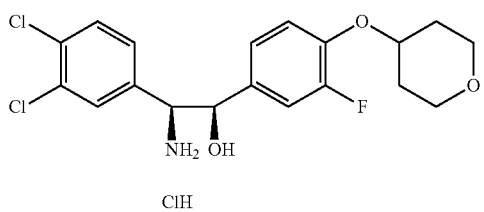 [SMILES: N[C@@H](c1ccc(Cl)c(Cl)c1)[C@H](O)c1ccc(OC2CCOCC2)c(F)c1 ; Cl]

a) rac-[1-(3,4-Dichloro-phenyl)-2-[3-fluoro-4-(tetrahydro-pyran-4-yloxy)-phenyl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 4-(4-bromo-2-fluoro-phenoxy)-tetrahydro-pyran (Intermediate 16) in analogy to Example 1a): MS (ISN): 496.1 and 498.2 (M–H)⁻.

b) rac-erythro-[1-(3,4-Dichloro-phenyl)-2-[3-fluoro-4-(tetrahydro-pyran-4-yloxy)-phenyl]-2-hydroxy-ethyl]-carbamic acid tert-butyl ester The title compound was prepared from rac-[1-(3,4-dichloro-phenyl)-2-[3-fluoro-4-(tetrahydro-pyran-4-yloxy)-phenyl]-2-oxo-ethyl]-carbamic acid tert-butyl ester in analogy to Example 1c): MS (ISP): 500.2 and 502.1 (M+H)⁺, 426.1 and 428.1 ((M–H₂O-isobutene)+H)⁺ (100%).

c) rac-erythro-[2-Amino-2-(3,4-dichloro-phenyl)-1-[3-fluoro-4-(tetrahydro-pyran-4-yloxy)-phenyl]-ethanol hydrochloride The title compound was prepared from rac-erythro-[1-(3,4-dichloro-phenyl)-2-[3-fluoro-4-(tetrahydro-pyran-4-yloxy)-phenyl]-2-hydroxy-ethyl]-carbamic acid tert-butyl ester in analogy to Example 2d): MS (ISP): 400.2 and 402.1 (M+H)⁺.

Example 19 rac-erythro-[rac-2-Amino-2-(3,4-dichloro-phenyl)-1-[6-(tetrahydro-furan-3-yloxy)-pyridin-3-yl]-ethanol dihydrochloride

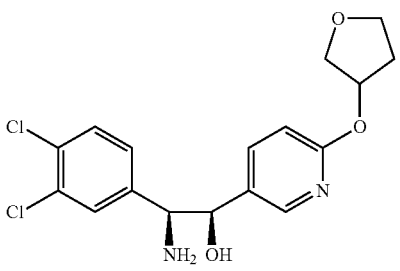

a) rac-[1-(3,4-Dichloro-phenyl)-2-oxo-2-[6-(tetrahydro-furan-3-yloxy)-pyridin-3-yl-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-5-bromo-2-(tetrahydro-furan-3-yloxy)-pyridine (Intermediate 17) in analogy to Example 1a): MS (ISN): 465.0 and 467.0 (M–H)⁻.

b) rac-erythro-[rac-1-(3,4-Dichloro-phenyl)-2-hydroxy-2-[6-(tetrahydro-furan-3-yloxy)-pyridin-3-yl]-ethyl]-carbamic acid tert-butyl ester The title compound was prepared from rac-[1-(3,4-dichloro-phenyl)-2-oxo-2-[6-(tetrahydro-furan-3-yloxy)-pyridin-3-yl]-ethyl]-carbamic acid tert-butyl ester in analogy to Example 1c): MS (ISP): 469.1 and 471.1 (M+H)⁺.

c) rac-erythro-[rac-2-Amino-2-(3,4-dichloro-phenyl)-1-[6-(tetrahydro-furan-3-yloxy)-pyridin-3-yl]-ethanol dihydrochloride The title compound was prepared from rac-erythro-[1-(3,4-dichloro-phenyl)-2-hydroxy-2-[6-(tetrahydro-furan-3-yloxy)-pyridin-3-yl]-ethyl]-carbamic acid tert-butyl ester in analogy to Example 2d): MS (ISP): 369.1 and 370.9 (M+H)⁺.

Example 20 rac-erythro-[2-Amino-2-(3,4-dichloro-phenyl)-1-[3,5-difluoro-4-(tetrahydro-pyran-4-yloxy)-phenyl]-ethanol hydrochloride

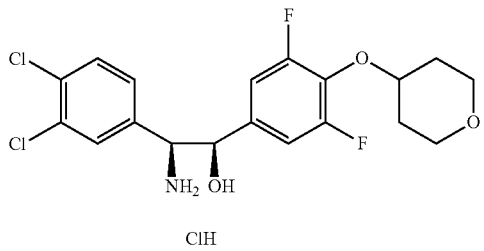 [SMILES: N[C@@H](c1ccc(Cl)c(Cl)c1)[C@H](O)c1cc(F)c(OC2CCOCC2)c(F)c1 ; Cl]

a) rac-[1-(3,4-Dichloro-phenyl)-2-[3,5-difluoro-4-(tetrahydro-pyran-4-yloxy)-phenyl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 4-(4-bromo-2,6-difluoro-phenoxy)-tetrahydro-pyran (Intermediate 18) in analogy to Example 1a): MS (ISP): 516.1 and 518.1 (M+H)⁺, 416.2 and 418.0 ((M-Boc)+H)⁺ (100%).

b) rac-erythro-[1-(3,4-Dichloro-phenyl)-2-[3,5-difluoro-4-(tetrahydro-pyran-4-yloxy)-phenyl]-2-hydroxy-ethyl]-carbamic acid tert-butyl ester The title compound was prepared from rac-[1-(3,4-dichloro-phenyl)-2-[3,5-difluoro-4-(tetrahydro-pyran-4-yloxy)-phenyl]-2-oxo-ethyl]-carbamic acid tert-butyl ester in analogy to Example 1c): MS (ISP): 518.2 and 520.1 (M+H)⁺, 535.4 and 537.3 (M+NH₄)⁺ (100%).

c) rac-erythro-[2-Amino-2-(3,4-dichloro-phenyl)-1-[3,5-difluoro-4-(tetrahydro-pyran-4-yloxy)-phenyl]-ethanol hydrochloride The title compound was prepared from rac-erythro-[1-(3,4-dichloro-phenyl)-2-[3,5-difluoro-4-(tetrahydro-pyran-4-yloxy)-phenyl]-2-hydroxy-ethyl]-carbamic acid tert-butyl ester in analogy to Example 2d): MS (ISP): 418.0 and 420.1 (M+H)⁺.

Example 21 rac-erythro-[2-Amino-2-(3,4-dichloro-phenyl)-1-[4-methyl-6-(tetrahydro-pyran-4-yloxy)-pyridin-3-yl]-ethanol dihydrochloride

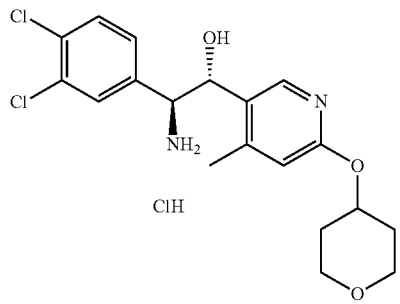 [SMILES: Cc1cc(OC2CCOCC2)ncc1[C@@H](O)[C@@H](N)c1ccc(Cl)c(Cl)c1 ; Cl]

a) rac-[1-(3,4-Dichloro-phenyl)-2-[4-methyl-6-(tetrahydro-pyran-4-yloxy)-pyridin-3-yl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 5-bromo-4-methyl-2-(tetrahydro-pyran-4-yloxy)-pyridine (Intermediate 19) in analogy to Example 1a): MS (ISN): 493.1 and 495.3 (M−H)⁻.

b) rac-erythro-[1-(3,4-Dichloro-phenyl)-2-hydroxy-2-[4-methyl-6-(tetrahydro-pyran-4-yloxy)-pyridin-3-yl]-ethyl]-carbamic acid tert-butyl ester The title compound was prepared from rac-[1-(3,4-dichloro-phenyl)-2-[4-methyl-6-(tetrahydro-pyran-4-yloxy)-pyridin-3-yl]-2-oxo-ethyl]-carbamic acid tert-butyl ester in analogy to Example 1c): MS (ISP): 497.4 and 499.3 (M+H)⁺.

c) rac-erythro-[2-Amino-2-(3,4-dichloro-phenyl)-1-[4-methyl-6-(tetrahydro-pyran-4-yloxy)-pyridin-3-yl]-ethanol dihydrochloride The title compound was prepared from rac-erythro-[1-(3,4-Dichloro-phenyl)-2-hydroxy-2-[4-methyl-6-(tetrahydro-pyran-4-yloxy)-pyridin-3-yl]-ethyl]-carbamic acid tert-butyl ester in analogy to Example 2d): MS (ISP): 397.1 and 399.1 (M+H)⁺.

Example 22 rac-erythro-[2-Amino-2-(3,4-dichloro-phenyl)-1-[6-(tetrahydro-pyran-4-yloxy)-pyridin-3-yl]-ethanol dihydrochloride

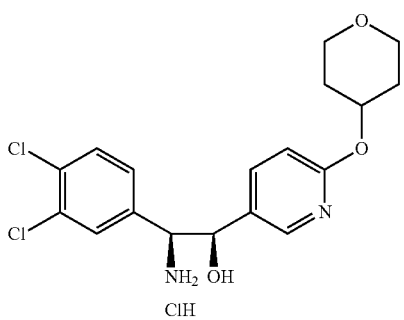 [SMILES: N[C@@H](c1ccc(Cl)c(Cl)c1)[C@H](O)c1ccc(OC2CCOCC2)nc1 ; Cl]

a) rac-[1-(3,4-Dichloro-phenyl)-2-oxo-2-[6-(tetrahydro-pyran-4-yloxy)-pyridin-3-yl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 5-bromo-2-(tetrahydro-pyran-4-yloxy)-pyridine (Intermediate 20) in analogy to Example 1a): MS (ISN): 479.1 and 481.2 (M−H)⁻.

b) rac-erythro-[1-(3,4-Dichloro-phenyl)-2-hydroxy-2-[6-(tetrahydro-pyran-4-yloxy)-pyridin-3-yl]-ethyl]-carbamic acid tert-butyl ester The title compound was prepared from rac-[1-(3,4-dichloro-phenyl)-2-oxo-2-[6-(tetrahydro-pyran-4-yloxy)-pyridin-3-yl]-ethyl]-carbamic acid tert-butyl ester in analogy to Example 1c): MS (ISP): 483.2 and 485.2 (M+H)⁺.

c) rac-erythro-[2-Amino-2-(3,4-dichloro-phenyl)-1-[6-(tetrahydro-pyran-4-yloxy)-pyridin-3-yl]-ethanol dihydrochloride The title compound was prepared from rac-erythro-[1-(3, 4-dichloro-phenyl)-2-hydroxy-2-[6-(tetrahydro-pyran-4-yloxy)-pyridin-3-yl]-ethyl]-carbamic acid tert-butyl ester in analogy to Example 2d): MS (ISP): 383.1 and 385.0 (M+H)⁺.

Example 23 rac-erythro-[rac-2-Amino-2-(3,4-dichloro-phenyl)-1-[5-(tetrahydro-furan-3-yloxy)-pyridin-2-yl]-ethanol dihydrochloride

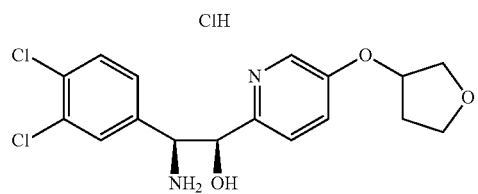 [SMILES: Cl ; N[C@@H](c1ccc(Cl)c(Cl)c1)[C@H](O)c1ccc(OC2CCOC2)cn1]

a) rac-[1-(3,4-Dichloro-phenyl)-2-oxo-2-[5-(tetrahydro-furan-3-yloxy)-pyridin-2-yl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-2-bromo-5-(tetrahydro-furan-3-yloxy)-pyridine (Intermediate 21) in analogy to Example 1a): MS (ISN): 465.0 and 467.0 (M−H)⁻.

b) rac-erythro-[rac-1-(3,4-Dichloro-phenyl)-2-hydroxy-2-[5-(tetrahydro-furan-3-yloxy)-pyridin-2-yl]-ethyl]-carbamic acid tert-butyl ester The title compound was prepared from rac-[1-(3,4-dichloro-phenyl)-2-oxo-2-[5-(tetrahydro-furan-3-yloxy)-pyridin-2-yl]-ethyl]-carbamic acid tert-butyl ester in analogy to Example 1c): MS (ISP): 469.1 and 471.2 (M+H)⁺.

c) rac-erythro-[rac-2-Amino-2-(3,4-dichloro-phenyl)-1-[5-(tetrahydro-furan-3-yloxy)-pyridin-2-yl]-ethanol dihydrochloride The title compound was prepared from rac-erythro-[1-(3, 4-dichloro-phenyl)-2-hydroxy-2-[5-(tetrahydro-furan-3-yloxy)-pyridin-2-yl]-ethyl]-carbamic acid tert-butyl ester in analogy to Example 2d): MS (ISP): 369.1 and 371.0 (M+H)⁺.

Example 24 rac-erythro-[(rac)-2-Amino-2-(3,4-dichloro-phenyl)-1-[4-methyl-6-(tetrahydro-furan-3-yloxy)-pyridin-3-yl]-ethanol dihydrochloride

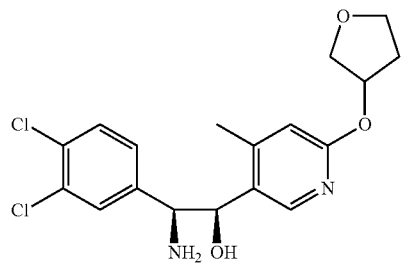

a) rac-[1-(3,4-Dichloro-phenyl)-2-[4-methyl-6-(tetrahydro-furan-3-yloxy)-pyridin-3-yl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-5-bromo-4-methyl-2-(tetrahydro-furan-3-yloxy)-pyridine (Intermediate 22) in analogy to Example 1a): MS (ISN): 479.0 and 481.0 (M−H)⁻.

b) rac-erythro-[rac-1-(3,4-Dichloro-phenyl)-2-hydroxy-2-[4-methyl-6-(tetrahydro-furan-3-yloxy)-pyridin-3-yl]-ethyl]-carbamic acid tert-butyl ester The title compound was prepared from rac-[1-(3,4-dichloro-phenyl)-2-[4-methyl-6-(tetrahydro-furan-3-yloxy)-pyridin-3-yl]-2-oxo-ethyl]-carbamic acid tert-butyl ester in analogy to Example 1c): MS (ISP): 483.3 and 485.2 (M+H)⁺.

c) rac-erythro-[(rac)-2-Amino-2-(3,4-dichloro-phenyl)-1-[4-methyl-6-(tetrahydro-furan-3-yloxy)-pyridin-3-yl]-ethanol dihydrochloride The title compound was prepared from rac-erythro-[rac-1-(3,4-dichloro-phenyl)-2-hydroxy-2-[4-methyl-6-(tetrahydro-furan-3-yloxy)-pyridin-3-yl]-ethyl]-carbamic acid tert-butyl ester in analogy to Example 2d): MS (ISP): 383.1 and 385.1 (M+H)⁺.

Example 25 rac-erythro-[2-Amino-2-(3,4-dichloro-phenyl)-1-[5-(tetrahydro-pyran-4-yloxy)-pyridin-2-yl]-ethanol dihydrochloride

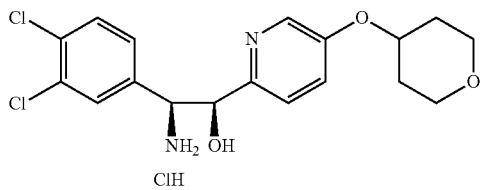 [SMILES: N[C@@H](c1ccc(Cl)c(Cl)c1)[C@H](O)c1ccc(OC2CCOCC2)cn1 ; Cl]

a) rac-[1-(3,4-Dichloro-phenyl)-2-oxo-2-[5-(tetrahydro-pyran-4-yloxy)-pyridin-2-yl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 2-bromo-5-(tetrahydro-pyran-4-yloxy)-pyridine (Intermediate 23) in analogy to Example 1a): MS (ISP): 481.2 and 483.1 (M+H)$^+$.

b) rac-erythro-[1-(3,4-Dichloro-phenyl)-2-hydroxy-2-[5-(tetrahydro-pyran-4-yloxy)-pyridin-2-yl]-ethyl]-carbamic acid tert-butyl ester The title compound was prepared from rac-[1-(3,4-dichloro-phenyl)-2-oxo-2-[5-(tetrahydro-pyran-4-yloxy)-pyridin-2-yl]-ethyl]-carbamic acid tert-butyl ester in analogy to Example 1c): MS (ISP): 483.2 and 485.2 (M+H)$^+$.

c) rac-erythro-[2-Amino-2-(3,4-dichloro-phenyl)-1-[5-(tetrahydro-pyran-4-yloxy)-pyridin-2-yl]-ethanol dihydrochloride The title compound was prepared from rac-erythro-[1-(3,4-dichloro-phenyl)-2-hydroxy-2-[5-(tetrahydro-pyran-4-yloxy)-pyridin-2-yl]-ethyl]-carbamic acid tert-butyl ester in analogy to Example 2d): MS (ISP): 383.1 and 385.1 (M+H)$^+$.

Example 26 rac-erythro-[2-Amino-2-(3,4-dichloro-phenyl)-1-[5-methyl-6-(tetrahydro-pyran-4-yloxy)-pyridin-3-yl]-ethanol dihydrochloride

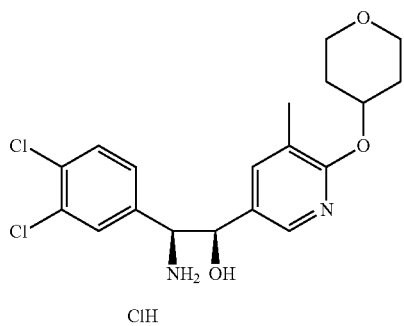 [SMILES: Cc1cc([C@@H](O)[C@@H](N)c2ccc(Cl)c(Cl)c2)cnc1OC1CCOCC1 ; Cl]

a) rac-[1-(3,4-Dichloro-phenyl)-2-[5-methyl-6-(tetrahydro-pyran-4-yloxy)-pyridin-3-yl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 5-bromo-3-methyl-2-(tetrahydro-pyran-4-yloxy)-pyridine (Intermediate 24) in analogy to Example 1a): MS (ISN): 493.1 and 495.2 (M−H)$^-$.

b) rac-erythro-[1-(3,4-Dichloro-phenyl)-2-hydroxy-2-[5-methyl-6-(tetrahydro-pyran-4-yloxy)-pyridin-3-yl]-ethyl]-carbamic acid tert-butyl ester The title compound was prepared from rac-[1-(3,4-dichloro-phenyl)-2-[5-methyl-6-(tetrahydro-pyran-4-yloxy)-pyridin-3-yl]-2-oxo-ethyl]-carbamic acid tert-butyl ester in analogy to Example 1c): MS (ISP): 497.2 and 499.1 (M+H)$^+$.

c) rac-erythro-[2-Amino-2-(3,4-dichloro-phenyl)-1-[5-methyl-6-(tetrahydro-pyran-4-yloxy)-pyridin-3-yl]-ethanol dihydrochloride The title compound was prepared from rac-erythro-[1-(3,4-dichloro-phenyl)-2-hydroxy-2-[5-methyl-6-(tetrahydro-pyran-4-yloxy)-pyridin-3-yl]-ethyl]-carbamic acid tert-butyl ester in analogy to Example 2d): MS (ISP): 397.1 and 399.1 (M+H)$^+$.

Example 27 rac-erythro-[2-Amino-2-(3,4-dichloro-phenyl)-1-(6-isopropoxy-2-methyl-pyridin-3-yl)-ethanol dihydrochloride

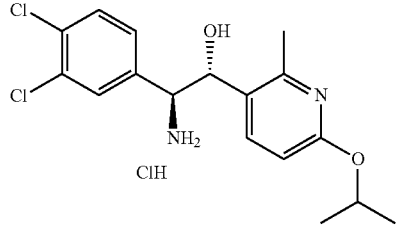 [SMILES: Cc1nc(OC(C)C)ccc1[C@@H](O)[C@@H](N)c1ccc(Cl)c(Cl)c1 ; Cl]

a) rac-[1-(3,4-Dichloro-phenyl)-2-(6-isopropoxy-2-methyl-pyridin-3-yl)-2-oxo-ethyl-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 3-bromo-6-isopropoxy-2-methyl-pyridine (Intermediate 25) in analogy to Example 1a): MS (ISP): 453.2 and 455.2 (M+H)$^+$.

b) rac-erythro-[1-(3,4-Dichloro-phenyl)-2-hydroxy-2-(6-isopropoxy-2-methyl-pyridin-3-yl)-ethyl]-carbamic acid tert-butyl ester The title compound was prepared from rac-[1-(3,4-dichloro-phenyl)-2-(6-isopropoxy-2-methyl-pyridin-3-yl)-2-oxo-ethyl]-carbamic acid tert-butyl ester in analogy to Example 1c): MS (ISP): 455.3 and 457.3 (M+H)$^+$.

c) rac-erythro-[2-Amino-2-(3,4-dichloro-phenyl)-1-(6-isopropoxy-2-methyl-pyridin-3-yl)-ethanol dihydrochloride The title compound was prepared from rac-erythro-[1-(3,4-dichloro-phenyl)-2-hydroxy-2-(6-isopropoxy-2-methyl-pyridin-3-yl)-ethyl]-carbamic acid tert-butyl ester in analogy to Example 2d): MS (ISP): 355.2 and 357.1 (M+H)$^+$.

Example 28 rac-erythro-[2-Amino-2-(3,4-dichloro-phenyl)-1-[2-fluoro-4-(tetrahydro-furan-2-ylmethoxy)-phenyl]-ethanol, hydrochloride salt

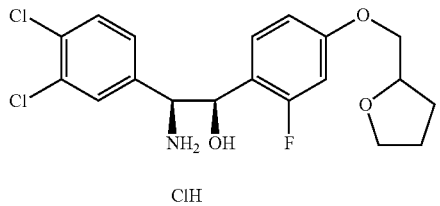 [SMILES: N[C@@H](c1ccc(Cl)c(Cl)c1)[C@H](O)c1ccc(OCC2CCCO2)cc1F ; Cl]

a) rac-[1-(3,4-Dichloro-phenyl)-2-[2-fluoro-4-(tetrahydro-furan-2-yl-methoxy)-phenyl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-2-(4-bromo-3-fluoro-phenoxymethyl)-tetrahydro-furan (Intermediate 26) in analogy to Example 1a): colorless gum.

b) rac-erythro-[1-(3,4-Dichloro-phenyl)-2-[2-fluoro-4-(tetrahydro-furan-2-yl-methoxy)-phenyl]-2-hydroxy-ethyl]-carbamic acid tert-butyl ester The title compound was prepared from rac-[1-(3,4-dichloro-phenyl)-2-[2-fluoro-4-(tetrahydro-furan-2-yl-methoxy)-phenyl]-2-oxo-ethyl]-carbamic acid tert-butyl ester in analogy to Example 1c): colorless gum.

c) rac-erythro-[2-Amino-2-(3,4-dichloro-phenyl)-1-[2-fluoro-4-(tetrahydro-furan-2-yl-methoxy)-phenyl]-ethanol, hydrochloride salt The title compound was prepared from rac-erythro-[1-(3,4-dichloro-phenyl)-2-[2-fluoro-4-(tetrahydro-furan-2-yl-methoxy)-phenyl]-2-hydroxy-ethyl]-carbamic acid tert-butyl ester in analogy to Example 2d): MS (ISP): 400.2 and 402.1 (M+H)$^+$.

Example 29 rac-erythro-[1-[4-[(rac)-2-Amino-2-(3,4-dichloro-phenyl)-1-hydroxy-ethyl]-3-fluoro-phenoxy]-4-chloro-butan-2-ol hydrochloride

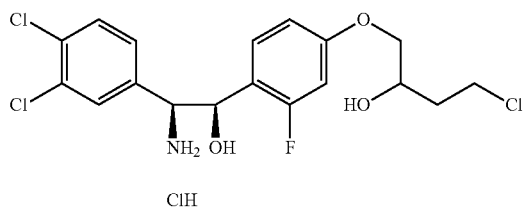 [SMILES: N[C@@H](c1ccc(Cl)c(Cl)c1)[C@H](O)c1ccc(OCC(O)CCCl)cc1F ; Cl]

a) rac-[1-(3,4-Dichloro-phenyl)-2-[2-fluoro-4-(oxetan-2-yl-methoxy)-phenyl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-2-(4-bromo-3-fluoro-phenoxymethyl)-oxetane (Intermediate 27) in analogy to Example 1a): colorless gum.

b) rac-erythro-[1-(3,4-Dichloro-phenyl)-2-[2-fluoro-4-(oxetan-2-yl-methoxy)-phenyl]-2-hydroxy-ethyl]-carbamic acid tert-butyl ester The title compound was prepared from rac-[1-(3,4-dichloro-phenyl)-2-[2-fluoro-4-(oxetan-2-yl-methoxy)-phenyl]-2-oxo-ethyl]-carbamic acid tert-butyl ester in analogy to Example 1c): colorless gum.

c) rac-erythro-[1-[4-[(rac)-2-Amino-2-(3,4-dichloro-phenyl)-1-hydroxy-ethyl]-3-fluoro-phenoxy]-4-chloro-butan-2-ol hydrochloride The title compound was prepared from rac-erythro-[1-(3,4-dichloro-phenyl)-2-[2-fluoro-4-(oxetan-2-yl-methoxy)-phenyl]-2-hydroxy-ethyl]-carbamic acid tert-butyl ester in analogy to Example 2d): MS (ISP): 424.0 and 426.1 (M+H)$^+$.

Example 30 rac-erythro-[2-Amino-2-(3,4-dichloro-phenyl)-1-(6-isopropoxy-4-methyl-pyridin-3-yl)-ethanol dihydrochloride

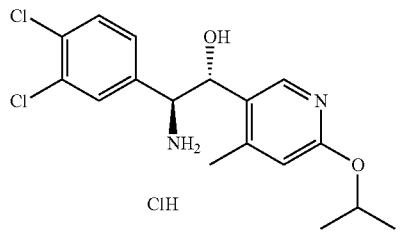 [SMILES: Cc1cc(OC(C)C)ncc1[C@@H](O)[C@@H](N)c1ccc(Cl)c(Cl)c1 ; Cl]

a) rac-[1-(3,4-Dichloro-phenyl)-2-(6-isopropoxy-4-methyl-pyridin-3-yl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 5-bromo-2-isopropoxy-4-methyl-pyridine (Intermediate 28) in analogy to Example 1a): MS (ISP): 453.1 and 455.2 (M+H)$^+$.

b) rac-erythro-[1-(3,4-Dichloro-phenyl)-2-hydroxy-2-(6-isopropoxy-4-methyl-pyridin-3-yl)-ethyl]-carbamic acid tert-butyl ester The title compound was prepared from rac-[1-(3,4-dichloro-phenyl)-2-(6-isopropoxy-4-methyl-pyridin-3-yl)-2-oxo-ethyl]-carbamic acid tert-butyl ester in analogy to Example 1c): MS (ISP): 455.3 and 457.3 (M+H)$^+$.

c) rac-erythro-[2-Amino-2-(3,4-dichloro-phenyl)-1-(6-isopropoxy-4-methyl-pyridin-3-yl)-ethanol dihydrochloride The title compound was prepared from rac-erythro-[1-(3,4-dichloro-phenyl)-2-hydroxy-2-(6-isopropoxy-4-methyl-pyridin-3-yl)-ethyl]-carbamic acid tert-butyl ester in analogy to Example 2d): MS (ISP): 355.1 and 357.1 (M+H)$^+$.

Example 31 rac-erythro-[(rac)-2-Amino-2-(3,4-dichloro-phenyl)-1-[5-methyl-6-(tetrahydro-furan-3-yloxy)-pyridin-3-yl]-ethanol dihydrochloride

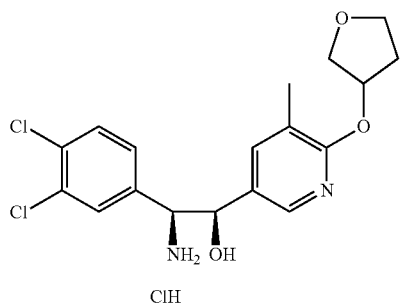 [SMILES: Cc1cc([C@@H](O)[C@@H](N)c2ccc(Cl)c(Cl)c2)cnc1OC1CCOC1 ; Cl]

a) rac-[1-(3,4-Dichloro-phenyl)-2-[5-methyl-6-(tetrahydro-furan-3-yloxy)-pyridin-3-yl]-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and rac-5-bromo-3-methyl-2-(tetrahydro-furan-3-yloxy)-pyridine (Intermediate 29) in analogy to Example 1a): MS (ISP): 481.3 and 483.2 (M+H)$^+$.

b) rac-erythro-[1-(3,4-Dichloro-phenyl)-2-hydroxy-2-[5-methyl-6-(tetrahydro-furan-3-yloxy)-pyridin-3-yl]-ethyl]-carbamic acid tert-butyl ester The title compound was prepared from rac-[1-(3,4-dichloro-phenyl)-2-[5-methyl-6-(tetrahydro-furan-3-yloxy)-pyridin-3-yl]-2-oxo-ethyl]-carbamic acid tert-butyl ester in analogy to Example 1c): MS (ISP): 483.3 and 485.2 (M+H)$^+$.

c) rac-erythro-[(rac)-2-Amino-2-(3,4-dichloro-phenyl)-1-[5-methyl-6-(tetrahydro-furan-3-yloxy)-pyridin-3-yl]-ethanol dihydrochloride The title compound was prepared from rac-erythro-[(rac)-2-amino-2-(3,4-dichloro-phenyl)-1-[5-methyl-6-(tetrahydro-furan-3-yloxy)-pyridin-3-yl]-ethanol dihydrochloride in analogy to Example 2d): MS (ISP): 383.1 and 385.1 (M+H)$^+$.

Example 32 rac-erythro-[2-Amino-2-(3,4-dichloro-phenyl)-1-(5-isopropoxy-pyridin-2-yl)-ethanol dihydrochloride

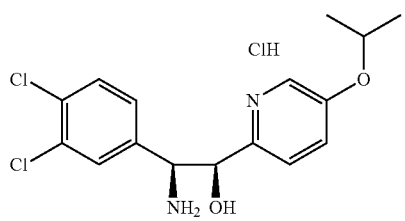 [SMILES: CC(C)Oc1ccc([C@@H](O)[C@@H](N)c2ccc(Cl)c(Cl)c2)nc1 ; Cl]

a) rac-[1-(3,4-Dichloro-phenyl)-2-(5-isopropoxy-pyridin-2-yl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 2-bromo-5-isopropoxy-pyridine (Intermediate 30) in analogy to Example 1a): MS (ISP): 439.2 and 441.1 (M+H)$^+$, 383.2 and 385.1 ((M-isobutene)+H)$^+$ (100%).

b) rac-erythro-[1-(3,4-Dichloro-phenyl)-2-hydroxy-2-(5-isopropoxy-pyridin-2-yl)-ethyl]-carbamic acid tert-butyl ester The title compound was prepared from rac-[1-(3,4-dichloro-phenyl)-2-(5-isopropoxy-pyridin-2-yl)-2-oxo-ethyl]-carbamic acid tert-butyl ester in analogy to Example 1c): MS (ISP): 441.2 and 443.1 (M+H)$^+$.

c) rac-erythro-[2-Amino-2-(3,4-dichloro-phenyl)-1-(5-isopropoxy-pyridin-2-yl)-ethanol dihydrochloride The title compound was prepared from rac-erythro-[1-(3,4-dichloro-phenyl)-2-hydroxy-2-(5-isopropoxy-pyridin-2-yl)-ethyl]-carbamic acid tert-butyl ester in analogy to Example 2d): MS (ISP): 340.9 and 343.0 (M+H)$^+$.

Example 33 rac-erythro-[2-Amino-2-(3,4-dichloro-phenyl)-1-[2-fluoro-4-(tetrahydro-pyran-4-yloxy)-phenyl]-ethanol hydrochloride

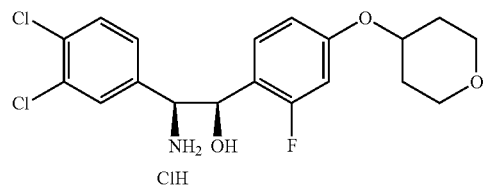 [SMILES: N[C@@H](c1ccc(Cl)c(Cl)c1)[C@H](O)c1ccc(OC2CCOCC2)cc1F ; Cl]

a) rac-[1-(3,4-Dichloro-phenyl)-2-[2-fluoro-4-(tetrahydro-pyran-4-yloxy)-phenyl]-2-oxo-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and 4-(4-bromo-3-fluoro-phenoxy)-tetrahydro-pyran (Intermediate 31) in analogy to Example 1a): MS (ISP): 498.1 and 500.2 (M+H)$^+$, 442.2 and 444.0 ((M-isobutene)+H)$^+$ (100%).

b) rac-erythro-[1-(3,4-Dichloro-phenyl)-2-[2-fluoro-4-(tetrahydro-pyran-4-yloxy)-phenyl]-2-hydroxy-ethyl]-carbamic acid tert-butyl ester The title compound was prepared from rac-[1-(3,4-dichloro-phenyl)-2-[2-fluoro-4-(tetrahydro-pyran-4-yloxy)-phenyl]-2-oxo-ethyl]-carbamic acid tert-butyl ester in analogy to Example 1c): MS (ISP): 500.2 and 502.2 (M+H)$^+$, 482.3 and 484.2 ((M-H$_2$O)+H)$^+$, 426.1 and 428.0 ((M-(H$_2$O+isobutene))+H)$^+$ (100%).

c) rac-erythro-[2-Amino-2-(3,4-dichloro-phenyl)-1-[2-fluoro-4-(tetrahydro-pyran-4-yloxy)-phenyl]-ethanol hydrochloride The title compound was prepared from rac-erythro-[1-(3,4-dichloro-phenyl)-2-[2-fluoro-4-(tetrahydro-pyran-4-yloxy)-phenyl]-2-hydroxy-ethyl]-carbamic acid tert-butyl ester in analogy to Example 2d): MS (ISP): 400.1 and 402.0 (M+H)$^+$.

Example 34 rac-erythro-[2-Amino-2-(3,4-dichloro-phenyl)-1-[2-fluoro-4-(3-methyl-oxetan-3-ylmethoxy)-phenyl]-ethanol

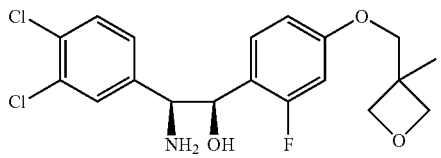 [SMILES: CC1(COc2ccc([C@@H](O)[C@@H](N)c3ccc(Cl)c(Cl)c3)c(F)c2)COC1]

a) rac-[1-(3,4-Dichloro-phenyl)-2-[2-fluoro-4-(3-methyl-oxetan-3-ylmethoxy)-phenyl]-2-oxo-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and 3-(4-bromo-3-fluoro-phenoxymethyl)-3-methyl-oxetane (Intermediate 32) in analogy to Example 1a): MS (ISP): 498.3 and 500.2 (M+H)$^+$, 398.2 and 400.0 ((M-Boc)+H)$^+$ (100%); MS (ISN): 496.4 and 498.5 (M-H)$^-$.

b) rac-erythro-[1-(3,4-Dichloro-phenyl)-2-[2-fluoro-4-(3-methyl-oxetan-3-ylmethoxy)-phenyl]-2-hydroxy-ethyl]-carbamic acid tert-butyl ester The title compound was prepared from rac-[1-(3,4-dichloro-phenyl)-2-[2-fluoro-4-(3-methyl-oxetan-3-ylmethoxy)-phenyl]-2-oxo-ethyl]-carbamic acid tert-butyl ester in analogy to Example 1c): MS (ISP): 500.2 and 502.2 (M+H)$^+$, 426.1 and 428.0 ((M-(H$_2$O+isobutene))+H)$^+$ (100%).

c) rac-erythro-[2-Amino-2-(3,4-dichloro-phenyl)-1-[2-fluoro-4-(3-methyl-oxetan-3-ylmethoxy)-phenyl]-ethanol The title compound was prepared from rac-erythro-[1-(3,4-dichloro-phenyl)-2-[2-fluoro-4-(3-methyl-oxetan-3-yl-methoxy)-phenyl]-2-hydroxy-ethyl]-carbamic acid tert-butyl ester by stirring a solution of the starting material in dichloromethane/trifluoroacetic acid 1:1 at ambient temperature for 5 min. The reaction mixture was evaporated under reduced pressure at ambient temperature, the residue taken up in dichloromethane and treated with saturated aqueous sodium bicarbonate solution. The emulsion was stirred at ambient temperature until no more gas evolution was observed (~15 min) and then evaporated. The residue was taken up in dichloromethane, treated in an ultrasound bath and the resulting suspension filtered. Evaporation of the filtrate provided the title compound as colorless oil: MS (ISP): 400.1 and 402.0 (M+H)$^+$.

Example 35 rac-erythro-[2-Amino-2-(3,4-dichloro-phenyl)-1-(4-trimethylsilanyl-phenyl)-ethanol trifluoroacetate

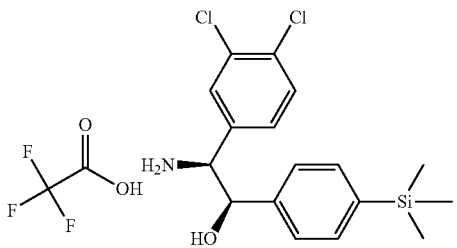

a) rac-[1-(3,4-Dichloro-phenyl)-2-oxo-2-(4-trimethylsilanyl-phenyl)-ethyl]-carbamic acid tert-butyl ester The title compound was prepared from rac-[(3,4-dichlorophenyl)-(methoxy-methyl-carbamoyl)-methyl]-carbamic acid tert-butyl ester (Intermediate 9) and 1-bromo-4-(trimethylsilyl)benzene with tert-butyl-lithium instead of n-butyl-lithium in analogy to Example 1a): MS (ISP): 452.0 and 454.0 (M+H)$^+$.

b) rac-erythro-[1-(3,4-Dichloro-phenyl)-2-hydroxy-2-(4-trimethylsilanyl-phenyl)-ethyl]-carbamic acid tert-butyl ester The title compound was prepared from rac-[1-(3,4-dichloro-phenyl)-2-oxo-2-(4-trimethylsilanyl-phenyl)-ethyl]-carbamic acid tert-butyl ester in analogy to Example 1c): MS (ISP): 454.0 and 456.1 (M+H)$^+$.

c) rac-erythro-[2-Amino-2-(3,4-dichloro-phenyl)-1-(4-trimethylsilanyl-phenyl)-ethanol trifluoroacetate The title compound was prepared from rac-erythro-[1-(3,4-dichloro-phenyl)-2-hydroxy-2-(4-trimethylsilanyl-phenyl)-ethyl]-carbamic acid tert-butyl ester in analogy to Example 1d): MS (ISP): 354.2 and 356.1 (M+H)$^+$.

Example 36 rac-erythro-[1-Amino-2-biphenyl-4-yl-1-(4-chloro-phenyl)-propan-2-ol trifluoroacetate

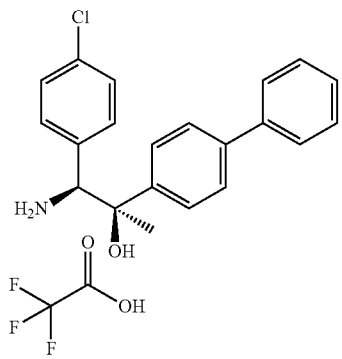

a) rac-[2-Biphenyl-4-yl-1-(4-chloro-phenyl)-2-oxo-ethyl]-carbamic acid tert-butyl ester A solution of 647 mg (1.97 mmol)rac-[(4-chloro-phenyl)-(methoxy-methyl-carbamoyl)-methyl]-carbamic acid tert-butyl ester (Intermediate 8) in 10 ml dry tetrahydrofuran was cooled to 0° C. and within 3 min 8.27 ml (4.13 mmol) 0.5M 4-biphenylmagnesium bromide solution in tetrahydrofuran were added. After stirring at 0° C. for 3 hours further 3.94 ml (1.97 mmol) 0.5M 4-biphenylmagnesium bromide solution in tetrahydrofuran were added and stirring at 0° C. continued for 1.5 hours. The reaction mixture was poured onto saturated aqueous ammonium chloride solution, diluted with water and extracted with ethyl acetate. The combined organic phases were washed with brine, dried over $Na_2SO_4$ and evaporated. The crude product was purified by flash-chromatography on silica gel with a gradient of heptane and 0% to 30% ethyl acetate: MS (ISN): 420.0 and 422.1 (M−H)$^-$.

b) rac-erythro-[2-Biphenyl-4-yl-1-(4-chloro-phenyl)-2-hydroxy-propyl]-carbamic acid tert-butyl ester A solution of 100 mg (0.237 mmol) rac-[2-biphenyl-4-yl-1-(4-chloro-phenyl)-2-oxo-ethyl]-carbamic acid tert-butyl ester in 2 ml dry tetrahydrofuran was cooled to 0° C. and within 3 min 0.500 mmol 3M methylmagnesium chloride solution in tetrahydrofuran were added. After stirring at 0° C. for 1 hour further 0.237 mmol 0.5M 3M methylmagnesium chloride solution in tetrahydrofuran were added and stirring at 0° C. continued for 1 hour. The reaction mixture was poured onto saturated aqueous ammonium chloride solution, diluted with water and extracted with ethyl acetate. The combined organic phases were washed with brine, dried over $Na_2SO_4$ and evaporated. Pure title compound was obtained: colorless solid; MS (ISP): 438.2 (M+H)$^+$ and 364.0 ((M-tBuOH)+H)$^+$.

c) rac-erythro-[1-Amino-2-biphenyl-4-yl-1-(4-chloro-phenyl)-propan-2-ol trifluoro-acetate The title compound was prepared from rac-erythro-[2-biphenyl-4-yl-1-(4-chloro-phenyl)-2-hydroxy-propyl]-carbamic acid tert-butyl ester in analogy to Example 1d): MS (ISP): 338.2 (M+H)$^+$.

Example 37 rac-erythro-[2-Amino-1-(4-tert-butyl-phenyl)-2-(3,4-dichloro-phenyl)-ethanol trifluoroacetate

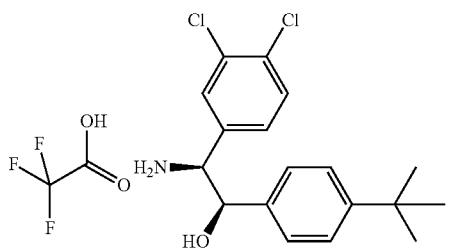

a) rac-[2-(4-tert-Butyl-phenyl)-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1-bromo-4-tert-butylbenzene in analogy to Example 1a): MS (ISP): 436.1 and 438.2 (M+H)$^+$.

b) rac-erythro-[2-(4-tert-Butyl-phenyl)-1-(3,4-dichloro-phenyl)-2-hydroxy-ethyl]-carbamic acid tert-butyl ester The title compound was prepared from rac-[2-(4-tert-butyl-phenyl)-1-(3,4-dichloro-phenyl)-2-oxo-ethyl]-carbamic acid tert-butyl ester in analogy to Example 1c): MS (ISP): 438.1 and 440.1 (M+H)$^+$.

c) rac-erythro-[2-Amino-1-(4-tert-butyl-phenyl)-2-(3,4-dichloro-phenyl)-ethanol trifluoroacetate The title compound was prepared from rac-erythro-[2-(4-tert-butyl-phenyl)-1-(3,4-dichloro-phenyl)-2-hydroxy-ethyl]-carbamic acid tert-butyl ester in analogy to Example 1d): MS (ISP): 338.0 and 340.1 (M+H)$^+$.

Example 38 rac-erythro-[2-Amino-2-(3,4-dichlorophenyl)-1-[4-(1,1,2,2-tetrafluoro-ethoxy)-phenyl]-ethanol

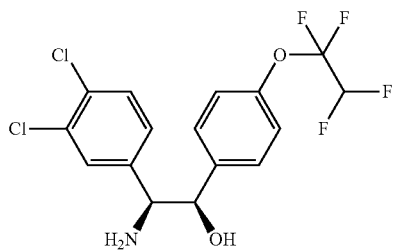 [SMILES: N[C@@H](c1ccc(Cl)c(Cl)c1)[C@H](O)c1ccc(OC(F)(F)C(F)F)cc1]

a) rac-[1-(3,4-Dichloro-phenyl)-2-oxo-2-[4-(1,1,2,2-tetrafluoro-ethoxy)-phenyl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1-iodo-4-(1,1,2,2-tetrafluoro-ethoxy)benzene in analogy to Example 1a): MS (ISN): 494.1 and 496.2 (M−H.

b) rac-2-Amino-2-(3,4-dichloro-phenyl)-1-[4-(1,1,2,2-tetra uoro-ethoxy)-phenyl]-ethanone hydrochloride To a solution of 150 mg (0.302 mmol) rac-[1-(3,4-dichloro-phenyl)-2-oxo-2-[4-(1,1,2,2-tetrafluoro-ethoxy)-phenyl]-ethyl]-carbamic acid tert-butyl ester in 5 ml methanol was added 0.5 ml of a saturated hydrogen chloride solution in ethanol and the mixture stirred at ambient temperature for 20 hours. Evaporation of the reaction mixture and trituration of the crude product in di-isopropyl ether provided the title compound: MS (ISP): 396.0 and 398.0 (M+H)$^+$.

c) rac-erythro-[2-Amino-2-(3,4-dichloro-phenyl)-1-[4-(1,1,2,2-tetrafluoro-ethoxy)-phenyl]-ethanol The title compound was prepared from rac-2-amino-2-(3,4-dichloro-phenyl)-1-[4-(1,1,2,2-tetrafluoro-ethoxy)-phenyl]-ethanone hydrochloride in analogy to Example 1c): MS (ISP): 398.0 and 400.0 (M+H)$^+$, 381.1 and 382.9 ((M-NH$_3$)+H)$^+$.

Example 39 rac-erythro-[2-(3,4-Dichloro-phenyl)-1-[4-(5-fluoro-pyridin-3-yl)-phenyl]-2-methylamino-ethanol hydrochloride

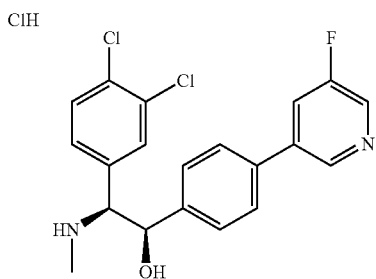 [SMILES: Cl ; CN[C@@H](c1ccc(Cl)c(Cl)c1)[C@H](O)c1ccc(-c2cncc(F)c2)cc1]

a) rac-erythro-[2-(tert-Butyl-dimethyl-silanyloxy)-1-(3,4-dichloro-phenyl)-2-(4-iodo-phenyl)-ethyl]-carbamic acid tert-butyl ester To a solution of 200 mg (0.394 mmol) rac-erythro-[1-(3,4-dichloro-phenyl)-2-hydroxy-2-(4-iodo-phenyl)-ethyl]-carbamic acid tert-butyl ester in 5 ml N,N-dimethylformamide were added 67.1 mg (0.985 mmol) imidazole and 71.3 mg (0.473 mmol) tert-butyldimethylsilyl chloride. The mixture was stirred at ambient temperature for 6 hours. Then 17.5 mg (0.143 mmol) 4-dimethylaminopyridine was added and the reaction kept at 60° C. for 24 hours. The reaction mixture was directly poured on a silica gel column and purified by flash-chromatography on with a heptane/ethyl acetate gradient with 0 to 25% ethyl acetate. The title compound was obtained as colorless gum.

b) rac-erythro-[2-(tert-Butyl-dimethyl-silanyloxy)-1-(3,4-dichloro-phenyl)-2-(4-iodo-phenyl)-ethyl]-methyl-carbamic acid tert-butyl ester The title compound was prepared from rac-erythro-[2-(tert-butyl-dimethyl-silanyloxy)-1-(3,4-dichloro-phenyl)-2-(4-iodo-phenyl)-ethyl]-carbamic acid tert-butyl ester by treatment with sodium hydride in tetrahydrofuran at ambient temperature for 5 minutes then methyl iodide was added and the reaction mixture stirred at ambient temperature for 4 h. Usual workup and flash-chromatography provided the title compound: MS (ISP): 635.9 and 637.8 (M+H)$^+$.

c) rac-erythro-[2-(tert-Butyl-dimethyl-silanyloxy)-1-(3,4-dichloro-phenyl)-2-[4-(5-fluoro-pyridin-3-yl)-phenyl]-ethyl]-methyl-carbamic acid tert-butyl ester The title compound was prepared from rac-erythro-[2-(tert-butyl-dimethyl-silanyloxy)-1-(3,4-dichloro-phenyl)-2-(4-iodo-phenyl)-ethyl]-methyl-carbamic acid tert-butyl ester and 5-fluoropyridine-3-boronic acid in analogy to Example 1b): MS (ISP): 605.1 (M+H)$^+$.

d) rac-erythro-[2-(3,4-Dichloro-phenyl)-1-[4-(5-fluoro-pyridin-3-yl)-phenyl]-2-methylamino-ethanol hydrochloride The title compound was prepared from rac-erythro-[2-(tert-butyl-dimethyl-silanyloxy)-1-(3,4-dichloro-phenyl)-2-[4-(5-fluoro-pyridin-3-yl)-phenyl]-ethyl]-methyl-carbamic acid tert-butyl ester by stirring with a hydrogen chloride solution in methanol at 50° C. for 24 hours. Evaporation of the reaction mixture and trituration of the crude product in di-isopropyl ether provided pure title compound: MS (ISP): 391.2 and 393.1 (M+H)$^+$.

Example 40 rac-erythro-[2-Amino-2-(3,4-dichloro-phenyl)-1-[4-(tetrahydro-pyran-4-yloxy)-phenyl]-ethanol

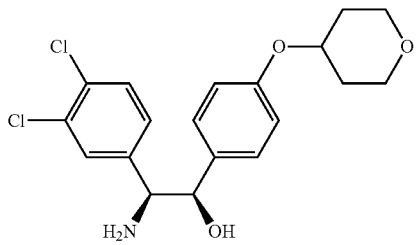 [SMILES: N[C@@H](c1ccc(Cl)c(Cl)c1)[C@H](O)c1ccc(OC2CCOCC2)cc1]

a) rac-1-(3,4-Dichloro-phenyl)-2-oxo-2-[4-(tetrahydro-pyran-4-yloxy)-phenyl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 4-(4-iodophenoxy) tetrahydropyran in analogy to Example 1a): MS (ISP): 480.2 and 482.1 (M+H)+, 424.1 and 426.0 ((M-isobutene)+H)+ (100%), 380.1 and 382.0 ((M-Boc)+H)+ (94%).

b) rac-[2-Amino-2-(3,4-dichloro-phenyl)-1-[4-(tetrahydro-pyran-4-yloxy)-phenyl-ethanone hydrochloride The title compound was prepared from rac-1-(3,4-dichloro-phenyl)-2-oxo-2-[4-(tetrahydro-pyran-4-yloxy)-phenyl]-ethyl]-carbamic acid tert-butyl ester in analogy to Example 38b): MS (ISP): 380.1 and 382.1 (M+H)+.

c) rac-erythro-[2-Amino-2-(3,4-dichloro-phenyl)-1-[4-(tetrahydro-pyran-4-yloxy)-phenyl]-ethanol The title compound was prepared from rac-[2-amino-2-(3,4-dichloro-phenyl)-1-[4-(tetrahydro-pyran-4-yloxy)-phenyl]-ethanone hydrochloride in analogy to Example 1c): MS (ISP): 382.1 and 384.1 (M+H)+.

Example 41

(1R,2S or 1S,2R)-[2-Amino-2-(3,4-dichloro-phenyl)-1-[4-(tetrahydro-pyran-4-yloxy)-phenyl]-ethanol

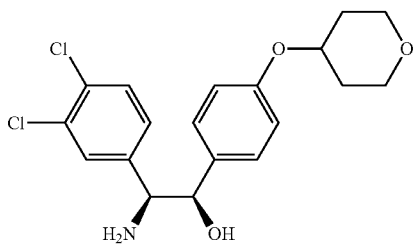 [SMILES: N[C@@H](c1ccc(Cl)c(Cl)c1)[C@H](O)c1ccc(OC2CCOCC2)cc1]

The title compound was obtained by chromatographic separation of rac-erythro-[2-amino-2-(3,4-dichloro-phenyl)-1-[4-(tetrahydro-pyran-4-yloxy)-phenyl]-ethanol on a Chiralpak AD column with eluent heptane/ethanol 70:30 as 1st peak, colorless powder: MS (ISP): 382.1 and 384.1 (M+H)+, 364.1 and 365.9 ((M–H$_2$O)+H)+ (100%).

Example 42 rac-erythro-[rac-2-Amino-2-(3,4-dichloro-phenyl)-1-[4-(tetrahydro-furan-3-yloxy)-phenyl]-ethanol

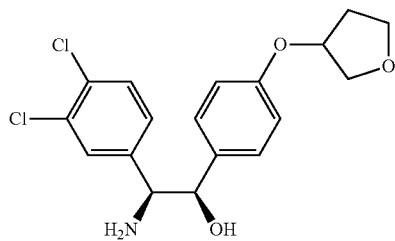 [SMILES: N[C@@H](c1ccc(Cl)c(Cl)c1)[C@H](O)c1ccc(OC2CCOC2)cc1]

a) rac-[2-[4-(tert-Butyl-dimethyl-silanyloxy)-phenyl]-1-(3,4-dichloro-phenyl)-2-oxo-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and (4-bromo-phenoxy)-tert-butyl-dimethyl-silane in analogy to Example 1a): MS (ISP): 510.3 and 512.2 (M+H)+, 410.1 and 412.1 ((M-Boc)+H)+ (100%).

b) rac-[1-(3,4-Dichloro-phenyl)-2-(4-hydroxy-phenyl)-2-oxo-ethyl]-carbamic acid tert-butyl ester The title compound was prepared from rac-[2-[4-(tert-butyl-dimethyl-silanyloxy)-phenyl]-1-(3,4-dichloro-phenyl)-2-oxo-ethyl]-carbamic acid tert-butyl ester in analogy to Example 9b): MS (ISN): 394.2 and 396.2 (M–H)–.

c) rac-[1-(3,4-Dichloro-phenyl)-2-oxo-2-[4-(tetrahydro-furan-3-yloxy)-phenyl]-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and rac-3-hydroxy-tetrahydrofuran in analogy to Example 9c): MS (ISP): 466.1 and 468.3 (M+H)+, 366.0 and 368.0 ((M-Boc)+H)+ (100%).

d) rac-[2-Amino-2-(3,4-dichloro-phenyl)-1-[4-(tetrahydro-furan-3-yloxy)-phenyl]-ethanone hydrochloride The title compound was prepared from rac-[1-(3,4-dichloro-phenyl)-2-oxo-2-[4-(tetrahydro-furan-3-yloxy)-phenyl]-ethyl]-carbamic acid tert-butyl ester in analogy to Example 38b): MS (ISP): 366.0 and 368.0 (M+H)+.

e) rac-erythro-[rac-2-Amino-2-(3,4-dichloro-phenyl)-1-[4-(tetrahydro-furan-3-yloxy)-phenyl]-ethanol The title compound was prepared from rac-[2-amino-2-(3,4-dichloro-phenyl)-1-[4-(tetrahydro-furan-3-yloxy)-phenyl]-ethanone hydrochloride in analogy to Example 1c): MS (ISP): 368.1 and 370.1 (M+H)+, 350.2 and 352.1 ((M–H$_2$O)+H)+ (100%).

Example 43 rac-erythro-[2-Amino-2-(3,4-dichloro-phenyl)-1-hydroxy-ethyl]-phenoxy]-2-chloromethyl-2-methyl-propan-1-ol hydrochloride

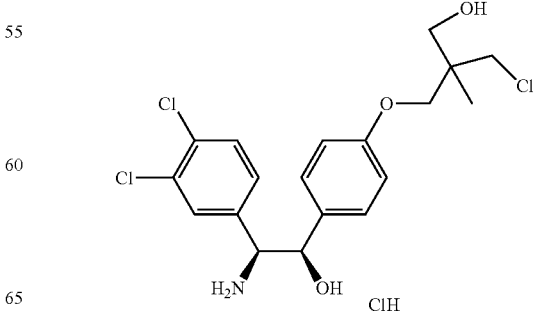

a) rac-[1-(3,4-Dichloro-phenyl)-2-[4-(3-methyl-oxetan-3-ylmethoxy)-phenyl]-2-oxo-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and (3-methyl-oxetan-3-yl)-methanol in analogy to Example 9c): MS (ISN): 478.1 (M−H)⁻.

b) rac-[2-Amino-1-[4-(3-chloro-2-hydroxymethyl-2-methyl-propoxy)-phenyl]-2-(3,4-dichloro-phenyl)-ethanone hydrochloride The title compound was prepared from rac-[1-(3,4-dichloro-phenyl)-2-[4-(3-methyl-oxetan-3-ylmethoxy)-phenyl]-2-oxo-ethyl]-carbamic acid tert-butyl ester in analogy to Example 38b): MS (ISN): 415.0 (M−H)⁻.

c) rac-erythro-[2-Amino-2-(3,4-dichloro-phenyl)-1-hydroxy-ethyl]-phenoxy]-2-chloro methyl-2-methyl-propan-1-ol hydrochloride The title compound was prepared from rac-[1-(3,4-dichloro-phenyl)-2-hydroxy-2-[4-(3-methyl-oxetan-3-ylmethoxy)-phenyl]-ethyl]-carbamic acid tert-butyl ester in analogy to Example 1c): MS (ISP): 418.2 and 420.0 (M+H)⁺, 400.2 and 402.2 ((M−H₂O)+H)⁺ (100%).

Example 44 rac-erythro-[2-Amino-2-(3,4-dichloro-phenyl)-1-[4-(1,1-dioxo-hexahydro-1λ⁶-thio-pyran-4-yloxy)-phenyl]-ethanol

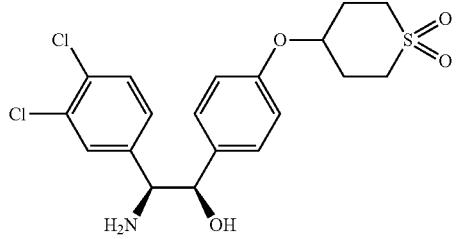 [SMILES: N[C@@H](c1ccc(Cl)c(Cl)c1)[C@H](O)c1ccc(OC2CCS(=O)(=O)CC2)cc1]

a) rac-[1-(3,4-Dichloro-phenyl)-2-oxo-2-[4-(tetrahydro-thiopyran-4-yloxy)-phenyl]-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and tetrahydro-2H-thiopyran-4-ol in analogy to Example 9c): MS (ISP): 496.2 and 498.1 (M+H)⁺, 396.1 and 397.9 ((M-Boc)+H)⁺ (100%).

b) rac-[1-(3,4-Dichloro-phenyl)-2-[4-(1,1-dioxo-hexahydro-1λ⁶-thiopyran-4-yloxy)-phenyl]-2-oxo-ethyl]-carbamic acid tert-butyl ester The title compound was prepared by oxidation of rac-[1-(3,4-dichloro-phenyl)-2-oxo-2-[4-(tetrahydro-thiopyran-4-yloxy)-phenyl]-ethyl]-carbamic acid tert-butyl ester with m-chloro-perbenzoic acid in dichloromethane at ambient temperature for 18 h: MS (ISN): 526.1 and 527.9 (M−H)⁻.

c) rac-[2-Amino-2-(3,4-dichloro-phenyl)-1-[4-(1,1-dioxo-hexahydro-1λ⁶-thiopyran-4-yloxy)-phenyl]-ethanone hydrochloride The title compound was prepared from rac-[1-(3,4-dichloro-phenyl)-2-[4-(1,1-dioxo-hexahydro-1λ⁶-thiopyran-4-yloxy)-phenyl]-2-oxo-ethyl]carbamic acid tert-butyl ester in analogy to Example 38b): MS (ISP): 428.2 and 430.2 (M+H)⁺.

d) rac-erythro-2-Amino-2-(3,4-dichloro-phenyl)-1-[4-(1,1-dioxo-hexahydro-1λ⁶-thiopyran-4-yloxy)-phenyl]-ethanol The title compound was prepared from rac-[2-Amino-2-(3,4-dichloro-phenyl)-1-[4-(1,1-dioxo-hexahydro-1λ⁶-thiopyran-4-yloxy)-phenyl]ethanone hydrochloride in analogy to Example 1c): MS (ISP): 430.2 and 432.1 (M+H)⁺, 412.0 and 414.1 ((M−H₂O)+H)⁺ (100%).

Example 45 rac-erythro-[2-Amino-2-(3,4-dichloro-phenyl)-1-[4-(tetrahydro-pyran-4-ylmethoxy)-phenyl]-ethanol

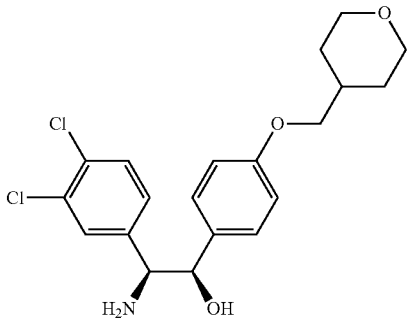 [SMILES: N[C@@H](c1ccc(Cl)c(Cl)c1)[C@H](O)c1ccc(OCC2CCOCC2)cc1]

a) rac-[1-(3,4-Dichloro-phenyl)-2-oxo-2-[4-(tetrahydro-pyran-4-ylmethoxy)-phenyl]-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and tetrahydro-2H-pyran-4-yl-methanol in analogy to Example 9c): MS (ISP): 494.2 and 496.1 (M+H)⁺.

b) rac-[2-Amino-2-(3,4-dichloro-phenyl)-1-[4-(tetrahydro-pyran-4-ylmethoxy)-phenyl]-ethanone hydrochloride The title compound was prepared from rac-[1-(3,4-dichloro-phenyl)-2-oxo-2-[4-(tetrahydro-pyran-4-ylmethoxy)-phenyl]-ethyl]-carbamic acid tert-butyl ester in analogy to Example 38b): MS (ISP): 394.1 and 396.1 (M+H)⁺.

c) rac-erythro-[2-Amino-2-(3,4-dichloro-phenyl)-1-[4-(tetrahydro-pyran-4-ylmethoxy)-phenyl]-ethanol The title compound was prepared from rac-[2-amino-2-(3,4-dichloro-phenyl)-1-[4-(tetrahydro-pyran-4-ylmethoxy)-phenyl]-ethanone hydrochloride in analogy to Example 1c): MS (ISP): 396.1 and 398.0 (M+H)⁺, 378.2 and 380.1 ((M−H₂O)+H)⁺ (100%).

Example 46 rac-erythro-[1-(4-[4-[2-Amino-2-(3,4-dichloro-phenyl)-1-hydroxy-ethyl]-phenoxy]-piperidin-1-yl)-ethanone

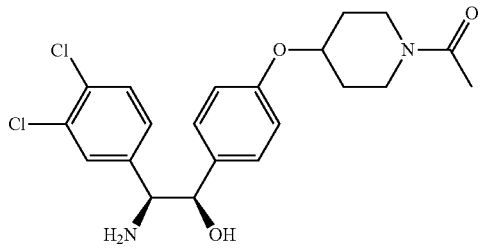 [SMILES: CC(=O)N1CCC(Oc2ccc([C@@H](O)[C@@H](N)c3ccc(Cl)c(Cl)c3)cc2)CC1]

a) rac-[2-[4-(1-Acetyl-piperidin-4-yloxy)-phenyl]-1-(3,4-dichloro-phenyl)-2-oxo-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and 1-(4-hydroxy-piperidin-1-yl)-ethanone in analogy to Example 9c): MS (ISP): 521.2 and 523.2 (M+H)+; MS (ISN): 519.1 and 521.2 (M−H)−.

b) rac-[1-[4-(1-Acetyl-piperidin-4-yloxy)-phenyl]-2-amino-2-(3,4-dichloro-phenyl)-ethanone hydrochloride The title compound was prepared from rac-[2-[4-(1-acetyl-piperidin-4-yloxy)-phenyl]-1-(3,4-dichloro-phenyl)-2-oxo-ethyl]-carbamic acid tert-butyl ester in analogy to Example 38b): MS (ISP): 421.0 and 423.1 (M+H)+.

c) rac-erythro-[1-(4-[4-[2-Amino-2-(3,4-dichloro-phenyl)-1-hydroxy-ethyl]-phenoxy]-piperidin-1-yl)-ethanone The title compound was prepared from rac-[1-[4-(1-acetyl-piperidin-4-yloxy)-phenyl]-2-amino-2-(3,4-dichloro-phenyl)-ethanone hydrochloride in analogy to Example 1c): MS (ISP): 423.2 and 425.0 (M+H)+, 405.2 and 407.4 ((M−H2O)+H)+ (100%).

Example 47 rac-erythro-[2-Amino-2-(3,4-dichloro-phenyl)-1-[4-(2,2,2-trifluoro-ethoxy)-phenyl]-ethanol

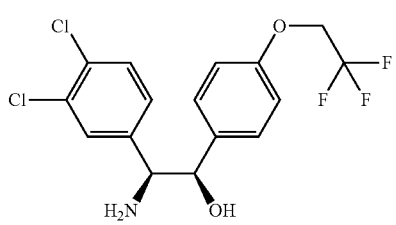 [SMILES: N[C@@H](c1ccc(Cl)c(Cl)c1)[C@H](O)c1ccc(OCC(F)(F)F)cc1]

a) rac-[1-(3,4-Dichloro-phenyl)-2-oxo-2-[4-(2,2,2-trifluoro-ethoxy)-phenyl]-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1-bromo-4-(2,2,2-trifluoro-ethoxy)-benzene in analogy to Example 1a): MS (ISP): 478.1 and 480.1 (M+H)+, 378.2 and 380.0 ((M-Boc)+H)+ (100%).

b) rac-[2-Amino-2-(3,4-dichloro-phenyl)-1-[4-(2,2, 2-trifluoro-ethoxy)-phenyl-ethanone hydrochloride The title compound was prepared from rac-[1-(3,4-dichloro-phenyl)-2-oxo-2-[4-(2,2,2-trifluoro-ethoxy)-phenyl]-ethyl]-carbamic acid tert-butyl ester in analogy to Example 38b): MS (ISP): 378.1 and 380.0 (M+H)+.

c) rac-erythro-[2-Amino-2-(3,4-dichloro-phenyl)-1-[4-(2,2,2-trifluoro-ethoxy)-phenyl]-ethanol The title compound was prepared from rac-[2-amino-2-(3,4-dichloro-phenyl)-1-[4-(2,2,2-trifluoro-ethoxy)-phenyl]-ethanone hydrochloride in analogy to Example 1c): MS (ISP): 380.1 and 381.9 (M+H)+, 362.2 and 364.0 ((M−H2O)+H)+ (100%).

Example 48 rac-erythro-[2-Amino-2-(4-chloro-phenyl)-1-(4-cyclopentyloxy-phenyl)-ethanol hydrochloride

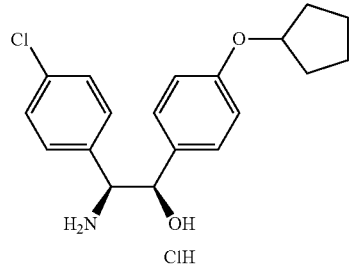 [SMILES: N[C@@H](c1ccc(Cl)cc1)[C@H](O)c1ccc(OC2CCCC2)cc1 ; Cl]

a) rac-[1-(4-Chloro-phenyl)-2-(4-cyclopentyloxy-phenyl)-2-oxo-ethyl]-carbamic acid tert-butyl ester The title compound was prepared from rac-[1-(4-chloro-phenyl)-2-(4-hydroxy-phenyl)-2-oxo-ethyl]-carbamic acid tert-butyl ester and cyclopentanol in analogy to Example 9c): MS (ISP): 466.1 and 468.3 (M+H)+, 366.0 and 368.0 ((M-Boc)+H)+ (100%).

b) rac-erythro-[1-(4-Chloro-phenyl)-2-(4-cyclopentyloxy-phenyl)-2-hydroxy-ethyl]-carbamic acid tert-butyl ester The title compound was prepared from rac-[1-(4-chloro-phenyl)-2-(4-cyclopentyloxy-phenyl)-2-oxo-ethyl]-carbamic acid tert-butyl ester in analogy to Example 1c): MS (ISN): 430.3 (M−H)−.

c) rac-erythro-[2-Amino-2-(4-chloro-phenyl)-1-(4-cyclopentyloxy-phenyl)-ethanol hydrochloride The title compound was prepared from rac-erythro-[1-(4-chloro-phenyl)-2-(4-cyclopentyloxy-phenyl)-2-hydroxy-ethyl]-carbamic acid tert-butyl ester in analogy to Example 2d): MS (ISP): 332.1 and 314.0 (M+H)−.

Example 49 rac-erythro-[2-Amino-1-(4-cyclopropylmethoxy-phenyl)-2-(3,4-dichloro-phenyl)-ethanol

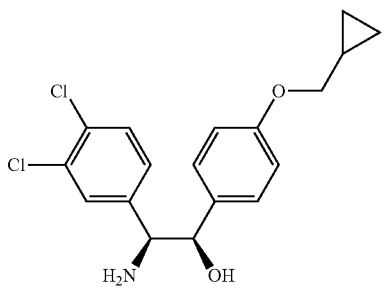 [SMILES: N[C@@H](c1ccc(Cl)c(Cl)c1)[C@H](O)c1ccc(OCC2CC2)cc1]

a) rac-[2-(4-Cyclopropylmethoxy-phenyl)-1-(3,4-dichloro-phenyl)-2-oxo-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and cyclopropyl-methanol in analogy to Example 9c): MS (ISP): 450.2 and 452.0 (M+H)$^+$, 350.2 and 352.2 ((M-Boc)+H)$^+$ (100%).

b) rac-[2-Amino-1-(4-cyclopropylmethoxy-phenyl)-2-(3,4-dichloro-phenyl)-ethanone hydrochloride The title compound was prepared from rac-[2-(4-cyclopropylmethoxy-phenyl)-1-(3,4-dichloro-phenyl)-2-oxo-ethyl]-carbamic acid tert-butyl ester in analogy to Example 38b): MS (ISP): 350.2 and 352.2 (M+H)$^+$.

c) rac-erythro-[2-Amino-1-(4-cyclopropylmethoxy-phenyl)-2-(3,4-dichloro-phenyl)-ethanol The title compound was prepared from rac-[2-amino-1-(4-cyclopropylmethoxy-phenyl)-2-(3,4-dichloro-phenyl)-ethanone hydrochloride in analogy to Example 1c): MS (ISP): 352.2 (M+H)$^+$, 334.2 and 336.2 ((M-H$_2$O)+H)$^+$ (100%).

Example 50 rac-erythro-2-Amino-2-(3,4-dichloro-phenyl)-1-(4-isobutoxy-phenyl)-ethanol

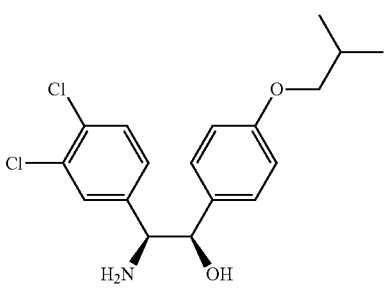 [SMILES: CC(C)COc1ccc([C@@H](O)[C@@H](N)c2ccc(Cl)c(Cl)c2)cc1]

a) rac-[1-(3,4-Dichloro-phenyl)-2-(4-isobutoxy-phenyl)-2-oxo-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and 2-methyl-1-propanol in analogy to Example 9c): MS (ISP): 452.1 and 454.1 (M+H)$^+$, 352.1 and 354.2 ((M-Boc)+H)$^+$ (100%).

b) rac-2-Amino-2-(3,4-dichloro-phenyl)-1-(4-isobutoxy-phenyl)-ethanone hydrochloride The title compound was prepared from rac-[1-(3,4-dichloro-phenyl)-2-(4-isobutoxy-phenyl)-2-oxo-ethyl]-carbamic acid tert-butyl ester in analogy to Example 38b): MS (ISP): 352.2 and 354.1 (M+H)$^+$.

c) rac-erythro-2-Amino-2-(3,4-dichloro-phenyl)-1-(4-isobutoxy-phenyl)-ethanol The title compound was prepared from rac-2-amino-2-(3,4-dichloro-phenyl)-1-(4-isobutoxy-phenyl)-ethanone hydrochloride in analogy to Example 1c): MS (ISP): 336.3 and 338.2 ((M-H$_2$O)+H)$^+$ (100%).

Example 51 rac-erythro-2-Amino-1-(4-sec-butoxy-phenyl)-2-(3,4-dichloro-phenyl)-ethanol

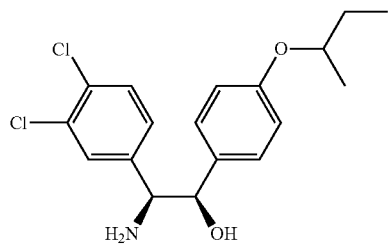 [SMILES: CCC(C)Oc1ccc([C@@H](O)[C@@H](N)c2ccc(Cl)c(Cl)c2)cc1]

a) rac-[2-(4-sec-Butoxy-phenyl)-1-(3,4-dichloro-phenyl)-2-oxo-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and 2-butanol in analogy to Example 9c): MS (ISP): 452.1 and 454.0 (M+H)$^+$, 352.1 and 354.1 ((M-Boc)+H)$^+$ (100%).

b) rac-2-Amino-1-(4-sec-butoxy-phenyl)-2-(3,4-dichloro-phenyl)-ethanone hydrochlo-ride The title compound was prepared from rac-[2-(4-sec-butoxy-phenyl)-1-(3,4-dichloro-phenyl)-2-oxo-ethyl]-carbamic acid tert-butyl ester in analogy to Example 38b): MS (ISP): 352.1 and 354.1 (M+H)$^+$.

c) rac-erythro-2-Amino-1-(4-sec-butoxy-phenyl)-2-(3,4-dichloro-phenyl)-ethanol The title compound was prepared from rac-2-amino-1-(4-sec-butoxy-phenyl)-2-(3,4-dichloro-phenyl)-ethanone hydrochloride in analogy to Example 1c): MS (ISP): 336.2 and 338.0 ((M-H$_2$O)+H)$^+$ (100%).

Example 52 rac-erythro-2-Amino-2-(3,4-dichloro-phenyl)-1-[4-(3,3,3-trifluoro-propoxy)-phenyl]-ethanol

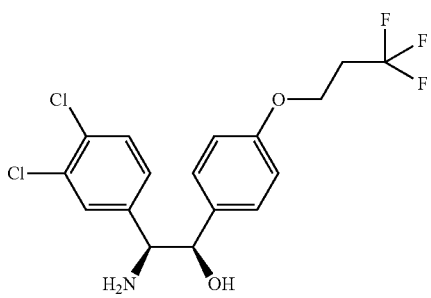 [SMILES: N[C@@H](c1ccc(Cl)c(Cl)c1)[C@H](O)c1ccc(OCCC(F)(F)F)cc1]

a) rac-[1-(3,4-Dichloro-phenyl)-2-oxo-2-[4-(3,3,3-trifluoro-propoxy)-phenyl]-ethyl]-carbamic acid tert-butyl ester The title compound was prepared from rac-[1-(3,4-dichloro-phenyl)-2-(4-hydroxy-phenyl)-2-oxo-ethyl]-carbamic acid tert-butyl ester and 3,3,3-trifluoropropanol in analogy to Example 9c): MS (ISP): 492.2 and 494.2 (M+H)$^+$, 392.0 and 394.0 ((M-Boc)+H)$^+$ (100%).

b) rac-2-Amino-2-(3,4-dichloro-phenyl)-1-[4-(3,3,3-trifluoro-propoxy)-phenyl]-ethanone hydrochloride The title compound was prepared from rac-[1-(3,4-dichloro-phenyl)-2-oxo-2-[4-(3,3,3-trifluoro-propoxy)-phenyl]-ethyl]-carbamic acid tert-butyl ester in analogy to Example 2d): MS (ISP): 392.0 and 393.9 (M+H)$^+$.

c) rac-erythro-2-Amino-2-(3,4-dichloro-phenyl)-1-[4-(3,3,3-trifluoro-propoxy)-phenyl]-ethanol The title compound was prepared from rac-2-amino-2-(3,4-dichloro-phenyl)-1-[4-(3,3,3-trifluoro-propoxy)-phenyl]-ethanone hydrochloride in analogy to Example 1c): MS (ISP): 394.0 and 396.0 (M+H)$^+$, 376.3 and 378.1 ((M-H$_2$O)+H)$^+$ (100%).

Example 53 rac-erythro-2-Amino-2-(4-chloro-phenyl)-1-(4-cyclohexyloxy-phenyl)-ethanol

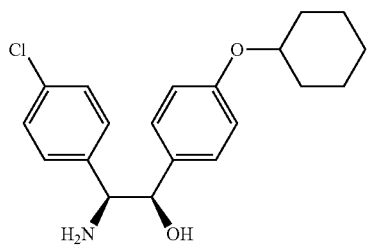 [SMILES: N[C@@H](c1ccc(Cl)cc1)[C@H](O)c1ccc(OC2CCCCC2)cc1]

a) rac-[1-(4-Chloro-phenyl)-2-(4-cyclohexyloxy-phenyl)-2-oxo-ethyl]-carbamic acid tert-butyl ester The title compound was prepared from rac-[1-(4-chloro-phenyl)-2-(4-hydroxy-phenyl)-2-oxo-ethyl]-carbamic acid tert-butyl ester and cyclohexanol in analogy to Example 9c): MS (ISN): 442.3 (M-H)$^-$; MS (ISP): 444.2 (M+H)$^+$, 344.1 ((M-Boc)+H)$^+$ (100%).

b) rac-2-Amino-2-(4-chloro-phenyl)-1-(4-cyclohexyloxy-phenyl)-ethanone hydrochloride The title compound was prepared from rac-[1-(4-chloro-phenyl)-2-(4-cyclohexyloxy-phenyl)-2-oxo-ethyl]-carbamic acid tert-butyl ester in analogy to Example 38b): MS (ISP): 344.1 (M+H)$^+$.

c) rac-erythro-2-Amino-2-(4-chloro-phenyl)-1-(4-cyclohexyloxy-phenyl)-ethanol The title compound was prepared from rac-2-amino-2-(4-chloro-phenyl)-1-(4-cyclohexyloxy-phenyl)-ethanone hydrochloride in analogy to Example 1c): MS (ISP): 346.2 (M+H)$^+$, 328.2 ((M-H$_2$O)+H)$^+$ (100%).

Example 54 rac-erythro-[2-Amino-2-(3-chloro-4-methyl-phenyl)-1-[4-(tetrahydro-pyran-4-yloxy)-phenyl]-ethanol

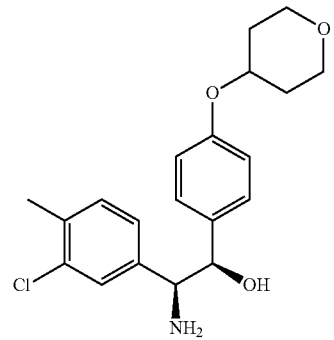 [SMILES: Cc1ccc([C@H](N)[C@H](O)c2ccc(OC3CCOCC3)cc2)cc1Cl]

a) rac-[2-[4-(tert-Butyl-dimethyl-silanyloxy)-phenyl]-1-(3-chloro-4-methyl-phenyl)-2-oxo-ethyl]-carbamic acid tert-butyl ester The title compound was prepared from rac-[(3-chloro-4-methyl-phenyl)-(methoxy-methyl-carbamoyl)-methyl]-carbamic acid tert-butyl ester (Intermediate 4) and (4-bromo-phenoxy)-tert-butyl-dimethyl-silane in analogy to Example 1a): MS (ISP): 374.3 ((M-Si(CH$_3$)$_2$C(CH$_3$)$_3$)+H)$^+$ (100%).

b) rac-[1-(3-Chloro-4-methyl-phenyl)-2-(4-hydroxy-phenyl)-2-oxo-ethyl]-carbamic acid tert-butyl ester The title compound was prepared from rac-[2-[4-(tert-butyl-dimethyl-silanyloxy)-phenyl]-1-(3-chloro-4-methyl-phenyl)-2-oxo-ethyl]-carbamic acid tert-butyl ester in analogy to Example 9b): MS (ISN): 374.3 (M-H)$^-$.

c) rac-[1-(3-Chloro-4-methyl-phenyl)-2-oxo-2-[4-(tetrahydro-pyran-4-yloxy)-phenyl]-ethyl]-carbamic acid tert-butyl ester The title compound was prepared from rac-[1-(3-chloro-4-methyl-phenyl)-2-(4-hydroxy-phenyl)-2-oxo-ethyl]-carbamic acid tert-butyl ester and tetrahydro-4H-pyran-4-ol in analogy to Example 9c): MS (ISN): 458.5 (M−H)⁻.

d) rac-[2-Amino-2-(3-chloro-4-methyl-phenyl)-1-[4-(tetrahydro-pyran-4-yloxy)-phenyl]-ethanone hydrochloride The title compound was prepared from rac-[1-(3-chloro-4-methyl-phenyl)-2-oxo-2-[4-(tetrahydro-pyran-4-yloxy)-phenyl]-ethyl]-carbamic acid tert-butyl ester in analogy to Example 38b): MS (ISN): 358.3 (M−H)⁻.

e) rac-erythro-[2-Amino-2-(3-chloro-4-methyl-phenyl)-1-[4-(tetrahydro-pyran-4-yloxy)-phenyl]-ethanol The title compound was prepared from rac-[2-amino-2-(3-chloro-4-methyl-phenyl)-1-[4-(tetrahydro-pyran-4-yloxy)-phenyl]-ethanone hydrochloride in analogy to Example 1c): MS (ISP): 362.3 (M+H)⁺.

Example 55 rac-erythro-[2-Amino-2-(3-chloro-4-methyl-phenyl)-1-[4-(tetrahydro-furan-3-yloxy)-phenyl]-ethanol

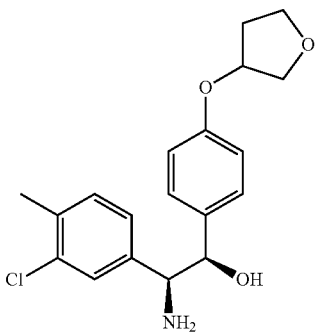 [SMILES: Cc1ccc([C@H](N)[C@H](O)c2ccc(OC3CCOC3)cc2)cc1Cl]

a) rac-[1-(3-Chloro-4-methyl-phenyl)-2-oxo-2-[4-(tetrahydro-furan-3-yloxy)-phenyl]-ethyl]-carbamic acid tert-butyl ester The title compound was prepared from rac-[1-(3-chloro-4-methyl-phenyl)-2-(4-hydroxy-phenyl)-2-oxo-ethyl]-carbamic acid tert-butyl ester and rac-3-hydroxy-tetrahydrofuran in analogy to Example 9c): MS (ISN): 444.3 (M−H)⁻.

b) rac-[2-Amino-2-(3-chloro-4-methyl-phenyl)-1-[4-(tetrahydro-furan-3-yloxy)-phenyl]-ethanone hydrochloride The title compound was prepared from rac-[1-(3-chloro-4-methyl-phenyl)-2-oxo-2-[4-(tetrahydro-furan-3-yloxy)-phenyl]-ethyl]-carbamic acid tert-butyl ester in analogy to Example 38b): MS (ISP): 346.1 (M+H)⁺.

c) rac-erythro-[2-Amino-2-(3-chloro-4-methyl-phenyl)-1-[4-(tetrahydro-furan-3-yloxy)-phenyl]-ethanol The title compound was prepared from rac-[2-amino-2-(3-chloro-4-methyl-phenyl)-1-[4-(tetrahydro-furan-3-yloxy)-phenyl]-ethanone hydrochloride in analogy to Example 1c): MS (ISP): 348.2 (M+H)⁺.

Example 56 rac-erythro-2-Amino-2-(3-chloro-4-methylphenyl)-1-(4-isopropoxy-phenyl)-ethanol

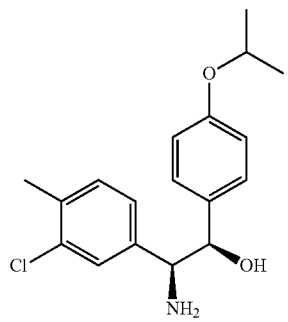 [SMILES: Cc1ccc([C@H](N)[C@H](O)c2ccc(OC(C)C)cc2)cc1Cl]

a) rac-[1-(3-Chloro-4-methyl-phenyl)-2-(4-isopropoxy-phenyl)-2-oxo-ethylkarbamic acid tert-butyl ester The title compound was prepared from rac-[1-(3-chloro-4-methyl-phenyl)-2-(4-hydroxy-phenyl)-2-oxo-ethyl]-carbamic acid tert-butyl ester and isopropanol in analogy to Example 9c): MS (ISN): 416.4 (M−H)⁻.

b) rac-2-Amino-2-(3-chloro-4-methyl-phenyl)-1-(4-isopropoxy-phenyl)-ethanone hydro chloride The title compound was prepared from rac-[1-(3-chloro-4-methyl-phenyl)-2-(4-isopropoxy-phenyl)-2-oxo-ethyl]-carbamic acid tert-butyl ester in analogy to Example 38b): MS (ISP): 318.2 (M+H)⁺.

c) rac-erythro-2-Amino-2-(3-chloro-4-methyl-phenyl)-1-(4-isopropoxy-phenyl)-ethanol The title compound was prepared from rac-[2-amino-2-(3-chloro-4-methyl-phenyl)-1-(4-isopropoxy-phenyl)-ethanone hydrochloride in analogy to Example 1c): MS (ISP): 320.1 (M+H)⁺.

Example 57 rac-erythro-2-Amino-2-(3-fluoro-4-methyl-phenyl)-1-[4-(tetrahydro-pyran-4-yloxy)-phenyl]-ethanol

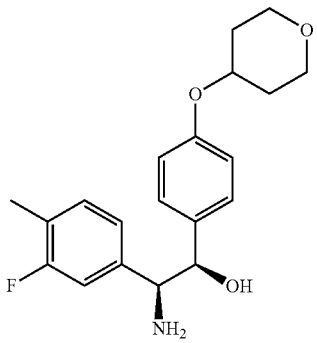 [SMILES: Cc1ccc([C@H](N)[C@H](O)c2ccc(OC3CCOCC3)cc2)cc1F]

a) rac-[2-[4-(tert-Butyl-dimethyl-silanyloxy)-phenyl]-1-(3-fluoro-4-methyl-phenyl)-2-oxo-ethyl]-carbamic acid tert-butyl ester The title compound was prepared from rac-[(3-fluoro-4-methyl-phenyl)-(methoxy-methyl-carbamoyl)-methyl]-carbamic acid tert-butyl ester (Intermediate 7) and (4-bromo-phenoxy)-tert-butyl-dimethyl-silane in analogy to Example 1a): MS (ISP): 358.3 ((M−Si(CH$_3$)$_2$C(CH$_3$)$_3$)+H)$^+$ (100%).

b) rac-[1-(3-Fluoro-4-methyl-phenyl)-2-(4-hydroxy-phenyl)-2-oxo-ethyl]-carbamic acid tea-butyl ester The title compound was prepared from rac-[2-[4-(tert-butyl-dimethyl-silanyloxy)-phenyl]-1-(3-fluoro-4-methyl-phenyl)-2-oxo-ethyl]-carbamic acid tert-butyl ester in analogy to Example 9b): MS (ISN): 358.3 (M−H)$^−$.

c) rac-[1-(3-Fluoro-4-methyl-phenyl)-2-oxo-2-[4-(tetrahydro-pyran-4-yloxy)-phenyl]-ethyl]-carbamic acid tert-butyl ester The title compound was prepared from rac-[1-(3-fluoro-4-methyl-phenyl)-2-(4-hydroxy-phenyl)-2-oxo-ethyl]-carbamic acid tert-butyl ester and tetrahydro-4H-pyran-4-ol in analogy to Example 9c): MS (ISN): 442.4 (M−H)$^−$.

d) rac-2-Amino-2-(3-fluoro-4-methyl-phenyl)-1-[4-(tetrahydro-pyran-4-yloxy)-phenyl]-ethanone hydrochloride The title compound was prepared from rac-[1-(3-fluoro-4-methyl-phenyl)-2-oxo-2-[4-(tetrahydro-pyran-4-yloxy)-phenyl]-ethyl]-carbamic acid tert-butyl ester in analogy to Example 38b): MS (ISP): 344.1 (M+H)$^+$.

e) rac-erythro-2-Amino-2-(3-fluoro-4-methyl-phenyl)-1-[4-(tetrahydro-pyran-4-yloxy)-phenyl]-ethanol The title compound was prepared from rac-[2-amino-2-(3-fluoro-4-methyl-phenyl)-1-[4-(tetrahydro-pyran-4-yloxy)-phenyl]-ethanone hydrochloride in analogy to Example 1c): MS (ISP): 346.2 (M+H)$^+$.

Example 58 rac-erythro-2-Amino-2-(4-chloro-phenyl)-1-[4-(2-fluoro-1-fluoromethyl-ethoxy)-phenyl]-ethanol

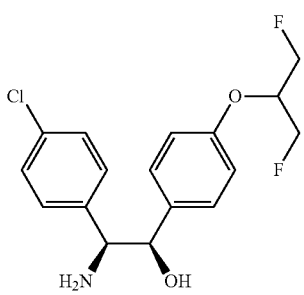 [SMILES: N[C@@H](c1ccc(Cl)cc1)[C@H](O)c1ccc(OC(CF)CF)cc1]

a) rac-[1-(4-Chloro-phenyl)-2-[4-(2-fluoro-1-fluoromethyl-ethoxy)-phenyl]-2-oxo-ethyl]-carbamic acid tert-butyl ester The title compound was prepared from rac-[1-(4-chloro-phenyl)-2-(4-hydroxy-phenyl)-2-oxo-ethyl]-carbamic acid tert-butyl ester and 1,3-difluoro-2-propanol in analogy to Example 9c): MS (ISN): 438.1 (M−H)$^−$.

b) rac-2-Amino-2-(4-chloro-phenyl)-1-[4-(2-fluoro-1-fluoromethyl-ethoxy)-phenyl]-ethanone hydrochloride The title compound was prepared from rac-[1-(4-chloro-phenyl)-2-[4-(2-fluoro-1-fluoromethyl-ethoxy)-phenyl]-2-oxo-ethyl]-carbamic acid tert-butyl ester in analogy to Example 38b): MS (ISP): 340.0 (M+H)$^+$.

c) rac-erythro-2-Amino-2-(4-chloro-phenyl)-1-[4-(2-fluoro-1-fluoromethyl-ethoxy)-phenyl]-ethanol The title compound was prepared from rac-[2-amino-2-(4-chloro-phenyl)-1-[4-(2-fluoro-1-fluoromethyl-ethoxy)-phenyl]-ethanone hydrochloride in analogy to Example 1c): MS (ISP): 342.1 (M+H)$^+$, 324.9 ((M−NH$_3$)+H)$^+$ (100%).

Example 59 rac-erythro-2-Amino-2-(4-chloro-phenyl)-1-[4-(tetrahydro-pyran-4-yloxy)-phenyl]-ethanol

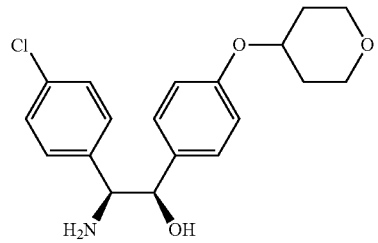 [SMILES: N[C@@H](c1ccc(Cl)cc1)[C@H](O)c1ccc(OC2CCOCC2)cc1]

a) rac-[1-(4-Chloro-phenyl)-2-oxo-2-[4-(tetrahydro-pyran-4-yloxy)-phenyl]-ethyl]-carbamic acid tert-butyl ester The title compound was prepared from rac-[1-(4-chloro-phenyl)-2-(4-hydroxy-phenyl)-2-oxo-ethyl]-carbamic acid tert-butyl ester and tetrahydro-4H-pyran-4-ol in analogy to Example 9c): MS (ISN): 444.3 (M−H)$^−$.

b) rac-2-Amino-2-(4-chloro-phenyl)-1-[4-(tetrahydro-pyran-4-yloxy)-phenyl]-ethanone hydrochloride The title compound was prepared from rac-[1-(4-chloro-phenyl)-2-oxo-2-[4-(tetrahydro-pyran-4-yloxy)-phenyl]-ethyl]-carbamic acid tert-butyl ester in analogy to Example 38b): MS (ISP): 346.1 (M+H)$^+$.

c) rac-erythro-2-Amino-2-(4-chloro-phenyl)-1-[4-(tetrahydro-pyran-4-yloxy)-phenyl]-ethanol The title compound was prepared from rac-[2-amino-2-(4-chloro-phenyl)-1-[4-(2-fluoro-1-fluoromethyl-ethoxy)-phenyl]-ethanone hydrochloride in analogy to Example 1c): MS (ISP): 348.2 (M+H)$^+$, 330.2 ((M−H$_2$O)+H)$^+$ (100%).

Example 60 rac-erythro-2-Amino-2-(4-chloro-phenyl)-1-(3'-methoxymethyl-biphenyl-4-yl)-ethanol hydrochloride

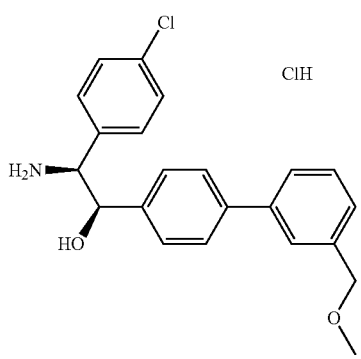 [SMILES: COCc1cccc(-c2ccc([C@@H](O)[C@@H](N)c3ccc(Cl)cc3)cc2)c1 ; Cl]

To as solution of rac-erythro-2-amino-2-(4-chloro-phenyl)-1-(4-iodo-phenyl)-ethanol (Intermediate 33) (31 mg) in THF (3.1 ml) and water (0.75 ml) was added 3-methoxymethylphenyl boronic acid (16.5 mg), cesium carbonate (108 mg) and tetrakis(triphenylphosphine)palladium (2.6 mg). The reaction mixture was then stirred for 4 hours at 80° C.

To the reaction mixture was then added a mixture of water and ethanol (c.a. 1:1) and charcoal which was then filtrated off. The filtrate was then collected and the organic phase was evaporated in vacuo and to the remaining gummy solution was then filtrated again and the isolated gum/solid was isolated by dissolving it in ethanol. The latter solution was then treated with 0.2 ml of HCl saturated solution in ethanol and then evaporation yielded the title compound as a light brown solid (9.3 mg, 27%) which was used without further purification: MS (ISP): 374.1 $(M+H)^+$ (85%).

Example 61 rac-erythro-2-Amino-2-(4-chloro-phenyl)-1-(4-pyridin-4-yl-phenyl)-ethanol

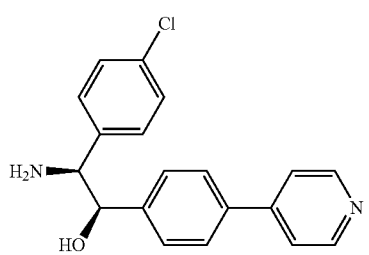 [SMILES: N[C@@H](c1ccc(Cl)cc1)[C@H](O)c1ccc(-c2ccncc2)cc1]

To as solution of rac-erythro-2-amino-2-(4-chloro-phenyl)-1-(4-iodo-phenyl)-ethanol (Intermediate 33) (27.2 mg) in THF (3.1 ml) and water (0.75 ml) was added 4-pyridine boronic acid (10.7 mg), cesium carbonate (95 mg) and tetrakis(triphenylphosphine)-palladium (2.3 mg). The reaction mixture was then stirred for 50 hours at 80° C. To the reaction mixture was then added a mixture of water and ethanol (c.a. 1:1) and charcoal which was then filtrated off. The filtrate was then collected and the organic phase was slowly evaporated in vacuo and the precipitate was then isolated by filtration and washed with water to yield the title compound as an off white solid (16.0 mg, 67%) which was used without further purification. MS (ISP): 325.1 $(M+H)^+$ (55%).

Example 62 rac-erythro-2-Amino-2-(4-chloro-phenyl)-1-(3'-methanesulfonyl-biphenyl-4-yl)-ethanol

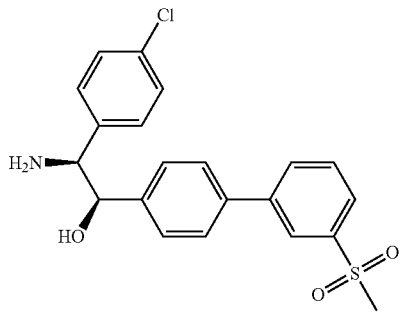 [SMILES: CS(=O)(=O)c1cccc(-c2ccc([C@@H](O)[C@@H](N)c3ccc(Cl)cc3)cc2)c1]

The title compound was prepared from rac-erythro-2-amino-2-(4-chloro-phenyl)-1-(4-iodo-phenyl)-ethanol (Intermediate 33) and 3-methylsulfonylboronic acid in analogy to Example 61: MS (ISP): 402.0 $(M+H)^+$ (35%).

Example 63 rac-erythro-2-Amino-2-(4-chloro-phenyl)-1-(4-pyridin-3-yl-phenyl)-ethanol hydrochloride

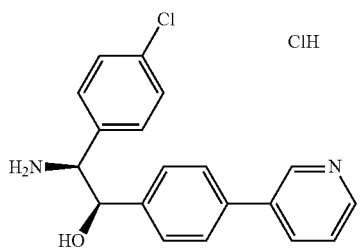 [SMILES: N[C@@H](c1ccc(Cl)cc1)[C@H](O)c1ccc(-c2cccnc2)cc1 ; Cl]

rac-erythro-2-Amino-2-(4-chloro-phenyl)-1-(4-pyridin-3-yl-phenyl)-ethanol was prepared in a similar manner to Example 61 using 3-pyridine boronic acid instead of 4-pyridine boronic acid. The title compound was formed by dissolving the compound in dichloromethane and adding 0.1M HCl methanolic solution to form the corresponding salt. The solution was then concentrated and dried under high vacuum at 60° C. to yield the title compound: MS (ISP): 325.2 $(M+H)^+$ (62%).

Example 64 rac-erythro-2-Amino-2-(4-chloro-phenyl)-1-[4-(5-methoxy-pyridin-3-yl)-phenyl]-ethanol

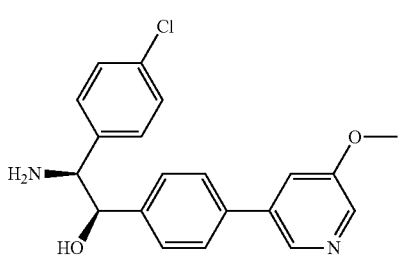 [SMILES: COc1cncc(-c2ccc([C@@H](O)[C@@H](N)c3ccc(Cl)cc3)cc2)c1]

The title compound was prepared in a similar manner to Example 61 using 3-methoxy-5-(4,4,5,5-tetramethyl-[1,3,2]dioxaborolan-2-yl)-pyridine instead of 4-pyridine boronic acid: MS (ISP): 355.3 $(M+H)^+$ (48%).

Example 65 rac-erythro-2-Amino-2-(4-chloro-phenyl)-1-(4-pyrimidin-5-yl-phenyl)-ethanol

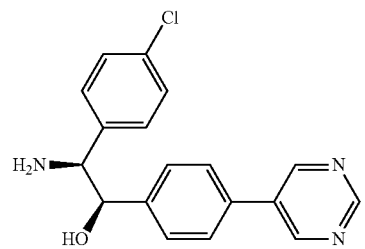 [SMILES: N[C@@H](c1ccc(Cl)cc1)[C@H](O)c1ccc(-c2cncnc2)cc1]

The title compound was prepared in a similar manner to Example 61 using pyrimidine-5-boronic acid instead of 4-pyridine boronic acid: MS (ISP): 326.1 (M+H)$^+$.

Example 66 rac-erythro-2-Amino-2-(4-chloro-phenyl)-1-[4-(5-fluoro-pyridin-3-yl)-phenyl]-ethanol

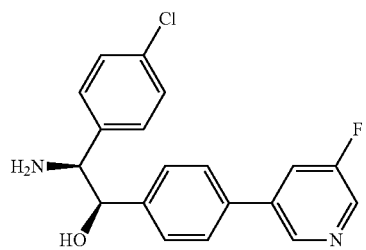 [SMILES: N[C@@H](c1ccc(Cl)cc1)[C@H](O)c1ccc(-c2cncc(F)c2)cc1]

The title compound was prepared in a similar manner to Example 61 using 3-fluoro-5-(4,4,5,5-tetramethyl-[1,3,2]dioxaborolan-2-yl)-pyridine instead of 4-pyridine boronic acid: MS (ISP): 343.1 (M+H)$^+$.

Example 67 rac-erythro-N-[4'-[2-Amino-2-(4-chloro-phenyl)-1-hydroxy-ethyl]-biphenyl-3-yl]-acetamide

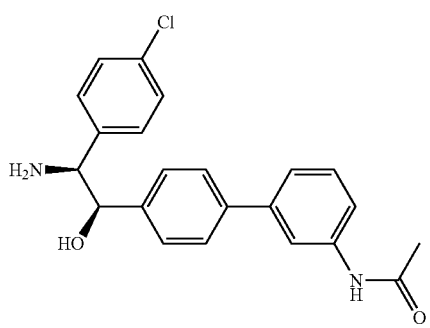 [SMILES: CC(=O)Nc1cccc(-c2ccc([C@@H](O)[C@@H](N)c3ccc(Cl)cc3)cc2)c1]

The title compound was prepared in a similar manner to Example 61 using 3-acetamidobenzeneboronic acid instead of 4-pyridine boronic acid: MS (ISP): 381.2 (M+H)$^+$.

Example 68 rac-erythro-2-Amino-2-(4-chloro-phenyl)-1-(2'-fluoro-biphenyl-4-yl)-ethanol

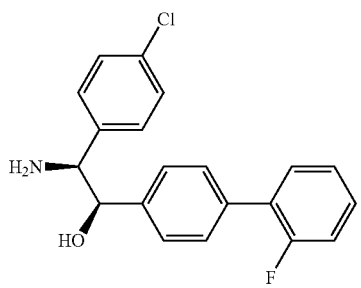 [SMILES: N[C@@H](c1ccc(Cl)cc1)[C@H](O)c1ccc(-c2ccccc2F)cc1]

The title compound was prepared in a similar manner to Example 61 using 2-fluorophenyl boronic acid instead of 4-pyridine boronic acid: MS (ISP): 342.2 (M+H)$^+$.

Example 69 rac-erythro-2-Amino-1-[4-(6-amino-pyridin-3-yl)-phenyl]-2-(4-chloro-phenyl)-ethanol

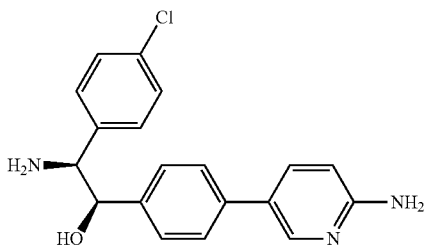 [SMILES: Nc1ccc(-c2ccc([C@@H](O)[C@@H](N)c3ccc(Cl)cc3)cc2)cn1]

The title compound was prepared in a similar manner to Example 61 using 5-(4,4,5,5-tetramethyl-[1,3,2]dioxaborolan-2-yl)-pyridin-2-ylamine instead of 4-pyridine boronic acid: MS (ISP): 340.2 (M+H)$^+$.

Example 70 rac-erythro-2-Amino-2-(4-chloro-phenyl)-1-(4-thiophen-3-yl-phenyl)-ethanol

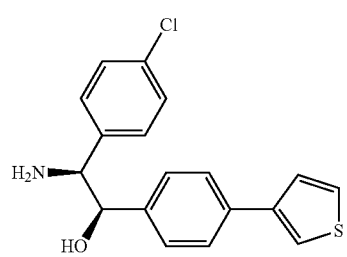 [SMILES: N[C@@H](c1ccc(Cl)cc1)[C@H](O)c1ccc(-c2ccsc2)cc1]

The title compound was prepared in a similar manner to Example 61 using thiophene-3-boronic acid instead of 4-pyridine boronic acid: MS (ISP): 330.1 (M+H)$^+$.

Example 71 rac-erythro-2-Amino-2-(4-chloro-phenyl)-1-(3'-methyl-biphenyl-4-yl)-ethanol

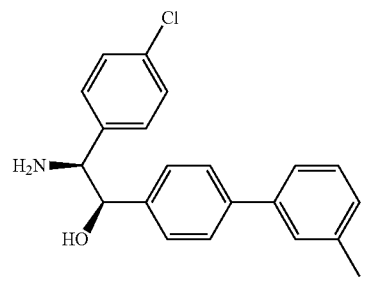 [SMILES: Cc1cccc(-c2ccc([C@@H](O)[C@@H](N)c3ccc(Cl)cc3)cc2)c1]

The title compound was prepared in a similar manner to Example 61 using 3-methylphenyl boronic acid instead of 4-pyridine boronic acid: MS (ISP): 338.2 (M+H)$^+$.

Example 72 rac-erythro-2-Amino-2-(4-chloro-phenyl)-1-(3'-methoxy-biphenyl-4-yl)-ethanol

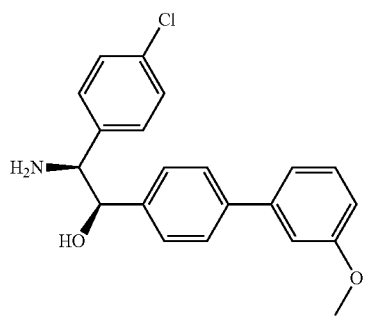 [SMILES: COc1cccc(-c2ccc([C@@H](O)[C@@H](N)c3ccc(Cl)cc3)cc2)c1]

The title compound was prepared in a similar manner to Example 61 using 3-methoxyphenyl boronic acid instead of 4-pyridine boronic acid: MS (ISP): 354.2 (M+H)$^+$ (64%).

Example 73 rac-erythro-2-Amino-1-(2'-chloro-biphenyl-4-yl)-2-(4-chloro-phenyl)-ethanol

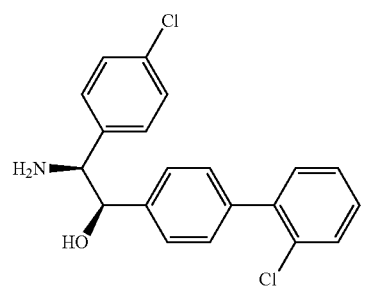 [SMILES: N[C@@H](c1ccc(Cl)cc1)[C@H](O)c1ccc(-c2ccccc2Cl)cc1]

The title compound was prepared in a similar manner to Example 61 using 2-chlorophenyl boronic acid instead of 4-pyridine boronic acid: MS (ISP): 360.1 (M+H)$^+$.

Example 74 rac-erythro-2-Amino-1-(3'-chloro-biphenyl-4-yl)-2-(4-chloro-phenyl)-ethanol

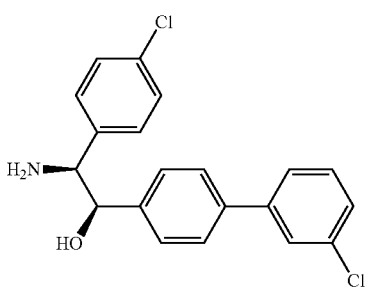 [SMILES: N[C@@H](c1ccc(Cl)cc1)[C@H](O)c1ccc(-c2cccc(Cl)c2)cc1]

The title compound was prepared in a similar manner to Example 61 using 3-chlorophenyl boronic acid instead of 4-pyridine boronic acid: MS (ISP): 360.1 (M+H)$^+$.

Example 75 rac-erythro-2-Amino-2-(4-chloro-phenyl)-1-[4-(2,4-dimethyl-thiazol-5-yl)-phenyl]-ethanol

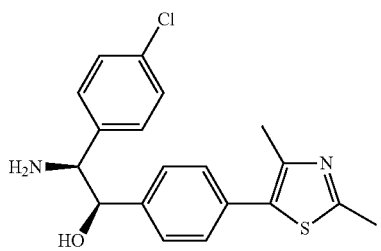 [SMILES: Cc1nc(C)c(-c2ccc([C@@H](O)[C@@H](N)c3ccc(Cl)cc3)cc2)s1]

The title compound was prepared in a similar manner to Example 61 using 2,4-dimethyl-5-(4,4,5,5-tetramethyl-[1,3,2]dioxaborolan-2-yl)-thiazole instead of 4-pyridine boronic acid: MS (ISP): 359.2 (M+H)$^+$ (52%).

Example 76 rac-erythro-2-Amino-2-(4-chloro-phenyl)-1-(2'-methyl-biphenyl-4-yl)-ethanol

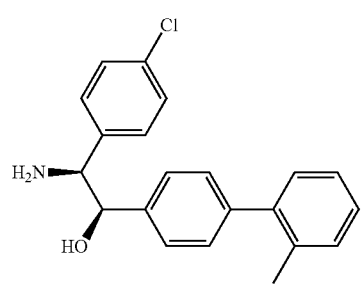 [SMILES: Cc1ccccc1-c1ccc([C@@H](O)[C@@H](N)c2ccc(Cl)cc2)cc1]

The title compound was prepared in a similar manner to Example 61 using o-tolyl boronic acid instead of 4-pyridine boronic acid: MS (ISP): 338.2 (M+H)⁺.

Example 77 rac-erythro-2-Amino-2-(4-chloro-phenyl)-1-[4-(6-methoxy-pyridin-3-yl)-phenyl]-ethanol

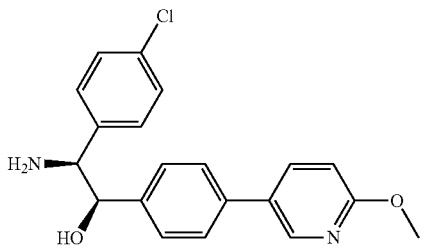 [SMILES: COc1ccc(-c2ccc([C@@H](O)[C@@H](N)c3ccc(Cl)cc3)cc2)cn1]

The title compound was prepared in a similar manner to Example 61 using 2-methoxy-5-pyridineboronic acid instead of 4-pyridine boronic acid: MS (ISP): 355.2 (M+H)⁺ (35%).

Example 78 rac-erythro-2-Amino-2-(4-chloro-phenyl)-1-(3'-trifluoromethoxy-biphenyl-4-yl)-ethanol

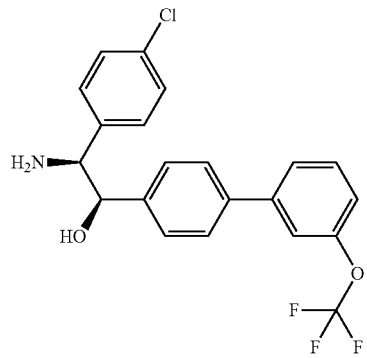 [SMILES: N[C@@H](c1ccc(Cl)cc1)[C@H](O)c1ccc(-c2cccc(OC(F)(F)F)c2)cc1]

The title compound was prepared in a similar manner to Example 61 using 3-(trifluoromethoxy)phenyl boronic acid instead of 4-pyridine boronic acid: MS (ISP): 408.2 (M+H)⁺.

Example 79 rac-erythro-2-Amino-2-(4-chloro-phenyl)-1-(3'-trifluoromethyl-biphenyl-4-yl)-ethanol

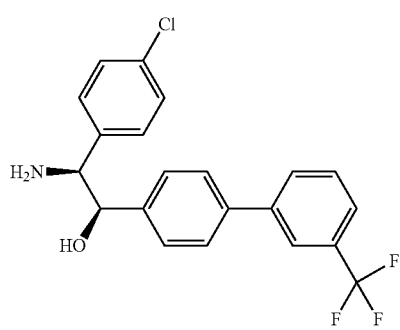 [SMILES: N[C@@H](c1ccc(Cl)cc1)[C@H](O)c1ccc(-c2cccc(C(F)(F)F)c2)cc1]

The title compound was prepared in a similar manner to Example 61 using 3-(trifluoromethyl)phenyl boronic acid instead of 4-pyridine boronic acid: MS (ISP): 392.2 (M+H)⁺.

Example 80 rac-erythro-2-Amino-2-(4-chloro-phenyl)-1-(6-morpholin-4-yl-pyridin-3-yl)-ethanol

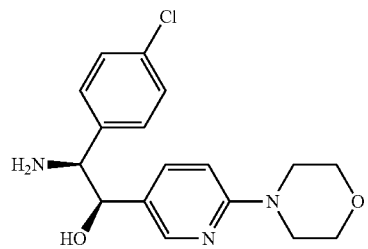 [SMILES: N[C@@H](c1ccc(Cl)cc1)[C@H](O)c1ccc(N2CCOCC2)nc1]

The title compound was prepared in a similar manner to Intermediate 33 using 6-morpholin-4-yl-pyridine-3-carbaldehyde instead of 4-iodo-benzaldehyde: MS (ISP): 334.3 (M+H)⁺.

Example 81 rac-erythro-2-Amino-2-(3,4-dichloro-phenyl)-1-(4-pyridin-3-yl-phenyl)-ethanol

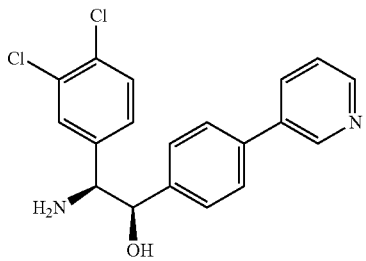 [SMILES: N[C@@H](c1ccc(Cl)c(Cl)c1)[C@H](O)c1ccc(-c2cccnc2)cc1]

a) rac-erythro-2-Amino-2-(3,4-dichloro-phenyl)-1-(4-iodo-phenyl)-ethanol trifluoro-acetate The title compound was prepared from rac-erythro-[1-(3,4-dichloro-phenyl)-2-hydroxy-2-(4-iodo-phenyl)-ethyl]-carbamic acid tert-butyl ester in analogy to Example 1d): MS (ISP): 408.0 and 410.0 (M+H)⁺.

b) rac-erythro-2-Amino-2-(3,4-dichloro-phenyl)-1-(4-pyridin-3-yl-phenyl)-ethanol The title compound was prepared from rac-erythro-[2-amino-2-(3,4-dichloro-phenyl)-1-(4-iodo-phenyl)-ethanol trifluoroacetate and pyridyl-3-boronic acid in analogy to Example 1b): MS (ISP): 359.2 and 361.1 (M+H)⁺.

Example 82 rac-erythro-2-Amino-2-(3,4-dichloro-phenyl)-1-[4-(5-methanesulfonyl-pyridin-3-yl)-phenyl]-ethanol

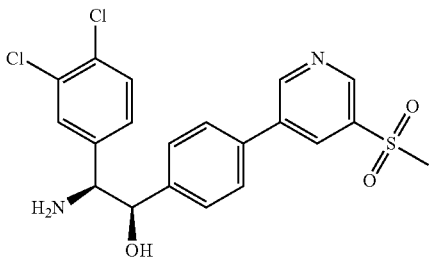 [SMILES: CS(=O)(=O)c1cncc(-c2ccc([C@@H](O)[C@@H](N)c3ccc(Cl)c(Cl)c3)cc2)c1]

The title compound was prepared from rac-erythro-[2-amino-2-(3,4-dichloro-phenyl)-1-(4-iodo-phenyl)-ethanol trifluoroacetate and 5-(methylsulfonyl)-3-pyridineboronic acid in analogy to Example 1b): MS (ISP): 437.1 and 339.0 $(M+H)^+$, 420.0 and 421.9 $((M-NH_3)+H)^+$.

Example 83 rac-erythro-2-Amino-2-(3,4-dichloro-phenyl)-1-[4-(5-fluoro-pyridin-3-yl)-phenyl]-ethanol

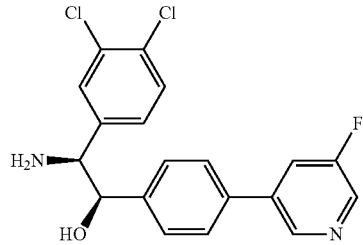 [SMILES: N[C@@H](c1ccc(Cl)c(Cl)c1)[C@H](O)c1ccc(-c2cncc(F)c2)cc1]

The title compound was prepared from rac-erythro-[2-amino-2-(3,4-dichloro-phenyl)-1-(4-iodo-phenyl)-ethanol trifluoroacetate and 5-fluoropyridine-3-boronic acid in analogy to Example 1b): MS (ISP): 377.2 and 379.2 $(M+H)^+$, 360.1 and 362.1 $((M-NH_3)+H)^+$.

Example 84 rac-erythro-2-Amino-2-(3,4-dichloro-phenyl)-1-(4-pyridin-3-yl-phenyl)-ethanol

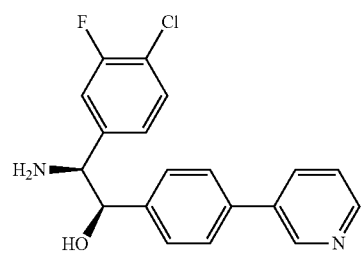 [SMILES: N[C@@H](c1ccc(Cl)c(F)c1)[C@H](O)c1ccc(-c2cccnc2)cc1]

a) rac-[1-(4-Chloro-3-fluoro-phenyl)-2-(4-iodo-phenyl)-2-oxo-ethyl]-carbamic acid tert-butyl ester The title compound was prepared from rac-[(4-chloro-3-fluoro-phenyl)-(methoxy-methyl-carbamoyl)-methyl]-carbamic acid tert-butyl ester (Intermediate 1) and 1,4-di-iodo-benzene in analogy to Example 1a): MS (ISN): 487.9 $(M-H)^-$ and 413.9 $((M-tBuOH)-H)^-$.

b) rac-erythro-[2-Amino-2-(4-chloro-3-fluoro-phenyl)-1-(4-iodo-phenyl)-ethanol tri-fluoroacetate The title compound was prepared from rac-[1-(4-chloro-3-fluoro-phenyl)-2-(4-iodo-phenyl)-2-oxo-ethyl]-carbamic acid tert-butyl ester in analogy to Example 1d): MS (ISP): 392.0 $(M+H)^+$, 375.0 $((M-NH_3)+H)^+$.

c) rac-erythro-2-Amino-2-(3,4-dichloro-phenyl)-1-(4-pyridin-3-yl-phenyl)-ethanol The title compound was prepared from rac-erythro-[2-amino-2-(4-chloro-3-fluoro-phenyl)-1-(4-iodo-phenyl)-ethanol trifluoroacetate and pyridyl-3-boronic acid in analogy to Example 1b): MS (ISP): 343.2 $(M+H)^+$, 326.1 $((M-NH_3)+H)^+$.

Example 85 rac-erythro-2-Amino-2-(4-chloro-3-fluoro-phenyl)-1-[4-(5-fluoro-pyridin-3-yl)-phenyl]-ethanol

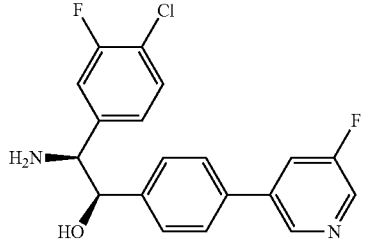 [SMILES: N[C@@H](c1ccc(Cl)c(F)c1)[C@H](O)c1ccc(-c2cncc(F)c2)cc1]

a) rac-erythro-[1-(4-Chloro-3-fluoro-phenyl)-2-hydroxy-2-(4-iodo-phenyl)-ethyl]-carbamic acid tert-butyl ester The title compound was prepared from rac-[1-(4-chloro-3-fluoro-phenyl)-2-(4-iodo-phenyl)-2-oxo-ethyl]-carbamic acid tert-butyl ester in analogy to Example 1c): MS (ISN): 489.9 $(M-H)^-$ and 419.0 $((M-tBuOH)-H)^-$.

b) rac-erythro-[2-Amino-2-(4-chloro-3-fluoro-phenyl)-1-(4-iodo-phenyl)-ethanol trifluoroacetate The title compound was prepared from rac-erythro-[1-(4-chloro-3-fluoro-phenyl)-2-hydroxy-2-(4-iodo-phenyl)-ethyl]-carbamic acid tert-butyl ester in analogy to Example 1d): MS (ISP): 392.0 $(M+H)^+$, 375.0 $((M-NH_3)+H)^+$.

c) rac-erythro-2-Amino-2-(4-chloro-3-fluoro-phenyl)-1-[4-(5-fluoro-pyridin-3-yl)-phenyl]-ethanol The title compound was prepared from rac-erythro-[2-amino-2-(4-chloro-3-fluoro-phenyl)-1-(4-iodo-phenyl)-ethanol trifluoroacetate and 5-fluoropyridine-3-boronic acid in analogy to Example 1b): MS (ISP): 361.0 $(M+H)^+$, 344.0 $((M-NH_3)+H)^+$.

Example 86 rac-erythro-2-Amino-2-(4-chloro-3-methyl-phenyl)-1-(4-pyridin-3-yl-phenyl)-ethanol

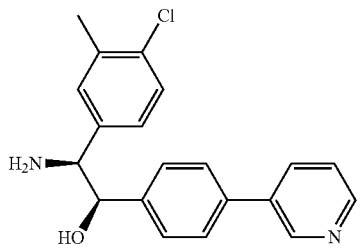

a) rac-[1-(4-Chloro-3-methyl-phenyl)-2-(4-iodo-phenyl)-2-oxo-ethyl]-carbamic acid tert-butyl ester The title compound was prepared from rac-[(4-chloro-3-methyl-phenyl)-(methoxy-methyl-carbamoyl)-methyl]-carbamic acid tert-butyl ester (Intermediate 2) and 1,4-di-iodo-benzene in analogy to Example 1a): MS (ISN): 484.1 (M−H)⁻.

b) rac-erythro-[1-(4-Chloro-3-methyl-phenyl)-2-hydroxy-2-(4-iodo-phenyl)-ethyl]-carbamic acid tert-butyl ester The title compound was prepared from rac-[1-(4-chloro-3-methyl-phenyl)-2-(4-iodo-phenyl)-2-oxo-ethyl]-carbamic acid tert-butyl ester in analogy to Example 1c): MS (ISN): 546.1 (M+AcO)⁻ (100%).

c) rac-erythro-2-Amino-2-(4-chloro-3-methyl-phenyl)-1-(4-iodo-phenyl)-ethanol trifluoroacetate The title compound was prepared from rac-erythro-[1-(4-chloro-3-methyl-phenyl)-2-hydroxy-2-(4-iodo-phenyl)-ethyl]-carbamic acid tert-butyl ester in analogy to Example 1d): MS (ISP): 388.3 (M+H)⁺, 371.0 ((M−NH₃)+H)⁺.

d) rac-erythro-2-Amino-2-(4-chloro-3-methyl-phenyl)-1-(4-pyridin-3-yl-phenyl)-ethanol The title compound was prepared from rac-erythro-2-amino-2-(4-chloro-3-methyl-phenyl)-1-(4-iodo-phenyl)-ethanol trifluoroacetate and pyridyl-3-boronic acid in analogy to Example 1b): MS (ISP): 339.1 (M+H)⁺, 322.3 ((M−NH₃)+H)⁺.

Example 87 rac-erythro-2-Amino-1-(4-pyridin-3-yl-phenyl)-2-(4-trifluoromethyl-phenyl)-ethanol

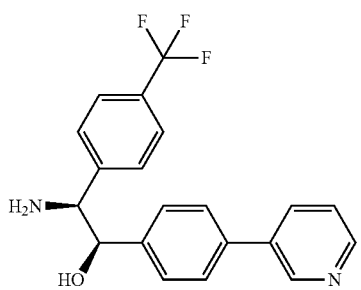 [SMILES: N[C@@H](c1ccc(C(F)(F)F)cc1)[C@H](O)c1ccc(-c2cccnc2)cc1]

a) rac-[2-(4-Iodo-phenyl)-2-oxo-1-(4-trifluoromethyl-phenyl)-ethyl]-carbamic acid tert-butyl ester The title compound was prepared from rac-[(methoxy-methyl-carbamoyl)-(4-trifluoromethyl-phenyl)-methyl]-carbamic acid tert-butyl ester (Intermediate 10) and 1,4-di-iodo-benzene in analogy to Example 1a): MS (ISN): 504.0 (M−H)⁻.

b) rac-erythro-[2-Hydroxy-2-(4-iodo-phenyl)-1-(4-trifluoromethyl-phenyl)-ethyl]-carbamic acid tert-butyl ester The title compound was prepared from rac-[2-(4-iodo-phenyl)-2-oxo-1-(4-trifluoromethyl-phenyl)-ethyl]-carbamic acid tert-butyl ester in analogy to Example 1c): MS (ISN): 505.9 (M−H)⁻ and 432.0 ((M−tBuOH)−H)⁻.

c) rac-erythro-2-Amino-1-(4-iodo-phenyl)-2-(4-trifluoromethyl-phenyl)-ethanol trifluoro acetate The title compound was prepared from rac-erythro-[2-hydroxy-2-(4-iodo-phenyl)-1-(4-trifluoromethyl-phenyl)-ethyl]-carbamic acid tert-butyl ester in analogy to Example 1d): MS (ISP): 408.1 (M+H)⁺, 390.1 ((M−H₂O)+H)⁺.

d) rac-erythro-2-Amino-1-(4-pyridin-3-yl-phenyl)-2-(4-trifluoromethyl-phenyl)-ethanol The title compound was prepared from rac-erythro-2-amino-1-(4-iodo-phenyl)-2-(4-trifluoromethyl-phenyl)-ethanol trifluoroacetate and pyridyl-3-boronic acid in analogy to Example 1b): MS (ISP): 359.2 (M+H)⁺, 342.1 ((M−NH₃)+H)⁺.

Example 89 rac-erythro-2-Amino-2-(3,4-dichloro-phenyl)-1-(3'-dimethylamino-biphenyl-4-yl)-ethanol

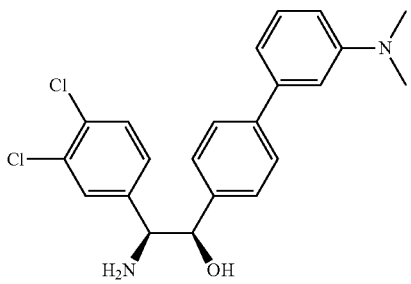 [SMILES: CN(C)c1cccc(-c2ccc([C@@H](O)[C@@H](N)c3ccc(Cl)c(Cl)c3)cc2)c1]

a) rac-[1-(3,4-Dichloro-phenyl)-2-(3'-dimethylamino-biphenyl-4-yl)-2-oxo-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester and 3-(dimethylamino)phenylboronic acid in analogy to Example 1b): MS (ISP): 499.1 and 501.0 (M+H)⁺.

b) rac-2-Amino-2-(3,4-dichloro-phenyl)-1-(3'-dimethylamino-biphenyl-4-yl)-ethanone dihydrochloride The title compound was prepared from rac-[1-(3,4-dichloro-phenyl)-2-(3'-dimethylamino-biphenyl-4-yl)-2-oxo-ethyl]-carbamic acid tert-butyl ester in analogy to Example 38b): MS (ISP): 399.2 and 401.2 (M+H)+.

c) rac-erythro-2-Amino-2-(3,4-dichloro-phenyl)-1-(3'-dimethylamino-biphenyl-4-yl)-ethanol The title compound was prepared from rac-2-amino-2-(3,4-dichloro-phenyl)-1-(3'-dimethylamino-biphenyl-4-yl)-ethanone dihydrochloride in analogy to Example 1c): MS (ISP): 401.1 and 403.4 (M+H)+, 384.0 and 386.0 ((M−NH3)+H)+.

Example 91 rac-erythro-2-Amino-2-(3-fluoro-4-methyl-phenyl)-1-(4-pyridin-3-yl-phenyl)-ethanol

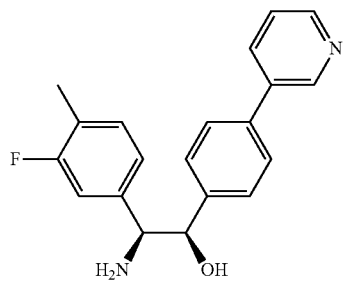 [SMILES: Cc1ccc([C@H](N)[C@H](O)c2ccc(-c3cccnc3)cc2)cc1F]

a) rac-[1-(3-Fluoro-4-methyl-phenyl)-2-(4-iodo-phenyl)-2-oxo-ethyl]-carbamic acid tert-butyl ester The title compound was prepared from rac-[(3-fluoro-4-methyl-phenyl)-(methoxy-methyl-carbamoyl)-methyl]-carbamic acid tert-butyl ester (Intermediate 7) and 1,4-di-iodo-benzene in analogy to Example 1a): MS (ISP): 470.0 (M+H)+.

b) rac-erythro-[1-(3-Fluoro-4-methyl-phenyl)-2-hydroxy-2-(4-iodo-phenyl)-ethyl]-carbamic acid tert-butyl ester The title compound was prepared from rac-[1-(3-fluoro-4-methyl-phenyl)-2-(4-iodo-phenyl)-2-oxo-ethyl]-carbamic acid tert-butyl ester in analogy to Example 1c): MS (ISP): 472.0 (M+H)+.

c) rac-erythro-[1-(3-Fluoro-4-methyl-phenyl)-2-hydroxy-2-(4-pyridin-3-yl-phenyl)-ethyl]-carbamic acid tert-butyl ester The title compound was prepared from rac-erythro-[1-(3-fluoro-4-methyl-phenyl)-2-hydroxy-2-(4-iodo-phenyl)-ethyl]-carbamic acid tert-butyl ester and pyridyl-3-boronic acid in analogy to Example 1b): MS (ISP): 423.2 (M+H)+.

d) rac-erythro-2-Amino-2-(3-fluoro-4-methyl-phenyl)-1-(4-pyridin-3-yl-phenyl)-ethanol The title compound was prepared from rac-erythro-[1-(3-fluoro-4-methyl-phenyl)-2-hydroxy-2-(4-pyridin-3-yl-phenyl)-ethyl]-carbamic acid tert-butyl ester in analogy to Example 1 d): MS (ISP): 323.2 (M+H)+.

Example 92 rac-erythro-2-Amino-2-(3-chloro-4-methyl-phenyl)-1-(4-pyridin-3-yl-phenyl)-ethanol

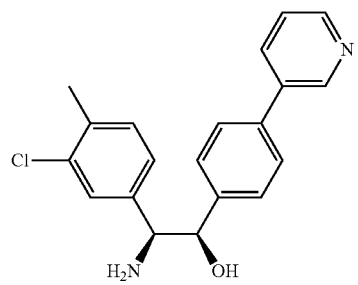 [SMILES: Cc1ccc([C@H](N)[C@H](O)c2ccc(-c3cccnc3)cc2)cc1Cl]

a) rac-[1-(3-Chloro-4-methyl-phenyl)-2-(4-iodo-phenyl)-2-oxo-ethyl]-carbamic acid tert-butyl ester The title compound was prepared from rac-[(3-chloro-4-methyl-phenyl)-(methoxy-methyl-carbamoyl)-methyl]-carbamic acid tert-butyl ester (Intermediate 4) and 1,4-di-iodo-benzene in analogy to Example 1a): MS (ISN): 484.2 (M−H)−.

b) rac-erythro-[1-(3-Chloro-4-methyl-phenyl)-2-hydroxy-2-(4-iodo-phenyl)-ethyl]-carbamic acid tert-butyl ester The title compound was prepared from rac-[1-(3-chloro-4-methyl-phenyl)-2-(4-iodo-phenyl)-2-oxo-ethyl]-carbamic acid tert-butyl ester in analogy to Example 1c): MS (ISP): 488.1 (M+H)+.

c) rac-erythro-[1-(3-Chloro-4-methyl-phenyl)-2-hydroxy-2-(4-pyridin-3-yl-phenyl)-ethyl]-carbamic acid tert-butyl ester The title compound was prepared from rac-erythro-[1-(3-chloro-4-methyl-phenyl)-2-hydroxy-2-(4-iodo-phenyl)-ethyl]-carbamic acid tert-butyl ester and pyridyl-3-boronic acid in analogy to Example 1b): MS (ISP): 439.2 (M+H)+.

d) rac-erythro-2-Amino-2-(3-chloro-4-methyl-phenyl)-1-(4-pyridin-3-yl-phenyl)-ethanol The title compound was prepared from rac-erythro-[1-(3-chloro-4-methyl-phenyl)-2-hydroxy-2-(4-pyridin-3-yl-phenyl)-ethyl]-carbamic acid tert-butyl ester in analogy to Example 1 d): MS (ISP): 339.1 (M+H)+.

Example 93 rac-erythro-2-Amino-2-(3-chloro-4-methyl-phenyl)-1-[4-(5-fluoro-pyridin-3-yl)-phenyl]-ethanol

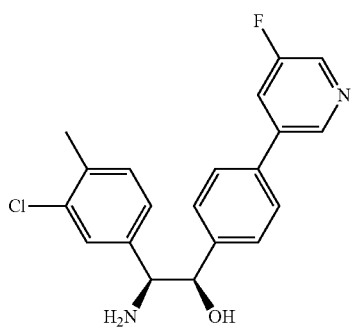 [SMILES: Cc1ccc([C@H](N)[C@H](O)c2ccc(-c3cncc(F)c3)cc2)cc1Cl]

a) rac-erythro-[1-(3-Chloro-4-methyl-phenyl)-2-[4-(5-fluoro-pyridin-3-yl)-phenyl]-2-hydroxy-ethyl]-carbamic acid tert-butyl ester The title compound was prepared from rac-erythro-[1-(3-chloro-4-methyl-phenyl)-2-hydroxy-2-(4-iodo-phenyl)-ethyl]-carbamic acid tert-butyl ester and 5-fluoropyridine-3-boronic acid in analogy to Example 1b): MS (ISP): 457.3 (M+H)$^+$.

b) rac-erythro-2-Amino-2-(3-chloro-4-methyl-phenyl)-1-[4-(5-fluoro-pyridin-3-yl)-phenyl]-ethanol The title compound was prepared from rac-erythro-[1-(3-chloro-4-methyl-phenyl)-2-[4-(5-fluoro-pyridin-3-yl)-phenyl]-2-hydroxy-ethyl]-carbamic acid tert-butyl ester in analogy to Example 1d): MS (ISP): 357.1 (M+H)$^+$.

Example 94 rac-erythro-2-Amino-2-(3-fluoro-4-methyl-phenyl)-1-[4-(5-fluoro-pyridin-3-yl)-phenyl]-ethanol

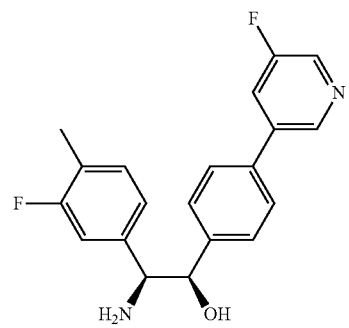 [SMILES: Cc1ccc([C@H](N)[C@H](O)c2ccc(-c3cncc(F)c3)cc2)cc1F]

a) rac-erythro-[1-(3-Fluoro-4-methyl-phenyl)-2-[4-(5-fluoro-pyridin-3-yl)-phenyl]-2-hydroxy-ethyl]-carbamic acid tert-butyl ester The title compound was prepared from rac-erythro-[1-(3-fluoro-4-methyl-phenyl)-2-hydroxy-2-(4-iodo-phenyl)-ethyl]-carbamic acid tert-butyl ester and 5-fluoropyridine-3-boronic acid in analogy to Example 1b): MS (ISP): 441.2 (M+H)$^+$.

b) rac-erythro-2-Amino-2-(3-fluoro-4-methyl-phenyl)-1-[4-(5-fluoro-pyridin-3-yl)-phenyl]-ethanol The title compound was prepared from rac-erythro-[1-(3-fluoro-4-methyl-phenyl)-2-[4-(5-fluoro-pyridin-3-yl)-phenyl]-2-hydroxy-ethyl]-carbamic acid tert-butyl ester in analogy to Example 1d): MS (ISP): 341.1 (M+H)$^+$.

Example 95 rac-erythro-2-Amino-2-(3-fluoro-4-trifluoromethyl-phenyl)-1-(4-pyridin-3-yl-phenyl)-ethanol

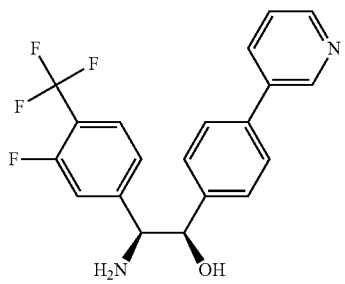 [SMILES: N[C@@H](c1ccc(C(F)(F)F)c(F)c1)[C@H](O)c1ccc(-c2cccnc2)cc1]

a) rac-[1-(3-Fluoro-4-trifluoromethyl-phenyl)-2-(4-iodo-phenyl)-2-oxo-ethyl]-carbamic acid tert-butyl ester The title compound was prepared from rac-[(3-fluoro-4-trifluoromethyl-phenyl)-(methoxy-methyl-carbamoyl)-methyl]-carbamic acid tert-butyl ester (Intermediate 5) and 1,4-di-iodobenzene in analogy to Example 1a): MS (ISN): 522.1 (M−H)$^-$.

b) rac-erythro-[1-(3-Fluoro-4-trifluoromethyl-phenyl)-2-hydroxy-2-(4-iodo-phenyl)-ethyl]-carbamic acid tert-butyl ester The title compound was prepared from rac-[1-(3-fluoro-4-trifluoromethyl-phenyl)-2-(4-iodo-phenyl)-2-oxo-ethyl]-carbamic acid tert-butyl ester in analogy to Example 1c): MS (ISN): 524.1 (M−H)$^-$.

c) rac-erythro-[1-(3-Fluoro-4-trifluoromethyl-phenyl)-2-hydroxy-2-(4-pyridin-3-yl-phenyl)-ethyl]-carbamic acid tert-butyl ester The title compound was prepared from rac-erythro-[1-(3-fluoro-4-trifluoromethyl-phenyl)-2-hydroxy-2-(4-iodo-phenyl)-ethyl]-carbamic acid tert-butyl ester and pyridyl-3-boronic acid in analogy to Example 1b): MS (ISP): 477.2 (M+H)$^+$.

d) rac-erythro-2-Amino-2-(3-fluoro-4-trifluoromethyl-phenyl)-1-(4-pyridin-3-yl-phenyl)-ethanol The title compound was prepared from rac-erythro-[1-(3-fluoro-4-trifluoromethyl-phenyl)-2-hydroxy-2-(4-pyridin-3-yl-phenyl)-ethyl]-carbamic acid tert-butyl ester in analogy to Example 1d): MS (ISP): 377.3 (M+H)$^+$.

Example 96 rac-erythro-2-Amino-1-[4-(5-fluoro-pyridin-3-yl)-phenyl]-2-(3-fluoro-4-trifluoromethyl-phenyl)-ethanol

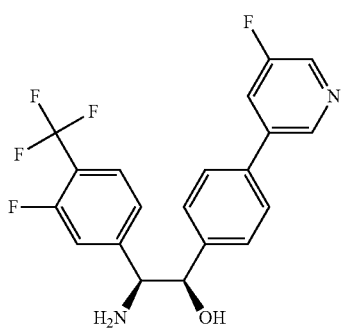 [SMILES: N[C@@H](c1ccc(C(F)(F)F)c(F)c1)[C@H](O)c1ccc(-c2cncc(F)c2)cc1]

a) rac-erythro-[2-[4-(5-Fluoro-pyridin-3-yl)-phenyl]-1-(3-fluoro-4-trifluoromethyl-phenyl)-2-hydroxy-ethyl]-carbamic acid tert-butyl ester The title compound was prepared from rac-erythro-[1-(3-fluoro-4-trifluoromethyl-phenyl)-2-hydroxy-2-(4-iodo-phenyl)-ethyl]-carbamic acid tert-butyl ester and 5-fluoropyridine-3-boronic acid in analogy to Example 1b): MS (ISN): 493.2 (M−H)$^-$.

b) rac-erythro-2-Amino-1-[4-(5-fluoro-pyridin-3-yl)-phenyl]-2-(3-fluoro-4-trifluoro-methyl-phenyl)-ethanol The title compound was prepared from rac-erythro-[2-[4-(5-fluoro-pyridin-3-yl)-phenyl]-1-(3-fluoro-4-trifluoromethyl-phenyl)-2-hydroxy-ethyl]-carbamic acid tert-butyl ester in analogy to Example 1d): MS (ISP): 395.0 (M+H)$^+$.

Example 97 rac-erythro-2-Amino-2-(4-chloro-2-fluoro-phenyl)-1-(4-pyridin-3-yl-phenyl)-ethanol

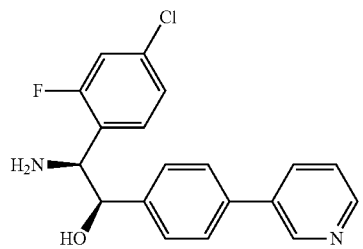 [SMILES: N[C@@H](c1ccc(Cl)cc1F)[C@H](O)c1ccc(-c2cccnc2)cc1]

a) rac-[1-(4-Chloro-2-fluoro-phenyl)-2-(4-iodo-phenyl)-2-oxo-ethyl]-carbamic acid tert-butyl ester The title compound was prepared from rac-[(4-chloro-2-fluoro-phenyl)-(methoxy-methyl-carbamoyl)-methyl]-carbamic acid tert-butyl ester (Intermediate 3) and 1,4-di-iodo-benzene in analogy to Example 1a): MS (ISP): 489.9 (M+H)$^+$.

b) rac-erythro-[1-(4-Chloro-2-fluoro-phenyl)-2-hydroxy-2-(4-iodo-phenyl)-ethyl]-carbamic acid tert-butyl ester The title compound was prepared from rac-[1-(4-chloro-2-fluoro-phenyl)-2-(4-iodo-phenyl)-2-oxo-ethyl]-carbamic acid tert-butyl ester in analogy to Example 1c): (ISP): 491.9 (M+H)$^+$.

c) rac-erythro-[2-Amino-2-(4-chloro-2-fluoro-phenyl)-1-(4-iodo-phenyl)-ethanol trifluoroacetate The title compound was prepared from rac-erythro-[1-(4-chloro-2-fluoro-phenyl)-2-hydroxy-2-(4-iodo-phenyl)-ethyl]-carbamic acid tert-butyl ester in analogy to Example 1d): MS (ISP): 392.0 (M+H)$^+$.

d) rac-erythro-2-Amino-2-(4-chloro-2-fluoro-phenyl)-1-(4-pyridin-3-yl-phenyl)-ethanol The title compound was prepared from rac-erythro-[2-amino-2-(4-chloro-2-fluoro-phenyl)-1-(4-iodo-phenyl)-ethanol trifluoroacetate and pyridyl-3-boronic acid in analogy to Example 1b): MS (ISP): 343.2 (M+H)$^+$.

Example 98 rac-erythro-1-(3,4-Dichloro-phenyl)-2-methoxy-2-(4-pyridin-3-yl-phenyl)-ethylamine dihydrochloride

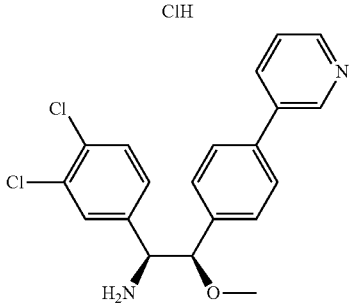 [SMILES: Cl ; CO[C@H](c1ccc(-c2cccnc2)cc1)[C@@H](N)c1ccc(Cl)c(Cl)c1]

a) rac-erythro-[1-(3,4-Dichloro-phenyl)-2-(4-iodo-phenyl)-2-methoxy-ethyl]-carbamic acid tert-butyl ester To a solution of 200 mg (0.694 mmol) rac-erythro-[1-(3,4-dichloro-phenyl)-2-hydroxy-2-(4-iodo-phenyl)-ethyl]-carbamic acid tert-butyl ester in 4 ml dry tetrahydrofuran were added 17 mg (0.414 mmol) sodium hydride and the mixture stirred at ambient temperature for 5 min. Then 246 ul iodomethane were added and stirring continued for 2 hours. The reaction mixture was evaporated and the residue purified by flash-chromatography on silica gel with a heptane/ethyl acetate gradient with 0 to 30% ethyl acetate. The title compound was obtained as colorless solid: MS (ISP): 521.9 and 523.8 (M+H)⁺.

b) rac-erythro-[1-(3,4-Dichloro-phenyl)-2-(4-iodo-phenyl)-2-methoxy-ethylamine trifluoroacetate The title compound was prepared from rac-erythro-[1-(3,4-dichloro-phenyl)-2-(4-iodo-phenyl)-2-methoxy-ethyl]-carbamic acid tert-butyl ester in analogy to Example 1d): MS (ISP): 421.9 and 423.9 (M+H)⁺, 405.1 and 407.0 ((M–NH₃)+H)⁺.

c) rac-erythro-1-(3,4-Dichloro-phenyl)-2-methoxy-2-(4-pyridin-3-yl-phenyl)-ethylamine dihydrochloride The title compound was prepared from rac-erythro-[2-amino-2-(4-chloro-2-fluoro-phenyl)-1-(4-iodo-phenyl)-ethanol trifluoroacetate and pyridyl-3-boronic acid in analogy to Example 1b). The compound was isolated as dihydrochloride: MS (ISP): 373.2 and 375.2 (M+H)⁺, 356.0 and 358.2 ((M–NH₃)+H)⁺.

Example 99 rac-erythro-[1-(3,4-Dichloro-phenyl)-2-ethoxy-2-[4-(5-fluoro-pyridin-3-yl)-phenyl]-ethylamine trifluoroacetate

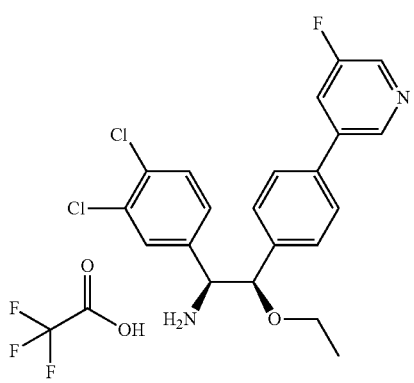

a) rac-erythro-[1-(3,4-Dichloro-phenyl)-2-[4-(5-fluoro-pyridin-3-yl)-phenyl]-2-hydroxy-ethyl]-carbamic acid tert-butyl ester The title compound was prepared from rac-erythro-[1-(3,4-dichloro-phenyl)-2-hydroxy-2-(4-iodo-phenyl)-ethyl]-carbamic acid tert-butyl ester and 5-fluoropyridine-3-boronic acid in analogy to Example 1b): MS (ISP): 477.0 and 479.1 (M+H)⁺.

b) rac-erythro-[1-(3,4-Dichloro-phenyl)-2-ethoxy-2-[4-(5-fluoro-pyridin-3-yl)-phenyl]-ethyl]-carbamic acid tert-butyl ester The title compound was prepared from rac-erythro-[1-(3,4-dichloro-phenyl)-2-[4-(5-fluoro-pyridin-3-yl)-phenyl]-2-hydroxy-ethyl]-carbamic acid tert-butyl ester and ethyl iodide in analogy to Example 98a): MS (ISP): 505.1 and 507.0 (M+H)⁺.

c) rac-erythro-[1-(3,4-Dichloro-phenyl)-2-ethoxy-2-[4-(5-fluoro-pyridin-3-yl)-phenyl]-ethylamine trifluoroacetate The title compound was prepared from rac-erythro-[1-(3,4-dichloro-phenyl)-2-ethoxy-2-[4-(5-fluoro-pyridin-3-yl)-phenyl]-ethyl]-carbamic acid tert-butyl ester in analogy to Example 1d): MS (ISP): 405.3 and 407.1 (M+H)⁺, 388.1 and 390.1 ((M–NH₃)+H)⁺.

Example 100 rac-erythro-2-Amino-2-(3,4-dichloro-phenyl)-1-(4-phenoxy-phenyl)-ethanol

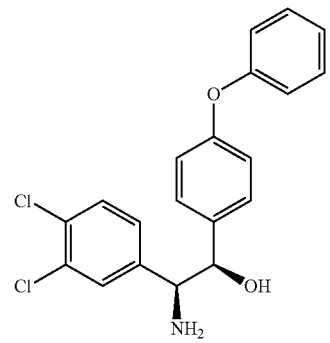 [SMILES: N[C@@H](c1ccc(Cl)c(Cl)c1)[C@H](O)c1ccc(Oc2ccccc2)cc1]

a) rac-[1-(3,4-Dichloro-phenyl)-2-oxo-2-(4-phenoxy-phenyl)-ethyl]-carbamic acid tert-butyl ester The title compound was prepared from rac-[(3,4-dichloro-phenyl)-(methoxy-methyl-carbamoyl)-methyl]-carbamic acid tert-butyl ester (Intermediate 9) and 1-bromo-4-phenoxy-benzene in analogy to Example 1a): MS (ISP): 472.0 (M+H)⁺.

b) rac-erythro-2-Amino-2-(3,4-dichloro-phenyl)-1-(4-phenoxy-phenyl)-ethanone hydrochloride The title compound was prepared from rac-[1-(3,4-dichloro-phenyl)-2-oxo-2-(4-phenoxy-phenyl)-ethyl]-carbamic acid tert-butyl ester in analogy to Example 38b): MS (ISP): 372.0 and 374.1 (M+H)⁺.

c) rac-erythro-2-Amino-2-(3,4-dichloro-phenyl)-1-(4-phenoxy-phenyl)-ethanol

The title compound was prepared from rac-erythro-2-amino-2-(3,4-dichloro-phenyl)-1-(4-phenoxy-phenyl)-ethanone hydrochloride in analogy to Example 1c): MS (ISP): 374.1 and 376.4 (M+H)⁺, 356.1 and 358.2 ((M–H₂O)+H)⁺ (100%).

Example 101 rac-erythro-2-Amino-2-(4-chloro-phenyl)-1-[2-fluoro-4-(2,2,3,3,3-pentafluoro-propoxy)-phenyl]-ethanol

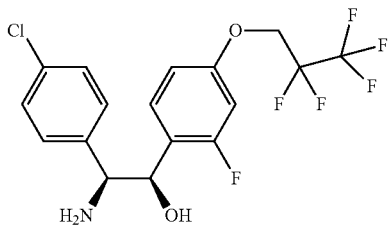 [SMILES: N[C@@H](c1ccc(Cl)cc1)[C@H](O)c1ccc(OCC(F)(F)C(F)(F)F)cc1F]

a) rac-[1-(4-Chloro-phenyl)-2-[2-fluoro-4-(2,2,3,3,3-pentafluoro-propoxy)-phenyl]-2-oxo-ethyl]-carbamic acid tert-butyl ester The title compound was prepared from rac-[(4-chloro-phenyl)-(methoxy-methyl-carbamoyl)-methyl]-carbamic acid tert-butyl ester (Intermediate 8) and 1-bromo-2-fluoro-4-(2,2,3,3,3-pentafluoro-propoxy)-benzene (Intermediate 34) in analogy to Example 1a): MS (ISN): 510.3 (M–H)⁻.

b) rac-erythro-2-Amino-2-(4-chloro-phenyl)-1-[2-fluoro-4-(2,2,3,3,3-pentafluoro-propoxy)-phenyl]-ethanone hydrochloride The title compound was prepared from rac-[1-(4-chloro-phenyl)-2-[2-fluoro-4-(2,2,3,3,3-pentafluoro-propoxy)-phenyl]-2-oxo-ethyl]-carbamic acid tert-butyl ester in analogy to Example 2d): MS (ISP): 412.1 (M+H)⁺.

c) rac-erythro-2-Amino-2-(4-chloro-phenyl)-1-[2-fluoro-4-(2,2,3,3,3-pentafluoro-propoxy)-phenyl]-ethanol The title compound was prepared from rac-erythro-2-amino-2-(3,4-dichloro-phenyl)-1-(4-phenoxy-phenyl)-ethanone hydrochloride in analogy to Example 1c): MS (ISP): 414.2 (M+H)⁺.

Example 102 rac-erythro-2-Amino-2-(4-chloro-phenyl)-1-[4-(2,2,2-trifluoro-1-methyl-ethoxy)-phenyl]-ethanol

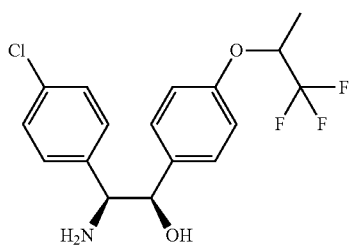 [SMILES: CC(Oc1ccc([C@@H](O)[C@@H](N)c2ccc(Cl)cc2)cc1)C(F)(F)F]

a) rac-[1-(4-Chloro-phenyl)-2-oxo-2-[4-(2,2,2-trifluoro-1-methyl-ethoxy)-phenyl]-ethyl]-carbamic acid tert-butyl ester The title compound was prepared from rac-[(4-chloro-phenyl)-(methoxy-methyl-carbamoyl)-methyl]-carbamic acid tert-butyl ester (Intermediate 8) and rac-1-bromo-4-(2,2,2-trifluoro-1-methyl-ethoxy)-benzene (Intermediate 35) in analogy to Example 1a): MS (ISP): 458.2 (M+H)⁺.

b) rac-erythro-2-Amino-2-(4-chloro-phenyl)-1-[4-(2,2,2-trifluoro-1-methyl-ethoxy)-phenyl]-ethanone hydrochloride The title compound was prepared from rac-[1-(4-chloro-phenyl)-2-oxo-2-[4-(2,2,2-trifluoro-1-methyl-ethoxy)-phenyl]-ethyl]-carbamic acid tert-butyl ester in analogy to Example 2 d): MS (ISP): 358.1 (M+H)⁺.

c) rac-erythro-2-Amino-2-(4-chloro-phenyl)-1-[4-(2,2,2-trifluoro-1-methyl-ethoxy)-phenyl]-ethanol The title compound was prepared from rac-erythro-2-amino-2-(4-chloro-phenyl)-1-[4-(2,2,2-trifluoro-1-methyl-ethoxy)-phenyl]-ethanone hydrochloride in analogy to Example 1c): MS (ISP): 360.1 (M+H)⁺.

Example 103 rac-erythro-2-Amino-2-(3,4-dichloro-phenyl)-1-(3'-nitro-biphenyl-4-yl)-ethanol

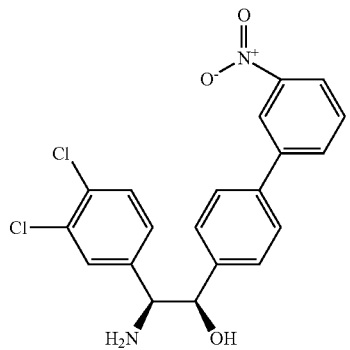 [SMILES: N[C@@H](c1ccc(Cl)c(Cl)c1)[C@H](O)c1ccc(-c2cccc([N+](=O)[O-])c2)cc1]

a) rac-[1-(3,4-Dichloro-phenyl)-2-(3'-nitro-biphenyl-4-yl)-2-oxo-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester and 3-nitrobenzene-boronic acid in analogy to Example 2b): MS (ISN): 499.1 (M–H)⁻.

b) rac-2-Amino-2-(3,4-dichloro-phenyl)-1-(3'-nitro-biphenyl-4-yl)-ethanone hydrochloride The title compound was prepared from rac-[1-(3,4-dichloro-phenyl)-2-(3'-nitro-biphenyl-4-yl)-2-oxo-ethyl]-carbamic acid tert-butyl ester in analogy to Example 38b): MS (ISP): 401.0 and 403.2 (M+H)⁺.

c) rac-erythro-2-Amino-2-(3,4-dichloro-phenyl)-1-(3'-nitro-biphenyl-4-yl)-ethanol The title compound was prepared from rac-2-amino-2-(3,4-dichloro-phenyl)-1-(3'-nitro-biphenyl-4-yl)-ethanone hydrochloride in analogy to Example 1c): MS (ISP): 403.3 and 405.1 (M+H)⁺, 386.0 and 388.1 ((M–NH₃)+H)⁺.

Example 104 rac-erythro-4'-[2-Amino-2-(3,4-dichloro-phenyl)-1-hydroxy-ethyl]-biphenyl-3-carboxylic acid amide

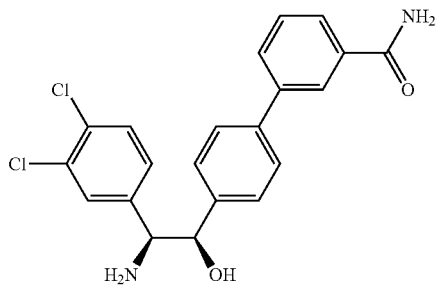 [SMILES: NC(=O)c1cccc(-c2ccc([C@@H](O)[C@@H](N)c3ccc(Cl)c(Cl)c3)cc2)c1]

a) rac-[2-(3'-Carbamoyl-biphenyl-4-yl)-1-(3,4-dichloro-phenyl)-2-oxo-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester and 3-aminocarbonylphenyl-boronic acid in analogy to Example 2b): MS (ISN): 497.2 and 499.2 (M−H)⁻.

b) rac-4'-[2-Amino-2-(3,4-dichloro-phenyl)-acetyl]-biphenyl-3-carboxylic acid amide hydrochloride The title compound was prepared from rac-[2-(3'-carbamoyl-biphenyl-4-yl)-1-(3,4-dichloro-phenyl)-2-oxo-ethyl]-carbamic acid tert-butyl ester in analogy to Example 38b): MS (ISP): 399.1 and 401.0 (M+H)⁺.

c) rac-erythro-4'-[2-Amino-2-(3,4-dichloro-phenyl)-1-hydroxy-ethyl]-biphenyl-3-carboxylic acid amide The title compound was prepared from rac-4'-[2-amino-2-(3,4-dichloro-phenyl)-acetyl]-biphenyl-3-carboxylic acid amide hydrochloride in analogy to Example 1c): MS (ISP): 401.2 and 403.3 (M+H)⁺, 384.1 and 385.9 ((M−NH₃)+H)⁺.

Example 105 rac-erythro-2-Amino-2-(3,4-dichloro-phenyl)-1-(2'-fluoro-5'-isopropoxy-biphenyl-4-yl)-ethanol

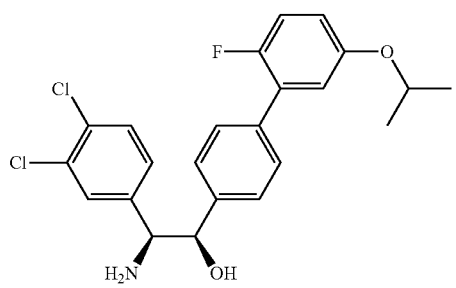 [SMILES: CC(C)Oc1ccc(F)c(-c2ccc([C@@H](O)[C@@H](N)c3ccc(Cl)c(Cl)c3)cc2)c1]

a) rac-[1-(3,4-Dichloro-phenyl)-2-(2'-fluoro-5'-isopropoxy-biphenyl-4-yl)-2-oxo-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester and 2-fluoro-5-isopropoxyphenylboronic acid in analogy to Example 2b): MS (ISP): 532.1 and 534.1 (M+H)⁺, 432.2 and 434.1 ((M−Boc)+H)⁺.

b) rac-2-Amino-2-(3,4-dichloro-phenyl)-1-(2'-fluoro-5'-isopropoxy-biphenyl-4-yl)-ethanone hydrochloride The title compound was prepared from rac-[1-(3,4-dichloro-phenyl)-2-(2'-fluoro-5'-isopropoxy-biphenyl-4-yl)-2-oxo-ethyl]-carbamic acid tert-butyl ester in analogy to Example 38 b): MS (ISN): 430.3 and 432.3 (M−H)⁻.

c) rac-erythro-2-Amino-2-(3,4-dichloro-phenyl)-1-(2'-fluoro-5'-isopropoxy-biphenyl-4-yl)-ethanol The title compound was prepared from rac-2-amino-2-(3,4-dichloro-phenyl)-1-(2'-fluoro-5'-isopropoxy-biphenyl-4-yl)-ethanone hydrochloride in analogy to Example 1c): MS (ISP): 434.2 and 436.1 (M+H)⁺, 417.2 and 418.1 ((M−NH₃)+H)⁺.

Example 106 rac-erythro-2-Amino-2-(3,4-dichloro-phenyl)-1-(3'-isopropoxy-biphenyl-4-yl)-ethanol

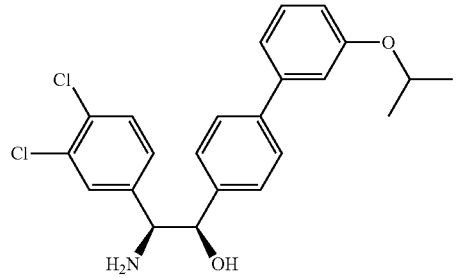 [SMILES: CC(C)Oc1cccc(-c2ccc([C@@H](O)[C@@H](N)c3ccc(Cl)c(Cl)c3)cc2)c1]

a) rac-[1-(3,4-Dichloro-phenyl)-2-(3'-isopropoxy-biphenyl-4-yl)-2-oxo-ethyl]-carbamic acid tert-butyl ester The title compound was prepared from rac-[1-(3,4-dichloro-phenyl)-2-(4-iodo-phenyl)-2-oxo-ethyl]-carbamic acid tert-butyl ester and 3-isopropoxyphenylboronic acid in analogy to Example 2b): MS (ISN): 512.3 and 514.3 (M−H)⁻.

b) rac-2-Amino-2-(3,4-dichloro-phenyl)-1-(3'-isopropoxy-biphenyl-4-yl)-ethanone hydrochloride The title compound was prepared from rac-[1-(3,4-dichloro-phenyl)-2-(3'-isopropoxy-biphenyl-4-yl)-2-oxo-ethyl]-carbamic acid tert-butyl ester in analogy to Example 38b): MS (ISP): 412.2 and 414.4 (M+H)⁺.

c) rac-erythro-2-Amino-2-(3,4-dichloro-phenyl)-1-(3'-isopropoxy-biphenyl-4-yl)-ethanol The title compound was prepared from rac-2-amino-2-(3,4-dichloro-phenyl)-1-(3'-isopropoxy-biphenyl-4-yl)-ethanone hydrochloride in analogy to Example 1c): MS (ISP): 416.1 and 418.2 (M+H)⁺, 399.0 and 401.1 ((M−NH₃)+H)⁺.

Pharmacological Tests

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM Complete Medium:

Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies).

Uptake Buffer (UB):

150 mM NaCl, 10 mM Hepes-Tris, pH 7.4, 1 mM $CaCl_2$, 2.5 mM KCl, 2.5 mM $MgSO_4$, 10 mM (+) D-glucose. Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The prepared compounds show an $IC_{50}$ (µM) at GlyT-1 in the range of 0.006-5.0. The compounds described in examples 1-106 have an $IC_{50}$ data$\leq$1.0 µM. The preferred $IC_{50}$ data (<0.5 µM) for selected examples is be provided in the table below.

TABLE 3

$IC_{50}$ (µM) at GlyT-1 for selected examples

| Ex | $Ic_{50}$ (hglyt1b) |
|---|---|
| 1 | 0.025 |
| 2 | 0.063 |
| 3 | 0.186 |
| 4 | 0.346 |
| 5 | 0.615 |
| 6 | 0.012 |
| 7 | 0.041 |
| 8 | 0.059 |
| 9 | 0.138 |
| 10 | 0.188 |
| 11 | 0.097 |
| 12 | 0.148 |
| 13 | 0.113 |
| 14 | 0.275 |
| 15 | 0.021 |
| 16 | 0.039 |
| 17 | 0.043 |
| 18 | 0.049 |
| 19 | 0.082 |
| 20 | 0.090 |
| 21 | 0.091 |
| 22 | 0.131 |
| 23 | 0.160 |
| 24 | 0.205 |
| 25 | 0.216 |
| 26 | 0.239 |
| 27 | 0.259 |
| 28 | 0.330 |
| 29 | 0.462 |
| 30 | 0.577 |
| 31 | 0.646 |
| 32 | 0.842 |
| 33 | 0.036 |
| 34 | 0.023 |
| 35 | 0.298 |
| 36 | 0.300 |
| 37 | 0.876 |
| 38 | 0.176 |
| 39 | 0.208 |
| 40 | 0.052 |
| 41 | 0.021 |
| 42 | 0.052 |
| 43 | 0.053 |
| 44 | 0.088 |
| 45 | 0.147 |
| 46 | 0.262 |
| 47 | 0.266 |
| 48 | 0.433 |
| 49 | 0.533 |
| 50 | 0.549 |
| 51 | 0.720 |
| 52 | 0.772 |
| 53 | 1.028 |
| 54 | 0.104 |
| 55 | 0.131 |
| 56 | 0.381 |
| 57 | 0.202 |
| 58 | 0.478 |
| 59 | 0.054 |
| 60 | 0.261 |
| 61 | 0.060 |
| 62 | 0.068 |
| 63 | 0.090 |
| 64 | 0.138 |
| 65 | 0.139 |
| 66 | 0.152 |
| 67 | 0.173 |
| 68 | 0.180 |
| 69 | 0.217 |
| 70 | 0.297 |
| 71 | 0.342 |
| 72 | 0.385 |
| 73 | 0.462 |
| 74 | 0.544 |
| 75 | 0.582 |
| 76 | 0.642 |
| 77 | 0.814 |
| 78 | 0.880 |
| 79 | 0.930 |
| 80 | 1.036 |
| 81 | 0.031 |
| 82 | 0.047 |
| 83 | 0.059 |
| 84 | 0.033 |
| 85 | 0.095 |
| 86 | 0.049 |
| 88 | 0.255 |
| 89 | 0.305 |
| 91 | 0.073 |
| 92 | 0.084 |
| 93 | 0.094 |
| 94 | 0.104 |
| 95 | 0.158 |
| 96 | 0.733 |

TABLE 3-continued

IC$_{50}$ (μM) at GlyT-1 for selected examples

| Ex | Ic$_{50}$ (hglyt1b) |
|---|---|
| 97 | 0.267 |
| 98 | 0.388 |
| 99 | 0.285 |
| 100 | 0.323 |
| 101 | 0.334 |
| 102 | 0.384 |
| 103 | 0.412 |
| 104 | 0.056 |
| 105 | 0.567 |
| 106 | 0.851 |

Pharmaceutical Preparations

The compounds of formula I and their pharmaceutically acceptable salts or esters can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The compounds of formula I and their pharmaceutically acceptable salts or esters can be processed with pharmaceutically inert, inorganic or organic carriers for the production of pharmaceutical preparations. Examples are lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like. The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt or ester thereof and a therapeutically inert carrier are also an object of the present invention, as is a process for their production, which comprises bringing one or more compounds of formula I or pharmaceutically acceptable salts or esters thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt or ester thereof. The daily dosage can be administered as single dose or in divided doses and, in addition, the upper limit can also be exceeded when this is found to be indicated.

Pharmaceutical compositions of the invention can be formulated for any route of administration, such as oral, sublingual, buccal, parenteral (subcutaneous, intramuscular, intravenous), rectal, topical, intranasal and trough inhalation or insufflation, and comprise at least one compound of formula I or pharmaceutically active salts or esters thereof, with any pharmaceutically suitable ingredient, excipient, carrier, adjuvant or vehicle. Examples of compositions according to the invention are, but are not limited to:

TABLE 4

Tablet Formulation (Wet Granulation)

| | | mg/tablet | | | |
|---|---|---|---|---|---|
| Item | Ingredients | 5 mg | 25 mg | 100 mg | 500 mg |
| 1 | Compound of formula I | 5 | 25 | 100 | 500 |
| 2 | Lactose Anhydrous DTG | 125 | 105 | 30 | 150 |
| 3 | Sta-Rx 1500 | 6 | 6 | 6 | 30 |
| 4 | Microcrystalline Cellulose | 30 | 30 | 30 | 150 |
| 5 | Magnesium Stearate | 1 | 1 | 1 | 1 |
| | Total | 200 | 200 | 300 | 600 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

TABLE 5

Tablet Formulation (Capsule Formulation)

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

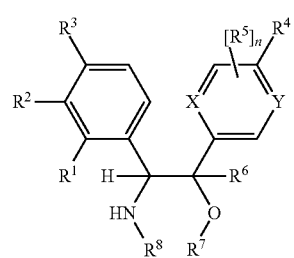

wherein
R$^1$ is hydrogen, halogen or lower alkyl,
R$^2$ is hydrogen, halogen or lower alkyl,
R$^3$ is halogen or lower alkyl, which lower alkyl is optionally substituted by halogen,
R$^4$ is a) lower alkyl, optionally substituted by halogen or lower alkoxy,
  b) lower alkoxy, optionally substituted by halogen, hydroxyl, cycloalkyl or heterocyclyl,
  c) —Si(lower alkyl)$_3$,
  d) —O-cycloalkyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  e) —O-aryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  f) —O-heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  g) —O-heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  wherein each S being part of a heterocyclyl is optionally substituted by oxo,
  h) heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  i) aryl, substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl, or
  j) heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
and R$^4$ is hydrogen when R$^{10}$ is phenyl, wherein the phenyl is optionally substituted by halogen, lower alkyl, or —S(O)$_2$-lower alkyl,
and R$^4$ is aryl when R$^6$ is lower alkyl,
R$^5$ is halogen or lower alkyl,
R$^6$ is hydrogen or lower alkyl,
R$^7$ is hydrogen or lower alkyl,
R$^8$ is hydrogen or lower alkyl,
R$^9$ is hydrogen, halogen, lower alkyl or lower alkoxy,
R$^{10}$ is hydrogen, halogen, lower alkyl or lower alkoxy,
R$^{11}$ is hydrogen or lower alkyl,
R$^{12}$ is hydrogen or lower alkyl,
X is a) N and Y is C—R$^{10}$, or
  b) C—R$^9$ and Y is N,
n is 0 or 1,
with the proviso that R$^8$ is lower alkyl, when
  a) R$^1$ is hydrogen, R$^2$ is hydrogen, R$^3$ is chloro, R$^4$ is hydrogen, R$^6$ is methyl, R$^7$ is hydrogen, R$^9$ is hydrogen, n is 0, X is C—R$^9$ and Y is N; or
  b) R$^1$ is hydrogen, R$^2$ is hydrogen, R$^3$ is chloro, R$^4$ is hydrogen, R$^6$ is methyl, R$^7$ is hydrogen, R$^{10}$ is hydrogen, n is 0, X is N and Y is C—R$^{10}$;

or a pharmaceutically active salt thereof.

2. The compound of claim 1, wherein R$^1$ is hydrogen.

3. The compound of claim 1, wherein R$^2$ is hydrogen or halogen.

4. The compound of claim 3, wherein R$^2$ is hydrogen, chloro or fluoro.

5. The compound of claim 1, wherein R$^3$ is halogen or lower alkyl.

6. The compound of claim 5, wherein R$^3$ is chloro or methyl.

7. The compound of claim 1, wherein R$^4$ is
  a) lower alkoxy, optionally substituted by halogen, hydroxyl, cycloalkyl or heterocyclyl,
  b) —O-aryl, or
  c) —O-heterocyclyl, wherein each S being part of a heterocyclyl is optionally substituted by oxo.

8. The compound of claim 1, wherein R$^4$ is —O-tetrahydropyranyl, —O-tetrahydrofuranyl, isopropoxy, tetrahydrofuranyl-ethoxy-, 4-chloro-2-hydroxy-butoxy-, 2-oxetanyl-propoxy-, 1,1,2,2-tetrafluoro-ethoxy-, chloro-hydroxy-isopentyloxy-, —O-tetrahydrothiopyranyl dioxide, tetrahydropyranyl-ethoxy-, 2,2,2-trifluoro-ethoxy-, 2-cyclopropyl-ethoxy-, —O-cyclopentyl, —O-cyclohexyl, i-butoxy, sec-butoxy, difluoro-isopropoxy-, —O-phenyl, 2,2,3,3,3-pentafluoro-propoxy- or trifluoro-isopropoxy-.

9. The compound of claim 1, wherein R$^5$ is fluoro or methyl.

10. The compound of claim 1, wherein R$^6$ is hydrogen.

11. The compound of claim 1, wherein R$^7$ is hydrogen.

12. The compound of claim 1, wherein R$^8$ is hydrogen.

13. The compound of claim 1, wherein R$^9$ is hydrogen, halogen or lower alkyl.

14. The compound of claim 13, wherein R$^9$ is hydrogen, fluoro or methyl.

15. The compound of claim 1, wherein R$^{10}$ is hydrogen or halogen.

16. The compound of claim 15, wherein R$^{10}$ is hydrogen or fluoro.

17. The compound of claim 1, wherein n is 0.

18. The compound of claim 1, wherein n is 1.

19. The compound of claim 1, having formula Ia,

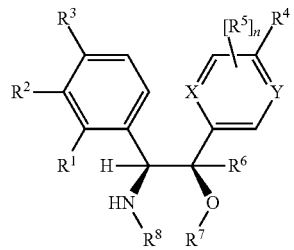

or a pharmaceutically active salt thereof.

20. The compound of claim 1, having formula Ib,

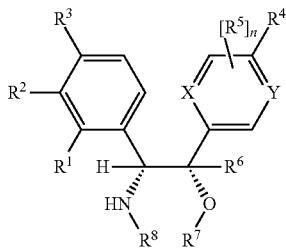

or a pharmaceutically active salt thereof.

21. The compound of claim 1, selected from the group consisting of
rac-erythro-[2-Amino-2-(3,4-dichloro-phenyl)-1-[5-(3-methanesulfonyl-phenyl)-pyridin-2-yl]-ethanol bistrifluoroacetate, and
rac-erythro-[2-Amino-2-(3,4-dichloro-phenyl)-1-(5'-fluoro-[3,3]bipyridinyl-6-yl)-ethanol trihydrochloride
or a pharmaceutically active salt thereof.

22. The compound of claim 1, selected from the group consisting of
rac-erythro-[2-Amino-2-(3,4-dichloro-phenyl)-1-[3-fluoro-5-(3-methoxy-phenyl)-pyridin-2-yl]-ethanol dihydrochloride,
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[rac-2-Amino-2-(3,4-dichloro-phenyl)-1-[6-(tetrahydro-furan-3-yloxy)-pyridin-3-yl]-ethanol dihydrochloride,
rac-erythro-[2-Amino-2-(3,4-dichloro-phenyl)-1-[4-methyl-6-(tetrahydro-pyran-4-yloxy)-pyridin-3-yl]-ethanol dihydrochloride,
rac-erythro-[2-Amino-2-(3,4-dichloro-phenyl)-1-[6-(tetrahydro-pyran-4-yloxy)-pyridin-3-yl]-ethanol dihydrochloride,
rac-erythro-[rac-2-Amino-2-(3,4-dichloro-phenyl)-1-[5-(tetrahydro-furan-3-yloxy)-pyridin-2-yl]-ethanol dihydrochloride, and
rac-erythro-[(rac)-2-Amino-2-(3,4-dichloro-phenyl)-1-[4-methyl-6-(tetrahydro-furan-3-yloxy)-pyridin-3-yl]-ethanol dihydrochloride
or a pharmaceutically active salt thereof.

23. The compound of claim 1, selected from the group consisting of
rac-erythro-[2-Amino-2-(3,4-dichloro-phenyl)-1-[5-(tetrahydro-pyran-4-yloxy)-pyridin-2-yl]-ethanol dihydrochloride,
rac-erythro-[2-Amino-2-(3,4-dichloro-phenyl)-1-[5-methyl-6-(tetrahydro-pyran-4-yloxy)-pyridin-3-yl]-ethanol dihydrochloride,
rac-erythro-[2-Amino-2-(3,4-dichloro-phenyl)-1-(6-isopropoxy-2-methyl-pyridin-3-yl)-ethanol dihydrochloride,
rac-erythro-[2-Amino-2-(3,4-dichloro-phenyl)-1-(6-isopropoxy-4-methyl-pyridin-3-yl)-ethanol dihydrochloride,
rac-erythro-[(rac)-2-Amino-2-(3,4-dichloro-phenyl)-1-[5-methyl-6-(tetrahydro-furan-3-yloxy)-pyridin-3-yl]-ethanol dihydrochloride, and
rac-erythro-[2-Amino-2-(3,4-dichloro-phenyl)-1-(5-isopropoxy-pyridin-2-yl)-ethanol dihydrochloride,
or a pharmaceutically active salt thereof.

24. The compound of claim 1, which is
rac-erythro-2-Amino-2-(4-chloro-phenyl)-1-(6-morpholin-4-yl-pyridin-3-yl)-ethanol,
or a pharmaceutically active salt thereof.

25. The compound of claim 1, selected from the group consisting of
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[rac-2-Amino-2-(3,4-dichloro-phenyl)-1-[6-(tetrahydro-furan-3-yloxy)-pyridin-3-yl]-ethanol dihydrochloride,
rac-erythro-[2-Amino-2-(3,4-dichloro-phenyl)-1-[4-methyl-6-(tetrahydro-pyran-4-yloxy)-pyridin-3-yl]-ethanol dihydrochloride, and
rac-erythro-[2-Amino-2-(3,4-dichloro-phenyl)-1-[6-(tetrahydro-pyran-4-yloxy)-pyridin-3-yl]-ethanol dihydrochloride or a pharmaceutically active salt thereof.

26. The compound of claim 1, selected from the group consisting of
rac-erythro-[rac-2-Amino-2-(3,4-dichloro-phenyl)-1-[5-(tetrahydro-furan-3-yloxy)-pyridin-2-yl]-ethanol dihydrochloride,
rac-erythro-[(rac)-2-Amino-2-(3,4-dichloro-phenyl)-1-[4-methyl-6-(tetrahydro-furan-3-yloxy)-pyridin-3-yl]-ethanol dihydrochloride,
rac-erythro-[2-Amino-2-(3,4-dichloro-phenyl)-1-[5-(tetrahydro-pyran-4-yloxy)-pyridin-2-yl]-ethanol dihydrochloride,
rac-erythro-[2-Amino-2-(3,4-dichloro-phenyl)-1-[5-methyl-6-(tetrahydro-pyran-4-yloxy)-pyridin-3-yl]-ethanol dihydrochloride,
rac-erythro-[2-Amino-2-(3,4-dichloro-phenyl)-1-(6-isopropoxy-2-methyl-pyridin-3-yl)-ethanol dihydrochloride,
rac-erythro-[2-Amino-2-(3,4-dichloro-phenyl)-1-(6-isopropoxy-4-methyl-pyridin-3-yl)-ethanol dihydrochloride,
rac-erythro-[(rac)-2-Amino-2-(3,4-dichloro-phenyl)-1-[5-methyl-6-(tetrahydro-furan-3-yloxy)-pyridin-3-yl]-ethanol dihydrochloride, and
rac-erythro-[2-Amino-2-(3,4-dichloro-phenyl)-1-(5-isopropoxy-pyridin-2-yl)-ethanol dihydrochloride
or a pharmaceutically active salt thereof.

27. The compound of claim 1, selected from the group consisting of
rac-erythro-[rac-2-Amino-2-(3,4-dichloro-phenyl)-1-[2-methyl-6-(tetrahydro-furan-3-yloxy)-pyridin-3-yl]-ethanol dihydrochloride,
rac-erythro-[2-Amino-2-(3,4-dichloro-phenyl)-1-[3-fluoro-4-(tetrahydro-pyran-4-yloxy)-phenyl]-ethanol hydrochloride,
rac-erythro-[rac-2-Amino-2-(3,4-dichloro-phenyl)-1-[6-(tetrahydro-furan-3-yloxy)-pyridin-3-yl]-ethanol dihydrochloride, and
rac-erythro-[2-Amino-2-(3,4-dichloro-phenyl)-1-[4-methyl-6-(tetrahydro-pyran-4-yloxy)-pyridin-3-yl]-ethanol dihydrochloride,
or a pharmaceutically active salt thereof.

28. A pharmaceutical composition comprising a therapeutically effective amount of a compound of formula I

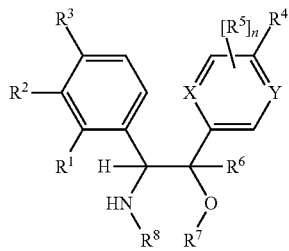

wherein
- $R^1$ is hydrogen, halogen or lower alkyl,
- $R^2$ is hydrogen, halogen or lower alkyl,
- $R^3$ is halogen or lower alkyl, which lower alkyl is optionally substituted by halogen,
- $R^4$ is a) lower alkyl, optionally substituted by halogen or lower alkoxy,
  b) lower alkoxy, optionally substituted by halogen, hydroxyl, cycloalkyl or heterocyclyl,
  c) —Si(lower alkyl)$_3$,
  d) —O-cycloalkyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  e) —O-aryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  f) —O-heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  g) —O-heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  wherein each S being part of a heterocyclyl is optionally substituted by oxo,
  h) heteroaryl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
  i) aryl, substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl, or
  j) heterocyclyl, optionally substituted by halogen, amido, nitro, acetyl, acetamidyl, lower alkyl, halogen-lower alkyl, lower alkoxy-lower alkyl, lower alkoxy, halogen-lower alkoxy, —NR$^{11}$R$^{12}$, or —S(O)$_2$-lower alkyl,
- and $R^4$ is hydrogen when $R^{10}$ is phenyl, wherein the phenyl is optionally substituted by halogen, lower alkyl, or —S(O)$_2$-lower alkyl,
- and $R^4$ is aryl when $R^6$ is lower alkyl,
- $R^5$ is halogen or lower alkyl,
- $R^6$ is hydrogen or lower alkyl,
- $R^7$ is hydrogen or lower alkyl,
- $R^8$ is hydrogen or lower alkyl,
- $R^9$ is hydrogen, halogen, lower alkyl or lower alkoxy,
- $R^{10}$ is hydrogen, halogen, lower alkyl or lower alkoxy,
- $R^{11}$ is hydrogen or lower alkyl,
- $R^{12}$ is hydrogen or lower alkyl,
- X is a) N and Y is C—R$^{10}$, or
  b) C—R$^9$ and Y is N, and
- n is 0 or 1, with the proviso that $R^8$ is lower alkyl, when
  a) $R^1$ is hydrogen, $R^2$ is hydrogen, $R^3$ is chloro, $R^4$ is hydrogen, $R^6$ is methyl, $R^7$ is hydrogen, $R^9$ is hydrogen, n is 0, X is C—R$^9$ and Y is N; or
  b) $R^1$ is hydrogen, $R^2$ is hydrogen, $R^3$ is chloro, $R^4$ is hydrogen, $R^6$ is methyl, $R^7$ is hydrogen, $R^{10}$ is hydrogen, n is 0, X is N and Y is C—R$^{10}$;

or a pharmaceutically active salt thereof and a pharmaceutically acceptable carrier.

* * * * *